United States Patent
Fu et al.

(10) Patent No.: US 8,412,465 B2
(45) Date of Patent: Apr. 2, 2013

(54) MICROARRAY-BASED GENE COPY NUMBER ANALYSES

(75) Inventors: Wenjiang Fu, Okemos, MI (US); Yalu Wen, East Lansing, MI (US); Ming Li, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 400 days.

(21) Appl. No.: 12/755,637

(22) Filed: Apr. 7, 2010

(65) Prior Publication Data

US 2010/0222225 A1 Sep. 2, 2010

Related U.S. Application Data

(63) Continuation-in-part of application No. 12/253,106, filed on Oct. 16, 2008, now abandoned.

(60) Provisional application No. 60/999,314, filed on Oct. 17, 2007.

(51) Int. Cl.
*G06F 19/00* (2011.01)
*C12Q 1/68* (2006.01)

(52) U.S. Cl. .......................................... 702/20; 435/6.1

(58) Field of Classification Search .................. None
See application file for complete search history.

(56) References Cited

PUBLICATIONS

Yang et al. Within the fold: assessing differential expression measures and reproducibility in microarray assays Genome Biology vol. 3 pp. research 0062.1-0062.12 (2002).*

* cited by examiner

*Primary Examiner* — John S Brusca
(74) *Attorney, Agent, or Firm* — Schwegman Lundberg & Woessner, P.A.

(57) ABSTRACT

This invention contemplates an accurate and efficient estimation of gene copy number using oligonucleotide microarrays. The method integrates gene copy number data obtained from perfect match and mismatch probe sequence structure intensities and probe binding affinities. In one embodiment, an accurate determination of single nucleotide polymorphisms (SNPs) sequences is obtained. In another embodiment, an accurate detection and determination of DNA copy number alteration is obtained. In another embodiment, an accurate estimation for RNA gene expression is obtained.

11 Claims, 23 Drawing Sheets

Genomic DNA            SNP

N N N N N G N N N $\genfrac{}{}{0pt}{}{A}{C}^{A}$ N N N N N N N N N N

Probe Quartet at SNP site

```
                 Interrogate
        1 2 3 4 5 6 7 8 9 10 11 12 | 13 | 14 15 16 17 18 19 20 21 22 23 24 25
      _ _ X X X X X X X X C X X X   T   X X X X X X X X X X X X  -5'   PM A allele
Array _ _ X X X X X X X X C X X X   A   X X X X X X X X X X X X  -5'   MM A allele
Surface _ _ X X X X X X X X C X X X   G   X X X X X X X X X X X X  -5'   PM B allele
      _ _ X X X X X X X X C X X X   C   X X X X X X X X X X X X  -5'   MM B allele
```

Probe Quartet at -4 offset

```
                 Interrogate
        1 2 3 4 5 6 7 8 9 10 11 12 | 13 | 14 15 16 17 18 19 20 21 22 23 24 25
      _ _ X X X X X X X X X X X X   C   X X X T X X X X X X X X  -5'   PM A allele
Array _ _ X X X X X X X X X X X X   G   X X X T X X X X X X X X  -5'   MM A allele
Surface _ _ X X X X X X X X X X X X   C   X X X G X X X X X X X X  -5'   PM B allele
      _ _ X X X X X X X X X X X X   G   X X X G X X X X X X X X  -5'   MM B allele
```

Figure 1

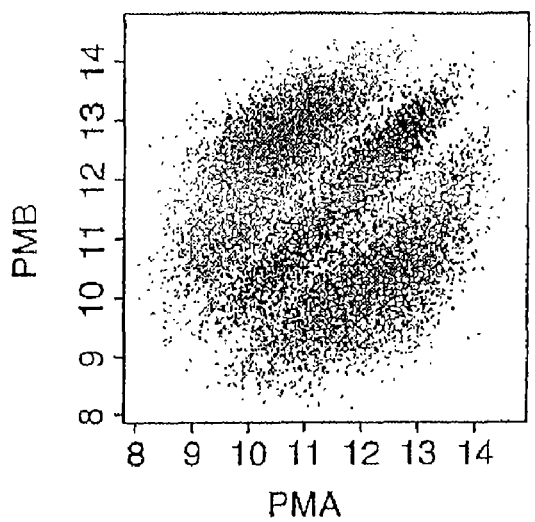
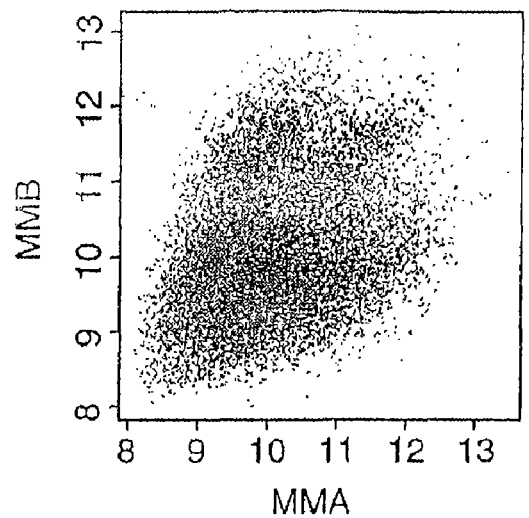
Fig. 3A
Fig. 3B
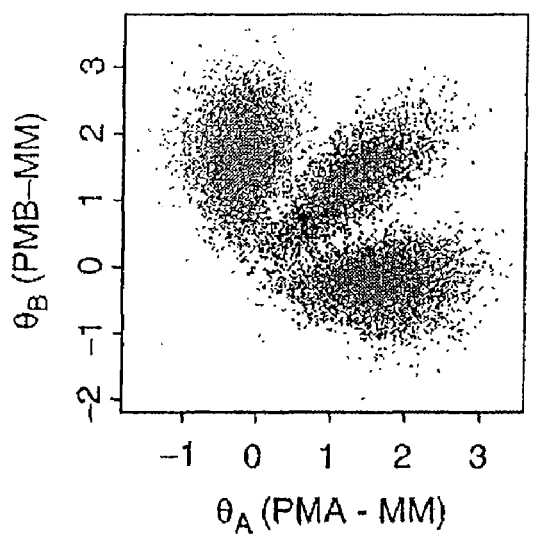
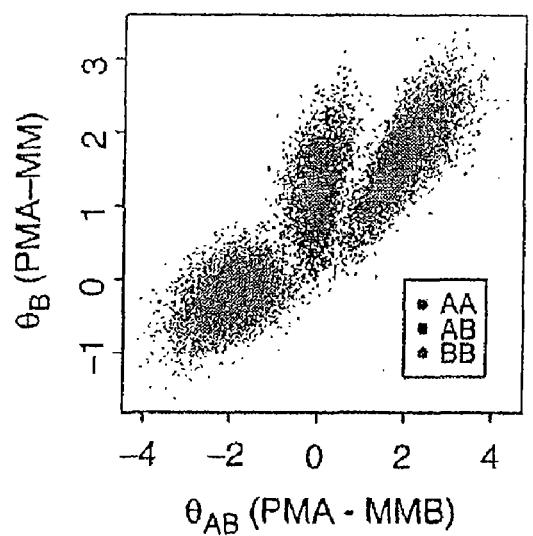
Fig. 3C
Fig. 3D

MICROARRAY-BASED GENE COPY NUMBER ANALYSES

CROSS-REFERENCE TO RELATED APPLICATIONS

This application is a continuation-in-part of, and claims priority to, pending U.S. patent application Ser. No. 12/253,106, filed on Oct. 16, 2008 now abandoned, and published as U.S. Pat. Pub. No. US 2009-0137417 A1 on May 28, 2009, which claims priority to U.S. provisional application Ser. No. 60/999,314, filed on Oct. 17, 2007, which is expired. Each of which is herein incorporated by reference in its entirety.

FIELD OF INVENTION

The present invention is related to methods for microarray data analysis to facilitate accurate and efficient identification of DNA copy numbers and its applications. For example, SNP genotyping can be determined based on DNA copy numbers, as well as detecting gene copy number alterations. Alternatively, gene expression analysis using RNA gene expression microarrays may also be performed by determination of gene copy numbers.

BACKGROUND

An unparalleled level of complexity in data analysis has been introduced in the current post-genome era including computationally intensive high throughput technology (including microarrays), large scale computing, data mining oriented genomic research (i.e., for example, the international HapMap project), genome-wide association studies, genomic profiling applications to pharmacogenetics and translational therapeutic treatments, and drug/medical treatment developments. In particular, the widespread use of microarrays (i.e., for example, Affymetrix Inc., Santa Clara, Calif.) provide routine implementation of high-throughput research that requires a high level of sophisticated data analysis.

Currently used microarray methods are capable of genotyping single nucleotide polymorphisms (SNPs) based upon probe label intensities or identifying differentially expressed genes using data obtained from oligonucleotide microarrays. Disadvantages of these methods are primarily due to the dependence upon using probe label intensities from oligonucleotide arrays based on the belief that the intensity of perfect match sequences provides an accurate proportionality to the reference gene copy number. Further, another misleading belief is that mismatch sequences only provide background information as a result of non-specific binding. Such beliefs ignore the fact that probe label intensities depend on factors other than just gene copy number. An efficient and accurate estimation of unobservable copy numbers from oligonucleotide microarrays to determine SNP genotypes is difficult to obtain using these existing techniques.

What is needed is a method to determine genetic variations for DNA genotyping and differentiation in gene expression using determinations in gene copy number calculated by not only probe label intensity data but with other factors such as probe binding affinity to the reference sequence.

SUMMARY

The present invention is related to methods for microarray data analysis to facilitate accurate and efficient identification of DNA copy numbers and its applications. For example, SNP genotyping can be determined based on DNA copy numbers, as well as detecting gene copy number alterations. Alternatively, gene expression analysis using RNA gene expression microarrays may also be performed by determination of gene copy numbers.

In one embodiment, the present invention contemplates a method, comprising: a) providing: i) a microarray comprising a plurality of oligonucleotides, at least one oligonucleotide of said plurality comprising a portion of a first allele; ii) a labeled first probe having complete complementarity to a region of said oligonucleotide comprising a portion of a first allele; and, iii) a labeled second probe having partial complementarity to a region of said oligonucleotide comprising a portion of a first allele; b) exposing said microarray to said first and second probes under hybridizing conditions; c) determining intensity measurements from said first and second probes; and d) applying the Langmuir adsorption model to both first and second probe intensity measurements. In one embodiment, the exposing of step b) is done in series, wherein said microarray is first exposed to said first probe, and thereafter exposed to said second probe. In one embodiment, the oligonucleotides of said microarray are selected from the group comprising 5-101 nucleotides in length. In one embodiment, the oligonucleotides of said microarray are at least 25 nucleotides in length. In one embodiment, the region of said oligonucleotide comprising a portion of a first allele is between 13 and 20 nucleotides in length. In one embodiment, the probes are fluorescently labeled. In one embodiment, the Langmuir adsorption model calculates a gene copy number. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method, comprising: a) providing: i) a microarray comprising a first oligonucleotide and second oligonucleotide, said first oligonucleotide comprising a portion of a first allele, said second oligonucleotide comprising a portion of a second allele; ii) a labeled first probe having partial complementarity to a region said first oligonucleotide; iii) a labeled second probe having complete complementarity to a region of said first oligonucleotide; iv) a labeled third probe having partial complementarity to a region of said second oligonucleotide; and v) a labeled fourth probe having complete complementarity of a region of said second oligonucleotide; b) exposing said first, second, third and fourth probes to said microarray under hybridization conditions to create bound probes; c) determining intensity measurements from said bound probes; and, d) determining a copy number for said first allele and said second allele using said intensity measurements of step c) and an algorithm, without subtracting said intensity measurements of said first and third probes. In one embodiment, the exposing of step b) is done in series, wherein said microarray is first exposed to said first probe, and thereafter exposed to said second probe, and thereafter exposed to said third probe, and thereafter exposed to said fourth probe. In one embodiment, the oligonucleotides of said microarray are selected from the group comprising 5-101 nucleotides in length. In one embodiment, the oligonucleotides of said microarray are at least 25 nucleotides in length. In one embodiment, the region of said oligonucleotide comprising a portion of a first allele is between 13 and 20 nucleotides in length. In one embodiment, the probes are fluorescently labeled. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method, comprising: a) providing a microarray comprising a first oligonucleotide probe having complete complementarity to a portion of a first allele, and a second oligonucleotide probe having partial complementarity to a portion of a first allele; b) exposing said microarray to target nucleic acid under hybridizing conditions, said target nucleic acid comprising at least one copy of said first allele, so as to create bound target nucleic acid; c) determining intensity measurements from said target nucleic acid; and, d) applying the Langmuir adsorption model to both first and second probe intensity measurements. In one embodiment, the target nucleic acid comprises a plurality of copies of said first allele. In one embodiment, the oligonucleotides of said microarray are selected from the group comprising 5-101 nucleotides in length. In one embodiment, the oligonucleotides of said microarray are at least 25 nucleotides in length. In one embodiment, the second oligonucleotide probe has a single base mismatch. In one embodiment, the target nucleic acids are labeled. In one embodiment, the Langmuir adsorption model calculates a gene copy number. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method, comprising: a) providing: a microarray comprising a first oligonucleotide probe, second oligonucleotide probe, third oligonucleotide probe and fourth oligonucleotide probe, said first oligonucleotide probe having partial complementarity to a region of a first allele, said second probe having complete complementarity to a region of said first allele, said third oligonucleotide probe having partial complementarity to a region of a second allele, said fourth oligonucleotide probe having complete complementarity to a region of said second allele; b) exposing said first, second, third and fourth probes of said microarray to target nucleic acid under hybridization conditions, said target nucleic acid comprising at least one copy of said first and second alleles, so as to create bound probes; c) determining intensity measurements from said target nucleic acids; and, d) determining a copy number in said target nucleic acid for said first allele and said second allele using said intensity measurements of step c) and an algorithm, without subtracting said intensity associated with the binding of said first and third oligonucleotide probes. In one embodiment, the target nucleic acid comprises a plurality of copies of said first and second alleles. In one embodiment, the oligonucleotides of said microarray are selected from the group comprising 5-101 nucleotides in length. In one embodiment, the oligonucleotide probes of said microarray are at least 25 nucleotides in length. In one embodiment, the first and third oligonucleotide probes have a single base mismatches. In one embodiment, the target nucleic acids are labeled. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method, comprising: a) providing: i) a microarray comprising at least one oligonucleotide comprising an allele A and an allele B; ii) a labeled mismatch probe having at least partial complementarity to said allele A; and, iii) a labeled mismatch probe having at least partial complementarity to said allele B; b) applying said mismatch probes to said microarray under conditions such that said mismatch probes bind to said oligonucleotide; c) estimating binding free energy of said mismatch probes using a first statistical model; d) determining intensity measurements from said mismatch probes; and, e) determining a gene copy number for said allele A and allele B using a second statistical model, wherein said second model incorporates said mismatch probe binding free energy estimates and said mismatch probe intensity measurement determinations. In one embodiment, the oligonucleotide is selected from the group consisting of deoxyribonucleotides and ribonucleotides. In one embodiment, the binding free energy is determined by a generalized positional-dependent nearest neighbor statistical model. In one embodiment, the method further comprises repeating steps (b)-(e) using also a perfect match labeled probe for said allele A and a perfect match labeled probe for said allele B. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method, comprising: a) providing: i) a microarray comprising at least one oligonucleotide comprising an allele A and an allele B; ii) a labeled mismatch probe having at least partial complementarity to said allele A; and, iii) a labeled mismatch probe having at least partial complementarity to said allele B; b) applying said mismatch probes to said microarray under conditions such that said mismatch probes bind to said oligonucleotide; c) estimating binding free energy of said mismatch probes using a first statistical model; d) determining intensity measurements from said mismatch probes; and, e) determining a gene copy number for said oligonucleotide using a second statistical model, wherein said second model incorporates said mismatch probe binding free energy estimates and said mismatch probe intensity measurement determinations, and f) determining a genotype of said oligonucleotide based on said copy number determination. In one embodiment, the oligonucleotide is selected from the group consisting of deoxyribonucleotides and ribonucleotides. In one embodiment, the binding free energy is determined by a generalized positional-dependent nearest neighbor statistical model. In one embodiment, the high density microarray is selected from the group consisting of a 100K microarray, a 500K microarray, and a 1000K microarray (also known as Affymetrix 6.0 SNP array). In one embodiment, the method further comprises repeating steps (b)-(e) using also a perfect match labeled probe for said allele A and a perfect match labeled probe for said allele B. In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method of determining copy number of genes, comprising: a) applying an oligonucleotide to a high density genotyping array comprising a perfect match probe to allele A and a mismatch probe to allele A and a perfect match probe to allele B and a mismatch probe to allele B, b) estimating binding free energy of said perfect match probe hybridization from a first statistical model; c) estimating binding free energy of said mismatch probe hybridization from a second statistical model; d) determining intensity measurements for each of said perfect match probes and said mismatch probes from a third statistical model, and e) determining a gene copy number alteration of said allele A and said allele B of said oligonucleotide based on said determination of intensity measurement. In one embodiment, the oligonucleotide is selected from the group consisting of deoxyribonucleotides and ribonucleotides. In one embodiment, binding free energy is determined by a generalized positional-dependent nearest neighbor statistical model. In one embodiment, the high density microarray is selected from the group consisting of a 100K microarray, a 500K microarray, and a 1000K microarray (also known as Affymetrix 6.0 SNP array). In one embodiment, the allele A mismatch probe and said allele B mismatch probe have at least partial identity with said target sequence. In one embodiment, the first statistical model is derived from parameters selected from the group consisting of said perfect match probe sequence, a first position weight factor, and a first stacking energy factor. In one embodiment, the second statistical model is derived from parameters selected from the group consisting of said perfect match probe sequence, a second position weight factor, a second stacking energy factor, and mismatch location. In one embodiment, the third statistical model is derived from parameters selected from the group consisting of a binding function, copy number estimation, binding free energies of said perfect match probes and said mismatch probes, random error factor, and baseline intensity (i.e., intensity partially resulting from non-specific binding and/or array specific intensity—systemic deviations). In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method of determining a genotype, comprising: a) applying an oligonucleotide to a high density genotyping array comprising a perfect match probe to allele A and a mismatch probe to allele A and a perfect match probe to allele B and a mismatch probe to allele B, b) estimating binding free energy of said perfect match probe hybridizations from a first statistical model; c) estimating binding free energy of said mismatch probe hybridizations from a second model equation; d) determining intensity measurements for each of said perfect match probes and said mismatch probes from a third statistical model; e) determining a gene copy number of said allele A and said allele B of said oligonucleotide based on said intensity measurement, and f) determining a genotype of said oligonucleotide. In one embodiment, the oligonucleotide is selected from the group consisting of deoxyribonucleotides and ribonucleotides. In one embodiment, the binding free energy is determined by a generalized positional-dependent nearest neighbor statistical model. In one embodiment, the high density microarray is selected from the group consisting of a 100K microarray, a 500K microarray, and a 1000K microarray (also known as Affymetrix 6.0 SNP array). In one embodiment, the allele A mismatch probe and said allele B mismatch probe have at least partial identity with said target sequence. In one embodiment, the first statistical model is derived from parameters selected from the group consisting of said perfect match probe sequence, a first position weight factor, and a first stacking energy factor. In one embodiment, the second statistical model is derived from said mismatch probe sequence, a second position weight factor, a second stacking energy factor, and nucleotide mismatch location. In one embodiment, the third statistical model is derived from a binding function, copy number estimation, said binding free energies of said perfect match probes and said mismatch probes, random error factor, and baseline intensity (i.e., intensity partially resulting from non-specific binding and/or array specific intensity—systemic deviations). In one embodiment, the gene copy number is used to determine a DNA gene copy number alteration. In one embodiment, the gene copy number reflects differential RNA gene expression. In one embodiment, the gene copy number reflects an SNP genotype.

In one embodiment, the present invention contemplates a method of determining a genotype, comprising: a) providing a microarray; and b) generating genotype calling for said microarray wherein said generating comprises an algorithm, said algorithm utilizing an MA ratio [M is the intensity ratio and A is the average intensity for a dot in a dot plot where the plot is used to visualize two channel microarray gene expression data]. In one embodiment, the microarray is an individual array and is optionally an on-line feature. In one embodiment, the genotype calling further comprises storing all microarray information in a algorithm as constants for optimal output. In one embodiment, the genotype calling further comprises using a first and a second extreme cut-off wherein said first extreme cutoff is up to 1% from the top of the data range and said second extreme cut-off is up to 1% from the bottom of the data range. In one embodiment, the microarray contains a plurality of SNPs with three annotated genotype groups. In one embodiment, the microarray contains SNPs with only one annotated homozygous genotype and one annotated heterozygous genotype. In one embodiment, further comprising determining a first and a second cut-off for each said genotype. In one embodiment, the microarray contains a plurality of SNPs wherein said plurality contains only two annotated homozygous genotypes. In one embodiment, the microarray contains a plurality of SNPs wherein said plurality contains only one annotated homozygous genotype. In one embodiment, the microarray contains a plurality of SNPs wherein said plurality contains only SNPs with heterozygous annotation. In one embodiment, the microarray contains a plurality of SNPs wherein said plurality contains no annotation.

In one embodiment, the present invention contemplates a method of generating copy numbers, comprising: a) providing a microarray; and b) generating copy numbers for said microarray wherein said generating comprises an algorithm, said algorithm utilizing an MA ratio [M is the intensity ratio and A is the average intensity for a dot in a dot plot where the plot is used to visualize two channel microarray gene expression data]. In one embodiment, the microarray is an individual array and is optionally an on-line feature. In one embodiment, the copy number further comprises storing all microarray information in a algorithm as constants for optimal output. In one embodiment, the copy number further comprises using a first and a second extreme cut-off wherein said first extreme cutoff is up to 1% from the top of the data range and said second extreme cut-off is up to 1% from the bottom of the data range. In one embodiment, the generating further comprises incorporating a HapMap clustering structure into the algorithm for improved accuracy.

In one embodiment, the present invention contemplates a method of determining a copy number, comprising: a) providing: i) a microarray comprising a first oligonucleotide and second oligonucleotide, said first oligonucleotide comprising a portion of a first allele, said second oligonucleotide comprising a portion of a second allele; ii) labeled first probe having partial complementarity to a region said first oligonucleotide [mismatch for allele A (MA)]; iii) a labeled second probe having complete complementarity to a region of said first oligonucleotide [perfect match for allele A (PA)]; iv) a labeled third probe having partial complementarity to a region of said second oligonucleotide [mismatch for allele B (MB)]; and v) a labeled fourth probe having complete complementarity of a region of said second oligonucleotide [perfect match for allele B (PB)]; and b) exposing said first, second, third and fourth probes to said microarray under hybridization conditions to create bound probes; c) determining intensity measurements from said bound probes; and, d) determining a copy number for said first allele and said second allele using said intensity measurements of step c) and an algorithm, said algorithm utilizing an MA ratio [M is the intensity ratio and A is the average intensity for a dot in a dot plot where the plot is used to visualize two channel microarray gene expression data].

In one embodiment, the present invention contemplates a method for genotype calling using individual arrays (e.g. Affy 500 K arrays), which can be an on-line feature that does not require pooling multiple arrays together. In one embodiment, the method is used to generate SNP genotype calls extremely fast by storing all array information in the algorithm as constants for optimal output. In one embodiment, the method incorporates the HapMap clustering structure into the algorithm, which improves accuracy. In another embodiment, the SNP-wise criteria are implemented by training the HapMap annotation or by unsupervised learning. In one embodiment, the method uses an extreme cut-off of up to 1% from the top of the range and up to 1% from the bottom of the range. In another embodiment, the present invention contemplates a method for using the two observed genotype groups to form a cut-off value between AA and AB (or BB and AB) groups. In one embodiment, for example only and not to be limiting, the MA ratio is used for generating an allelic copy number. In one embodiment, the present invention contemplates a MA ratio for use with a method for copy number determination that increases accuracy and lowers false positive and/or false negative rates. Moreover, while specific examples are given they are not meant to be limiting and include similar materials, methods, and approaches known to one of skill in the art.

Definitions

The term, "microarray" as used herein, refers to a substrate with a plurality of molecules (e.g., oligonucleotides) bound to its surface. Microarrays, for example, are described generally in Schena, "Microarray Biochip Technology," Eaton Publishing, Natick, Mass., 2000. Additionally, a microarray may comprise a plurality of molecules non-randomly bound to its surface (i.e., for example, arrayed oligonucleotides). For example, a microarray may comprises arrayed labeled probes designed for applying target oligonucleotides. Alternatively, a microarray may comprise arrayed target oligonucleotides designed for applying labeled probes. Such microarrays may comprise from between 0K-100,000K arrayed oligonucleotides, preferably between 500-50,000K arrayed oligonucleotides, more preferably between 1,000K-5,000K arrayed oligonucleotides, but most preferably between 500K-1,000K oligonucleotides for SNPs. Furthermore, for example only and not meant to be limiting, generally probe sequences comprise about 25 nt in Affymetrix arrays, and about 60 nt in Agilent arrays.

The term "oligonucleotide" as used herein, refers to any molecule comprising two or more deoxyribonucleotides or ribonucleotides, preferably at least 4 nucleotides, more preferably at least about 10-15 nucleotides, and more preferably at least about 15 to 200 nucleotides. The exact size will depend on many factors, which in turn depend on the ultimate function or use of the oligonucleotide. The oligonucleotide may be generated in any manner, including chemical synthesis, DNA replication, reverse transcription, PCR, ligation, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. An oligonucleotide sequence is written in 5'- to 3' direction by convention.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the thermodynamics of the formed hybrid. "Hybridization" methods involve the annealing of one nucleic acid to another, complementary nucleic acid, i.e., a nucleic acid having a complementary nucleotide sequence (or at least partially complementary sequence). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology.

The term "homology" and "homologous" refers to a degree of identity of at least two compounds or sequences. There may be partial homology or complete homology. A partially homologous sequence is one that is less than 100% identical to another sequence (i.e., for example, having "partial identity").

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "allele" as used herein, is a genomic locus present in a population that shows variation between members of the population (e.g., the most common allele has a frequency of less than 0.95). Generally, most genes comprise at least two alleles (i.e., for example, allele A and allele B) coding for different phenotypes of a similar characteristic (i.e., for example, brown eyes or blue eyes).

The term "probe", as used herein, refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). In some embodiments, it is contemplated that probes used in the present invention are labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular label. With respect to microarrays, the term probe is used to refer to any hybridizable material that may, or may not, be affixed to the microarray for the purpose of detecting "target" sequences. Probes may range in nucleotide sequence from between approximately 5-101 nucleotides, preferably from between approximately 10-75 nucleotides, more preferably from between approximately 15-50 nucleotides, but most preferably from between approximately 20-30 nucleotides. Furthermore, the use of "MA" in the context of probes, refers to a probe that is a mismatch for an allele, such as allele A. Such probes are used with arrays, such as the Affymetrix GeneChip Mapping Arrays, which consist of a large number of probes containing 25-base oligonucleotides designed to test a given sequence. The probes are grouped in quartets: perfect match for allele A (PA), mismatch for allele A (MA), perfect match for allele B (PB) and mismatch for allele B (MB). The mismatch probes are used to measure the magnitude of cross-hybridization. For the 'AA' genotype, it is expected that the intensity of PA is higher than that of MA, PB and MB, and for the 'AB' genotype it is expected that the intensities of PA and PB are higher than those of MA and MB. The information available in the data files that are part of the output of the imaging software consist, for each probe, of the number of pixels ($n_x$) corresponding to the probe, the mean ($\bar{x}$) and the standard deviation ($s_x$) of the pixel intensity.

The term, "shift k range" as used herein, refers to the hybridization position of a mismatch probe relative to its center nucleotide position. Consequently, a "shift k range" takes positive and negative limits of equal numerical absolute value. For example, a 25-mer probe would have a shift k range of between +7 . . . −7, with a center nucleotide position of 13. Alternatively, an 11-mer probe would have a shift k range of between +5 . . . −5 with a center nucleotide position of 6. Further, a 55-mer probe would have a shift range of between +27 . . . −27 with a center nucleotide position of 28.

The term, "mismatch probe" as used herein, refers to any probe having partial complementarity to a target sequence (preferably one or two base mismatches, with other bases completely homologous to the target sequence).

The term, "perfect match probe" as used herein, refers to any probe having complete complementarity to a target sequence.

The term "label" or "labeled" as used herein, refers to any atom or molecule that can be used to provide a detectable (preferably quantifiable) signal, and that can be attached to a nucleic acid or protein or other polymers. Such a label may be attached to an oligonucleotide probe (i.e., for example, a perfect match probe and/or a mismatch probe) or such a label may be attached to a target oligonucleotide. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. The detectable signals of the labels may be quantitated by "intensity measurements" wherein an increased signal strength from a higher concentration of label, is detected as an increase intensity. Alternatively, an intensity measurement of a label attached to a first oligonucleotide may change (i.e., for example, modify) "when associated with the binding of (i.e., for example, hybridization" a second oligonucleotide.

The term "target" or "target sequence" when used in reference to hybridization assays, refers to the molecules (e.g., nucleic acid) to be detected. Thus, the "target" is sought to be sorted out from other molecules (e.g., nucleic acid sequences) or is to be identified as being present in a sample through its specific interaction (e.g., hybridization) with another agent (e.g., a probe oligonucleotide). A "segment" is defined as a region of nucleic acid within the target sequence.

The term "bind" or "binding" as used herein, refers to any stable interaction between at least two molecules. The interaction may be mediated by forces including, but not limited to, non-covalent, covalent, ionic, Van der Waals, hydrophobic, electrostatic and the like.

The term "binding free energy" as used herein, when used in reference to the nucleic molecules of the present invention, refers to the energy released when a complementary sequence is sufficient to allow hybridization of the nucleic acid to proceed. Determination of binding free energies for nucleic acid molecules has been reported. (see, e.g., Turner et al., 1987, CSH Symp. Quant. Biol. LII pp. 123 133; Frier et al., 1986, Proc. Nat. Acad. Sci. USA 83:9373 9377; Turner et al., 1987, J. Am. Chem. Soc. 109:3783 3785).

The term "statistical model" as used herein, refers to any grouping of formula (or equations) designed to perform a mathematical calculations based upon measured data (i.e., for example, probe label intensity). Such statistical models may also be based upon logical assumptions for which proving data may or may not be available. One such preferred statistical model is a "generalized positional-dependent nearest neighbor statistical model" (GPDNN) which utilizes data collected from both perfect match probe label intensity and mismatch label intensity. Another statistical model may determine "binding free energy" of probe hybridizations to oligonucleotides, or calculate random intercepts via linear regression formulae. Alternatively, a "binding free energy" model may also provide a formula to determine the "binding function" which describes the quantitative parameters involved in nucleotide hybridization processes.

The term "Langmuir adsorption model", as used herein, refers to an equation and/or isotherm relating the coverage or adsorption of molecules on a solid surface to gas pressure or concentration of a medium above the solid surface at a fixed temperature. The equation was developed by Irving Langmuir in 1916. The original equation is stated as:

$$\theta = \frac{\alpha \cdot P}{1 + \alpha \cdot P}$$

where, θ or theta is the percentage coverage of the surface, P is the gas pressure or concentration, α alpha is a constant. The Langmuir equation may also be used to describe the relationship between the concentration of a compound adsorbing to binding sites and the fractional occupancy of the binding sites.

The term "perfect match probe sequence" as used herein, refers to the primary nucleotide sequence of an oligonucleotide probe (i.e., for example, a 25-mer). Such a probe might be designed to have complete identity to a suspected target sequence on an oligonucleotide.

The term "position weight factor" as used herein, refers to a correction factor integrated into a statistical model directed towards the exact location of a mismatch probe hybridization relative to the center nucleotide of the mismatch probe. For example, the value of the "position weight factor" changes as the position of the mismatch probe moves along the probes' sequence (i.e., for example, as the mismatch/perfect match probe short sequence (pair or triplet moves along the target sequence, the position weight factor fluctuates, so as the position/location moves, the free-energy changes).

The term, "stacking energy factor" as used herein, refers to a potential energy gain attained by fixing the positions of adjacent nucleotide bases over each other as a non-random structure during hybridization.

The term "mismatch location" as used herein, refers to the area of a mismatch probe hybridization shift relative to the center nucleotide of the probe. Such a hybridization shift represents a partial overlap of the mismatch probe with the target sequence.

The term "random error factor" as used herein, refers to a generally accepted correction factor to control for known, but uncontrollable, effects occurring during hybridization (i.e., for example, non-specific hybridization, scanning, and/or intensity reading).

The term "baseline intensity" as used herein, refers to measurements taken to detect probe label intensity before the probe is applied to a microarray. Consequently, the acquired value is subtracted from the "intensity measurement" to obtain an accurate determination of probe hybridization to a target sequence. Further, such baseline intensity is believed to be partially resulting from non-specific binding and/or array specific intensity—systemic deviations often observed in microarray detection technology.

The term "gene copy number" as used herein, refers to a quantitative representation of a duplicated gene on an oligonucleotide. For example, if Gene A has a copy number of twenty-five (25), then Gene A is duplicated twenty-five times on an oligonucleotide. The present invention contemplates a method to provide a "copy number estimation" wherein the estimation is further used, in conjunction with binding free energy, to accurately determine copy number.

The term "genotype" as used herein refers to the primary nucleotide sequence of a gene, or partial gene.

The term "MA ratio" as used herein refers to an equation relating to comparison of two channel microarray gene expression data, within the context of data analysis:

$$r = (N_A - N_B)/|N_A + N_B|$$

Further, in cDNA microarray data analysis, M is the log intensity ratio, $= \log 2(R) - \log 2(G)$, while A is the log intensity average, $= \frac{1}{2}[\log 2(R) + \log 2(G)]$. Where R is the intensity of red dye and G is the intensity of green dye. In the current analysis, the log intensity is replaced by the copy number of alleles, i.e. the NA and NB and thus forms the M and A as $M = N_A - N_B$ and $A = |N_A + N_B|$. Where the ratio M/A is then taken. Thus, in doing so, any scaling factor in the array will also be cancelled out as well. Furthermore, MA, within the context of data analysis such as "MA ratio" is related to use of an MA plot also known as a Bland-Altman plot for visual representation of two channel DNA microarray gene expression data that has been transformed into the M and A scale. As known in the art the M refers to the intensity ratio while A is the average intensity for a dot in the plot.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 illustrates one embodiment of an SNP microarray design.

FIG. 2 presents illustrative data showing copy number estimation and genotype calling using different probes on HapMap data. SNPs types are labeled with different colors: AA SNPs green; BB SNPs red; AB SNPs blue;

FIG. 3 presents exemplary scatter plot data using SNP probe intensity data as reported by Xiao et al., "A. multi-array multi-SNP genotyping algorithm for Affymetrix SNP microarrays" *Bioinformatics* 23:1459-1467 (2007) using mismatch adjustment by subtracting total mismatches from allele-specific perfect matches.

FIG. 3A: perfect matches for allele A and allele B.

FIG. 3B: mismatches for allele A and allele B;

FIG. 3C: perfect matches for allele A adjusted by mismatches versus perfect matches for allele B adjusted by mismatches;

FIG. 3D: summary statistic of perfect matches for allele A adjusted by mismatches versus perfect matches for allele A adjusted by perfect matches for allele B.

FIG. 4 presents exemplary scatter plot data of probe intensities to target sequences of homozygous SNPs at mismatch positions. The line in each plot is a linear regression line based on the data at each position. The regression slope and Pearson correlation coefficient are shown on each plot. The large slopes of MM1 and PM2 on PM1 indicate comparable intensity and the small slopes of MM2 on PM1 indicate a smaller intensity of MM2 probes resulting from one more mismatch nucleotide. This disparity indicates that specific binding, rather than nonspecific binding, is dominant in mismatch probes, which implies that modeling of both perfect match probes and mismatch probes leads to improved accuracy.

SNP_A-1756140 of 'AA' type; Right panel—SNP_A-1652710 of 'BB' type. Although the GPDNN model was trained with only one sample, intensity prediction by the PICR model performed well.

FIG. 6 presents exemplary scatter plot data of allelic copy numbers estimated for one randomly selected non-training sample (NA07056_Xba_A11_4000090) by PICR.

Figure 6A:
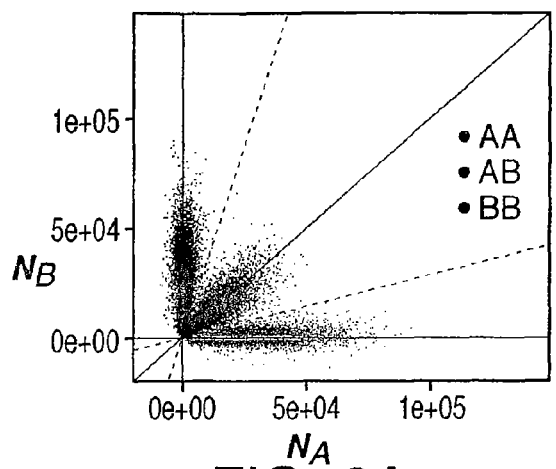

FIG. 6A: Using all probes in the probe set.

Figure 6B:
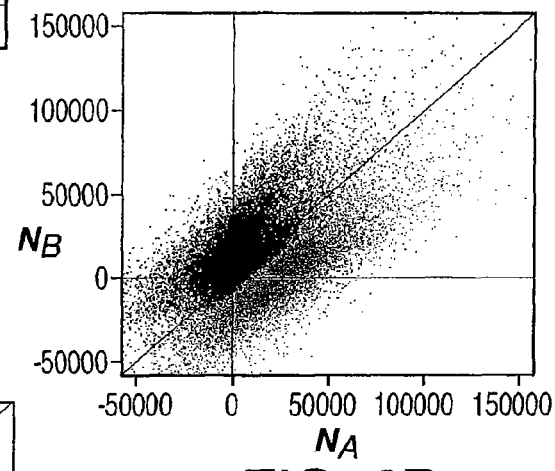

FIG. 6B; Using only PA and PB probes.

Figure 6C:
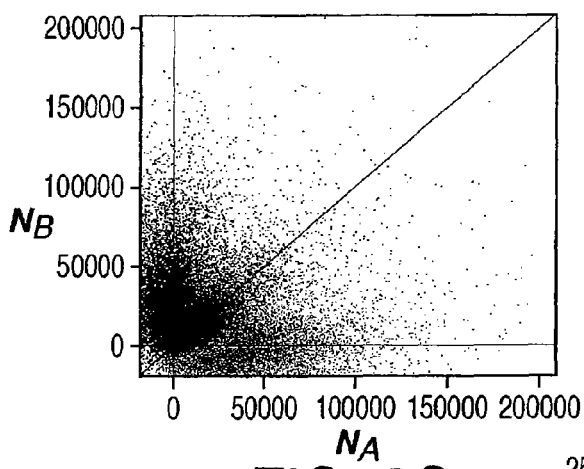

FIG. 6C: Using only MA and MB probes.

Figure 6D:
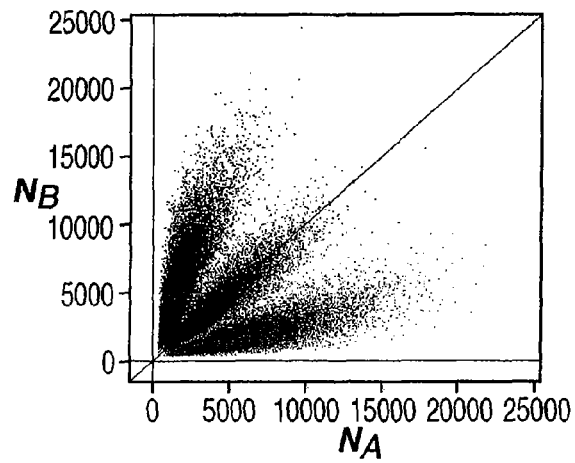

FIG. 6D: Using mean intensity of perfect match probes PA versus PB.

'AA' SNPs in green; 'AB' SNPs in blue; and 'BB' SNPs in red. The estimation for homozygous SNPs indicates that excluding mismatch probes (B) led to biased estimation of copy numbers: $N_A>0$ for 'BB' SNPs and $N_B>0$ for 'AA' SNPs, while using only mismatch probes (C) led to nearly unbiased estimation but with much larger variability due to loss of the information in the perfect match probes. The use of mean intensity as a surrogate for allelic copy numbers (D), such as mean PA for $N_A$ and mean PB for $N_B$, led to biased estimation of copy numbers: $N_A>0$ for 'BB' SNPs and $N_B>0$ for 'AA' SNPs.

Figure 7:
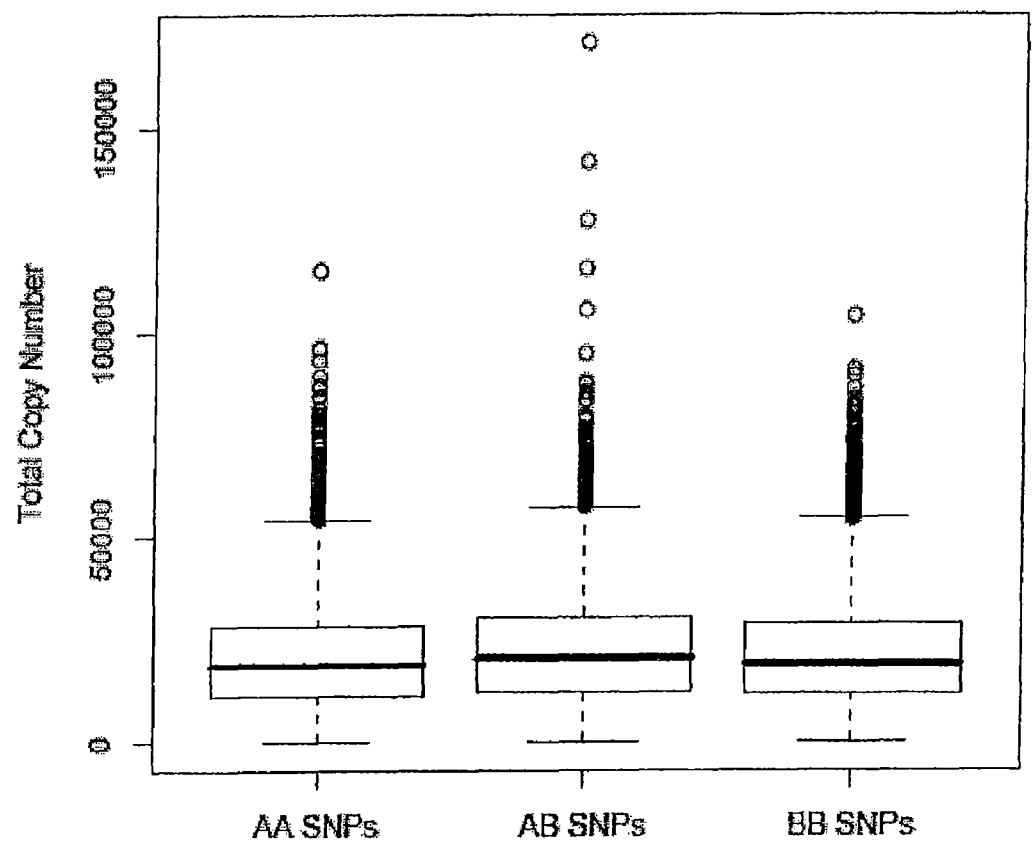
Figure 8A:
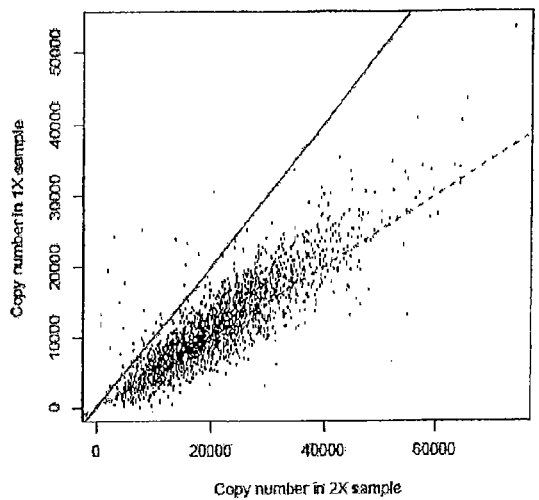
Figure 8B:
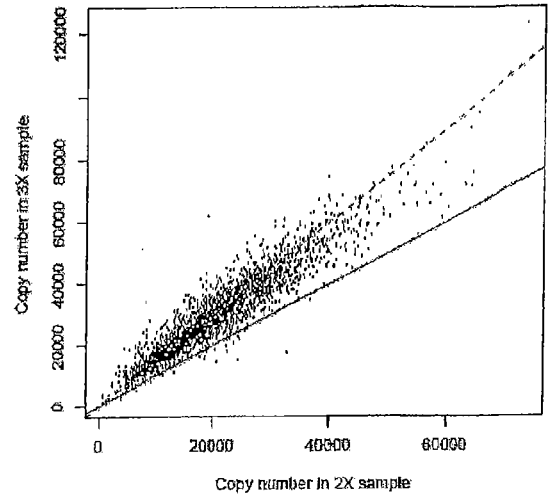
Figure 8C:
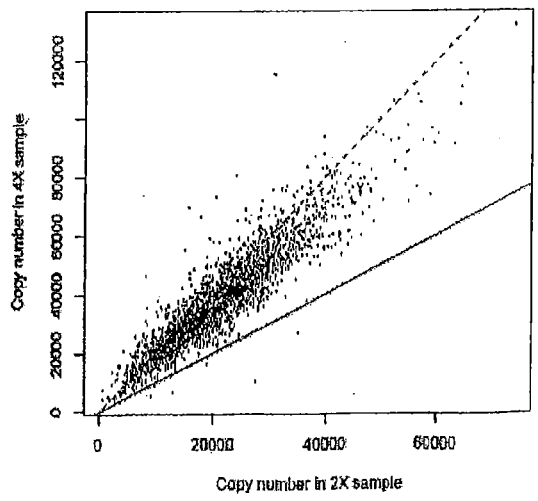
Figure 8D:
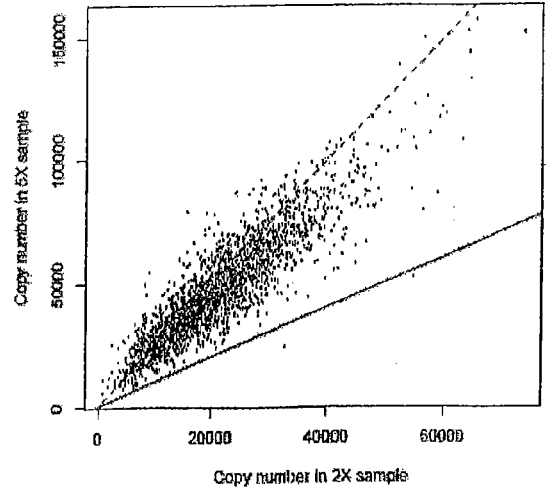

FIG. 7 presents exemplary data comparing total copy numbers ($N_{total}=N_A+N_B$) of all SNPs through boxplots for genotypes 'AA', 'BB' and 'AB', as annotated with the PICR model, in one randomly selected non-training sample (NA07056_Xba_A11_4000090). Because no insertion or deletion is expected for this normal subject, the observation of equal distributions of the total copy number across different genotypes indicates accurate estimation of the copy number by the PICR model.

FIG. 8 presents exemplary scatter plot data of adjusted copy numbers of all 2,361 SNPs on the X-chromosome in cell-line data. FIG. 8A: 1X sample versus 2X sample; FIG. 8B: 3X sample 24 versus 2X sample; FIG. 8C: 4X sample versus 2X sample; FIG. 8D: 5X sample versus 2X sample. Solid lines in each panel represent the diagonal true copy number 2X, and dotted lines represent ratios of true copy numbers (1, 3, 4 and 5 versus 2). The closeness of the estimated adjusted copy numbers to the true copy numbers illustrates the validity of this copy number estimation method by PICR.

Figure 9:
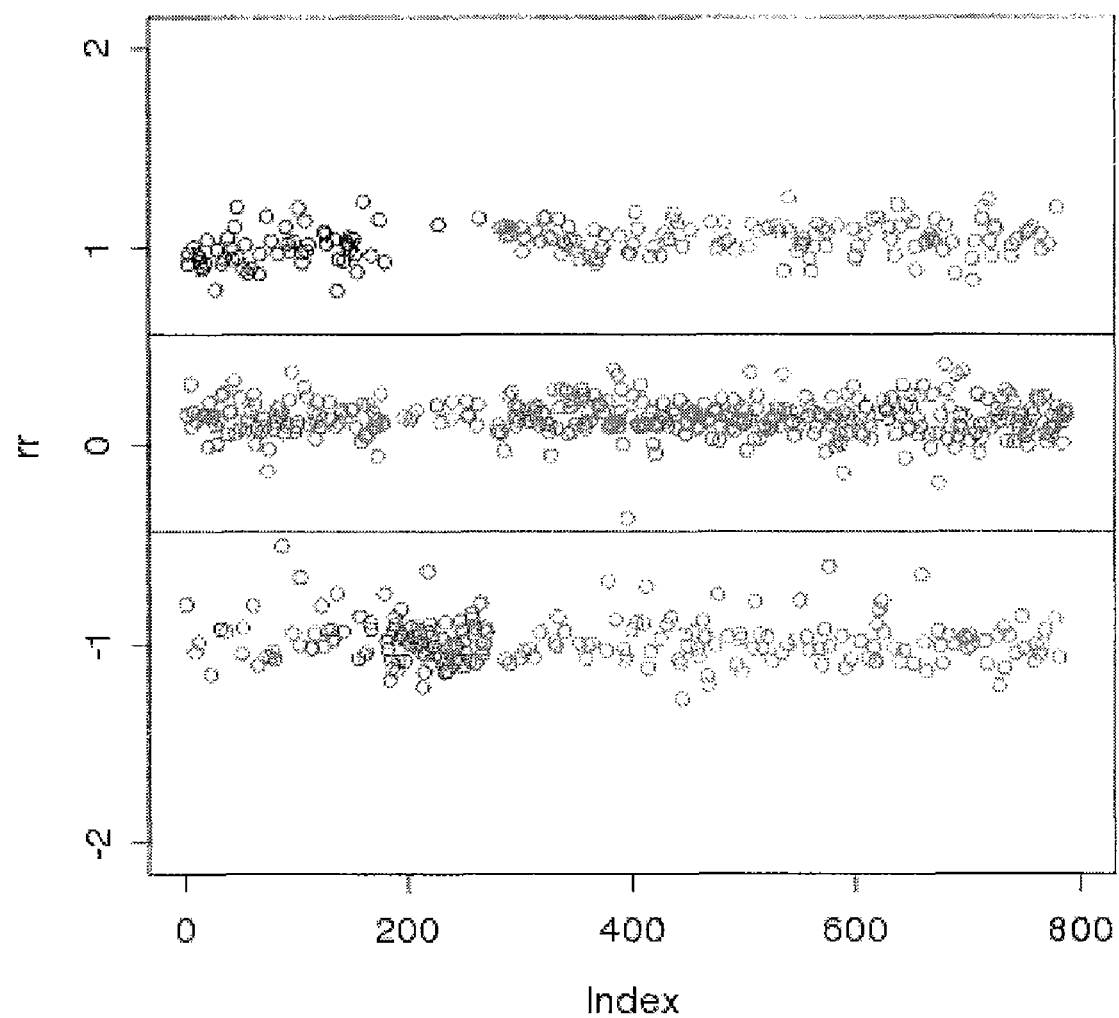

FIG. 9 presents the HapMap SNPs having 3 groups of annotated genotypes where the number of SNPs is 228,008 in the NSP array and 174,269 in the STY array. Thus, shown is one example for typical SNP achieving 3 clear clusters. "AA" SNPs in Blue; "AB" SNPs in Green; and "BB" SNPs in Red; "No call" SNPs in Black for HapMap. "Control samples" in Pink (500 control samples from Wellcome Trust data).

Figure 10A:
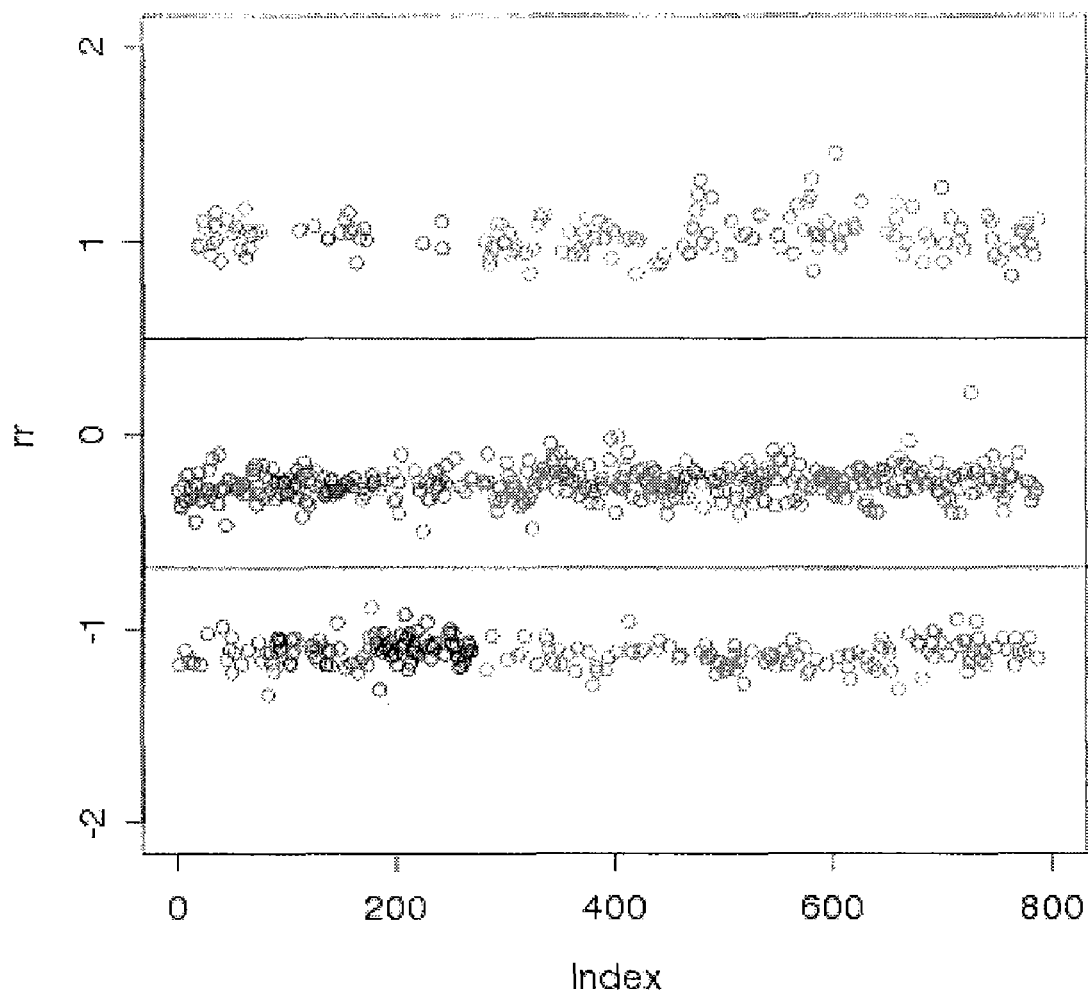
Figure 10B:
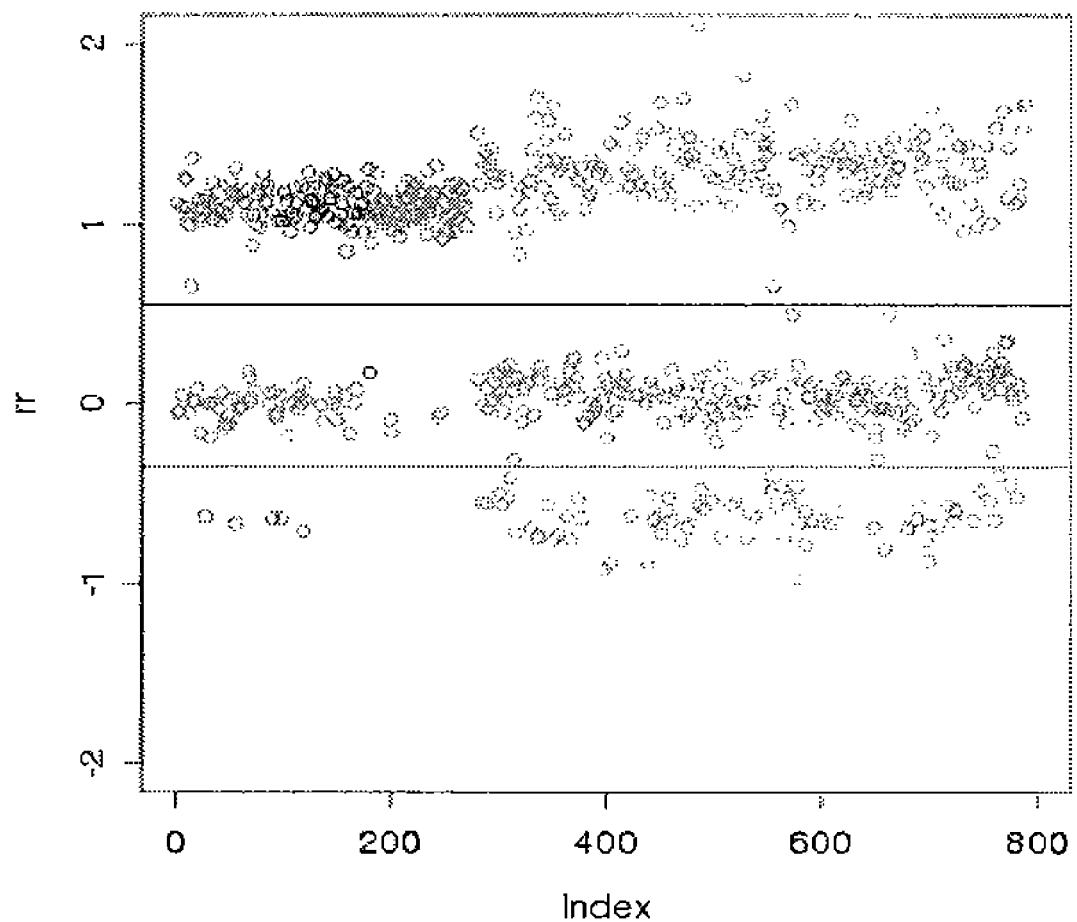

FIG. 10 presents the fix of extreme values by going over the SNPs with extreme cut-offs up to 1% from the top and 1% from the bottom (about 8.5K SNPs). FIGS. 10A and 10B present potential HapMap annotation errors or mis-labelings in the HapMap samples that may lead to poor genotype calls if not fixed. "AA" SNPs in Blue; "AB" SNPs in Green; and "BB" SNPs in Red; "No call" SNPs in Black for HapMap. "Control samples" in Pink (500 control samples from Wellcome Trust data).

Figure 11A:
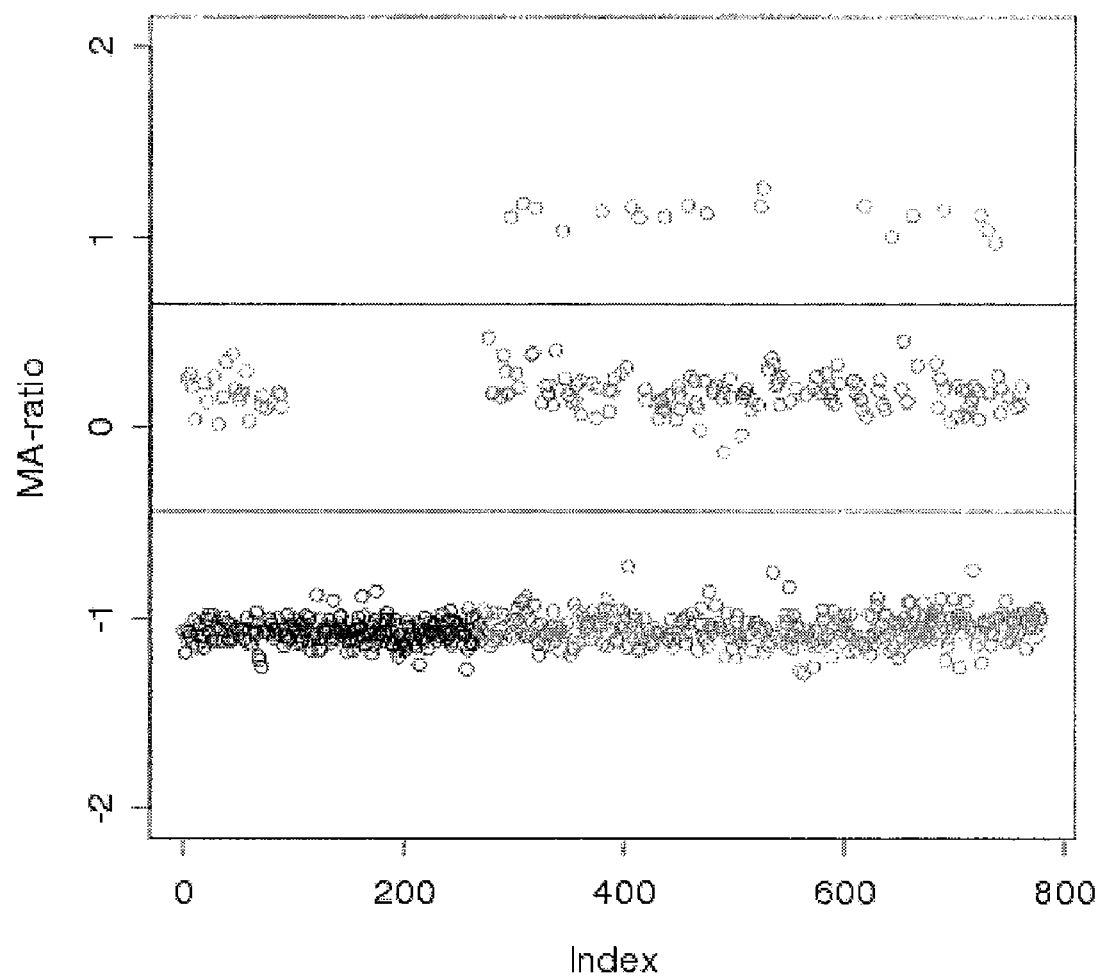
Figure 11B:
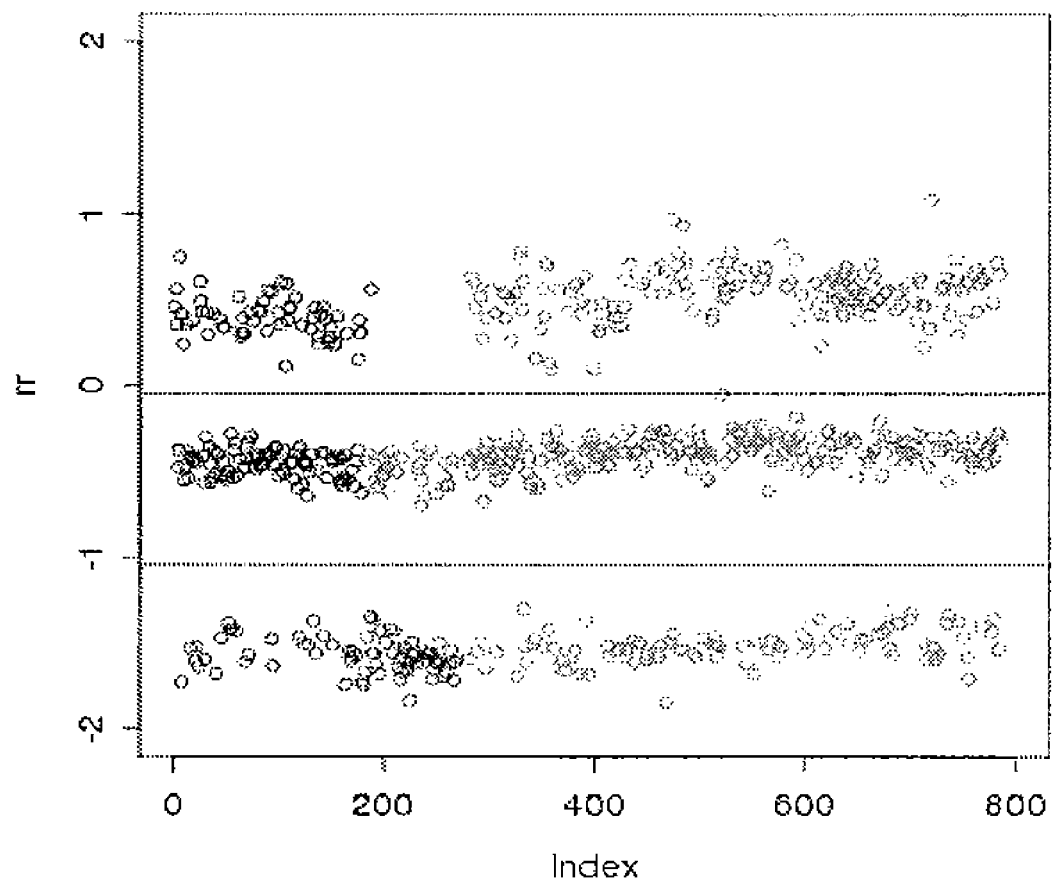
Figure 11C:
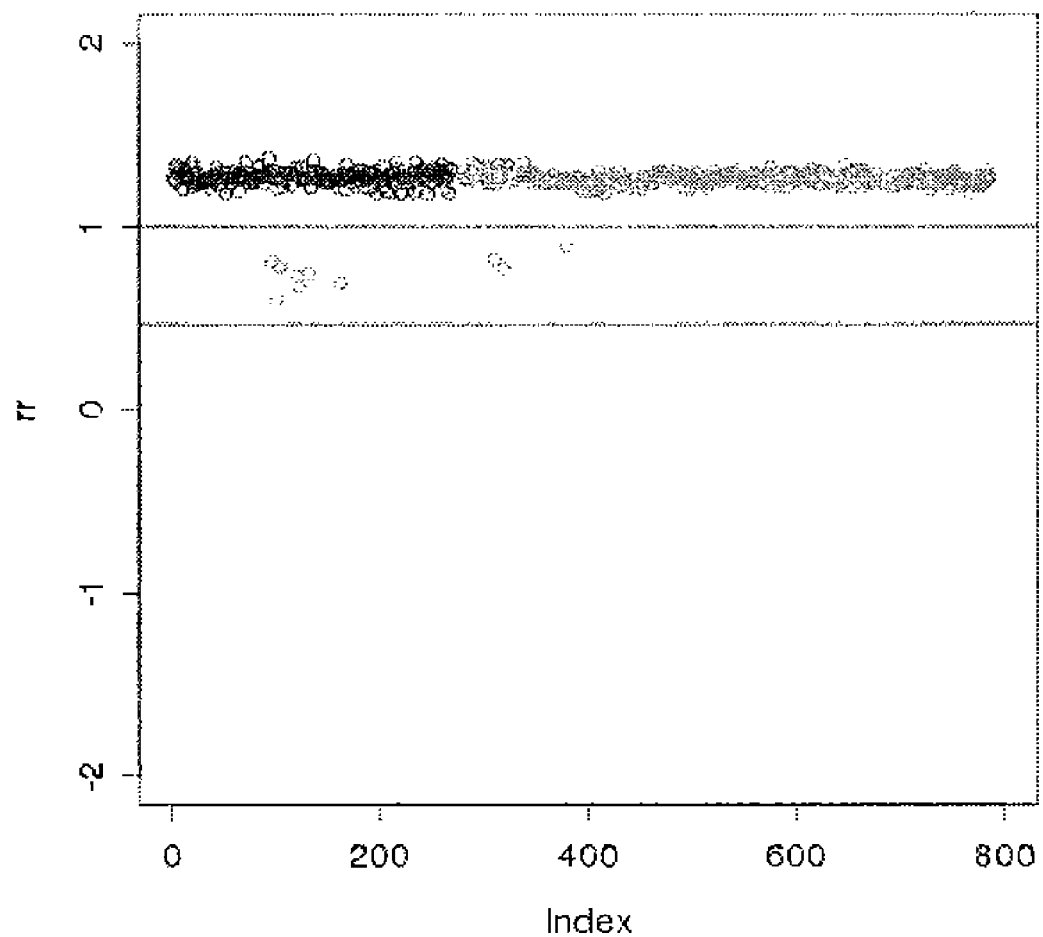
Figure 11:
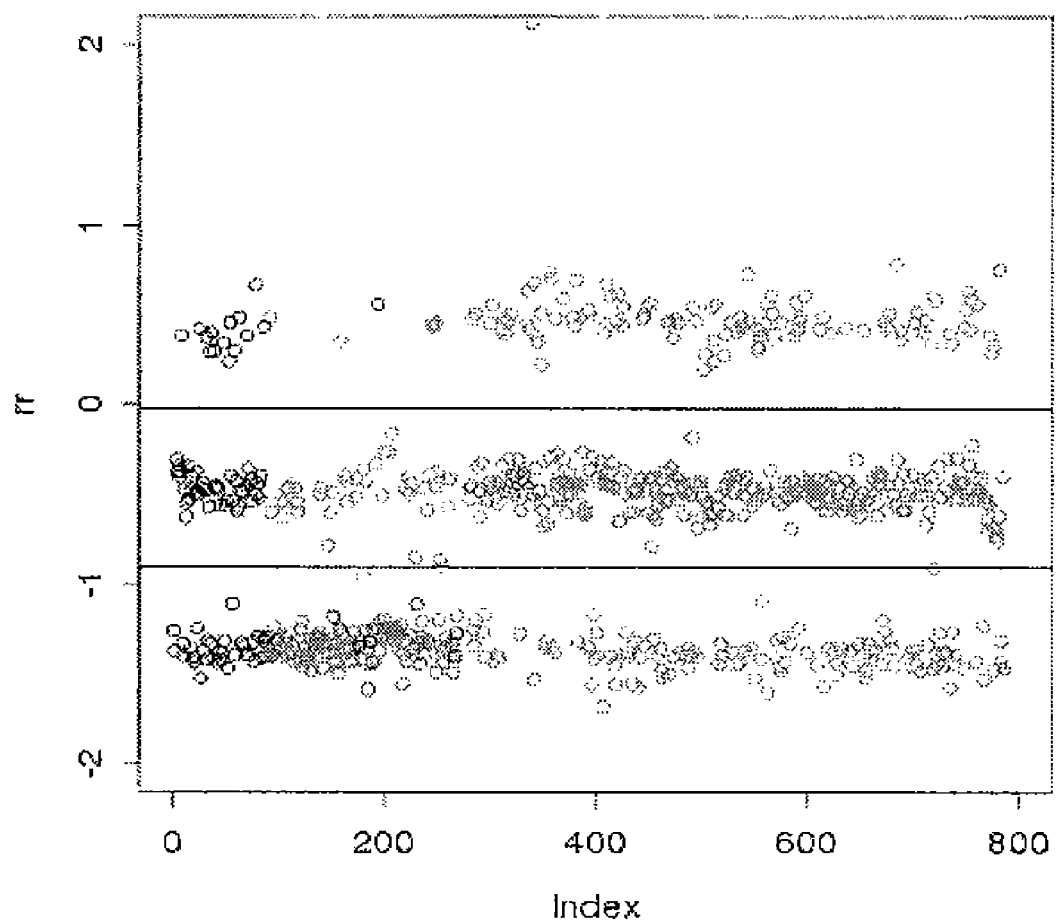

FIG. 11 presents exemplary plot data of SNPs with only 1 homozygous and 1 heterozygous annotations where the number of SNPs is 21,069 in the NSP array, and 18,402 in the STY array. FIG. 11A: additional group in WellCome Trust; FIG. 11B: the third genotype group identified that helped set up the calling criteria; FIG. 11C: no third genotype group was found; and FIG. 11D: presents a potential annotation error. "AA" SNPs in Blue; "AB" SNPs in Green; and "BB" SNPs in Red; "No call" SNPs in Black for HapMap. "Control samples" in Pink (500 control samples from Wellcome Trust data).

Figure 12A:
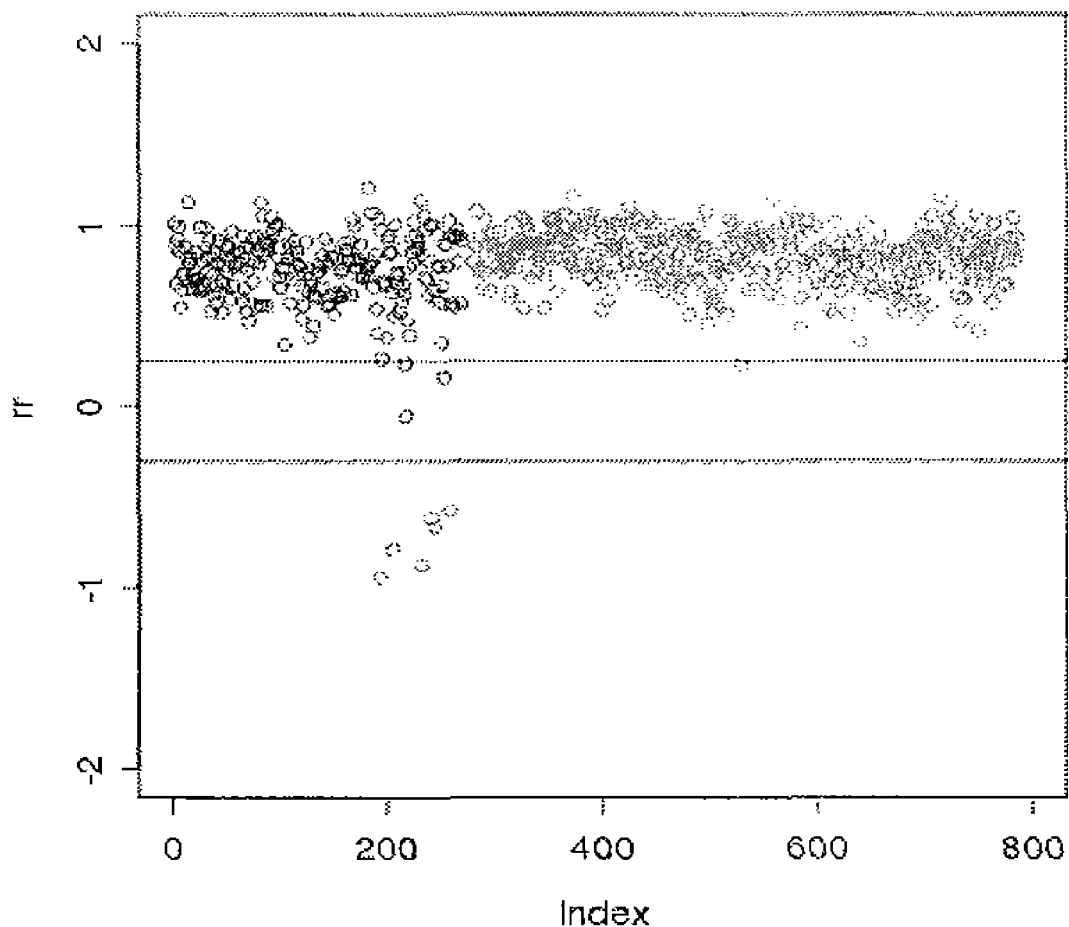
Figure 12B:
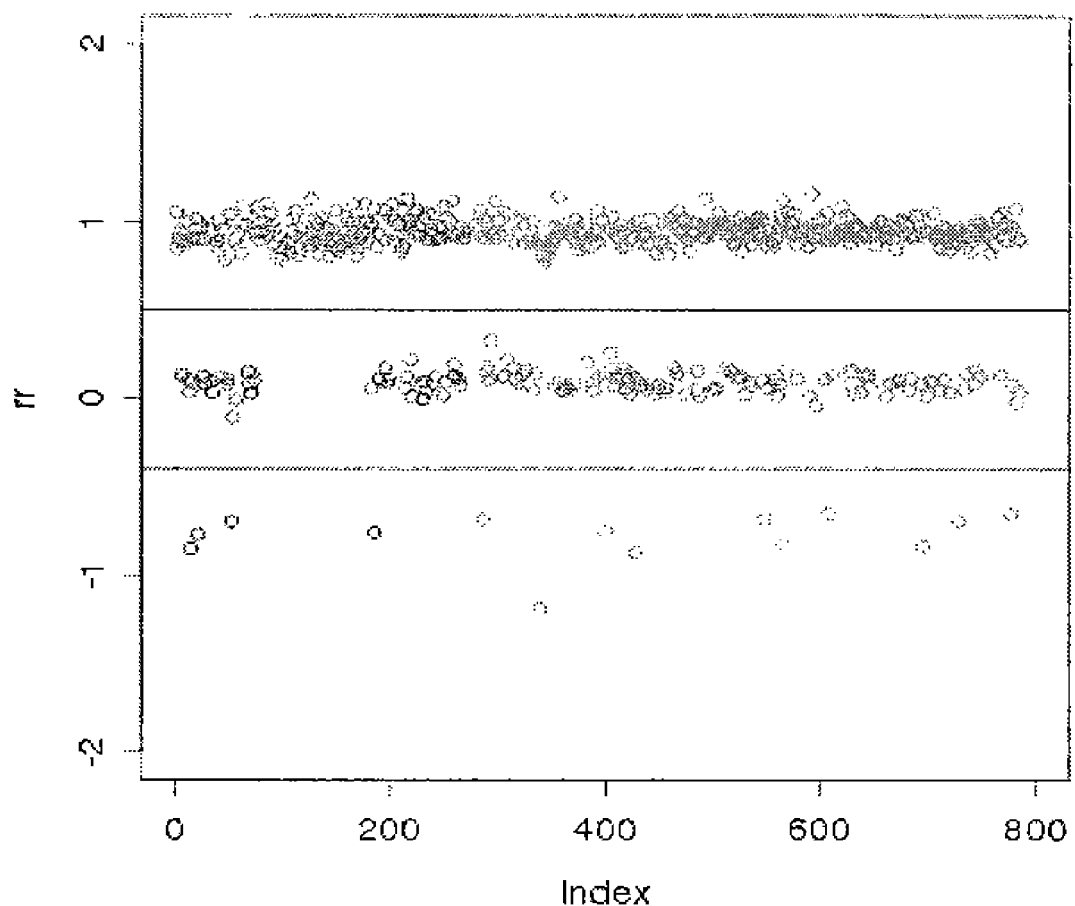

FIG. 12 presents exemplary plot data of SNPs with only 2 homozygous annotations but no heterozygous annotation where the number of SNPs is 13 in the NSP arrays and 7 in the STY arrays. FIG. 12A: presents two homozygous groups; and FIG. 12B presents potential annotation errors. "AA" SNPs in Blue; "AB" SNPs in Green; and "BB" SNPs in Red; "No call" SNPs in Black for HapMap. "Control samples" in Pink (500 control samples from Wellcome Trust data).

Figure 13A:
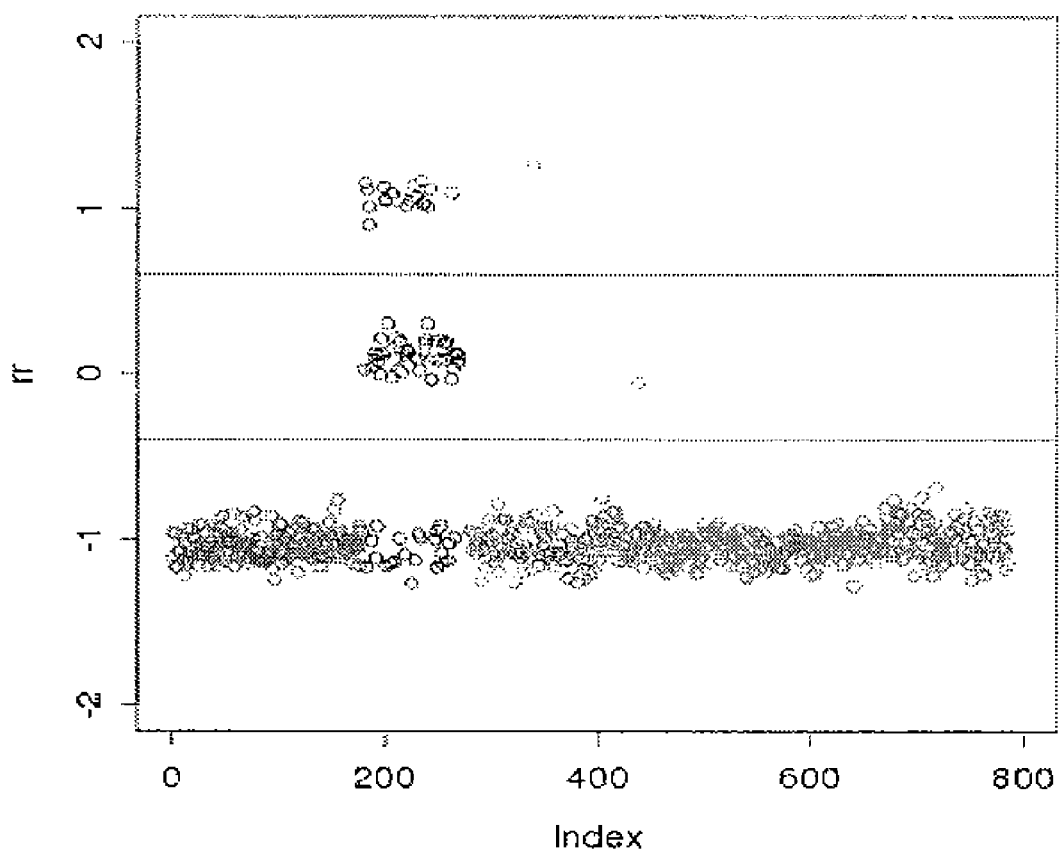
Figure 13B:
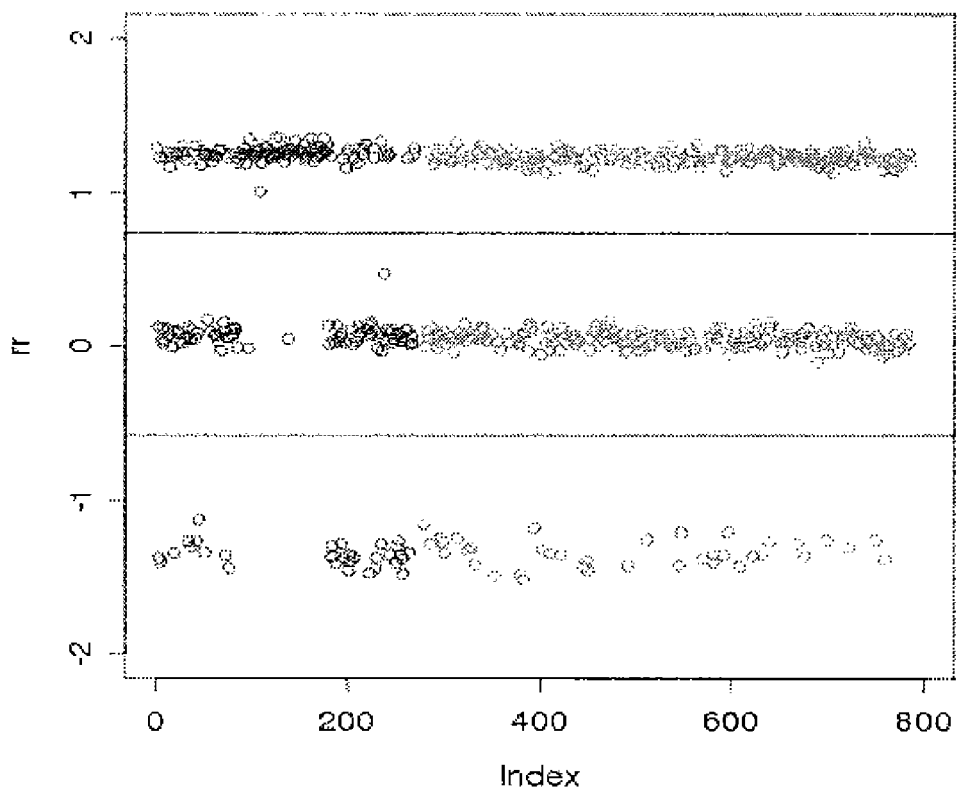

FIG. 13 presents exemplary plot data of SNPs with only 1 annotated homozygous with the number of SNPs: 232 in the NSP array and 168 in the STY array. FIG. 13A: presents three genotype groups identified; and FIG. 13B shows potential annotation errors. "AA" SNPs in Blue; "AB" SNPs in Green; and "BB" SNPs in Red; "No call" SNPs in Black for HapMap. "Control samples" in Pink (500 control samples from Wellcome Trust data).

Figure 14A:
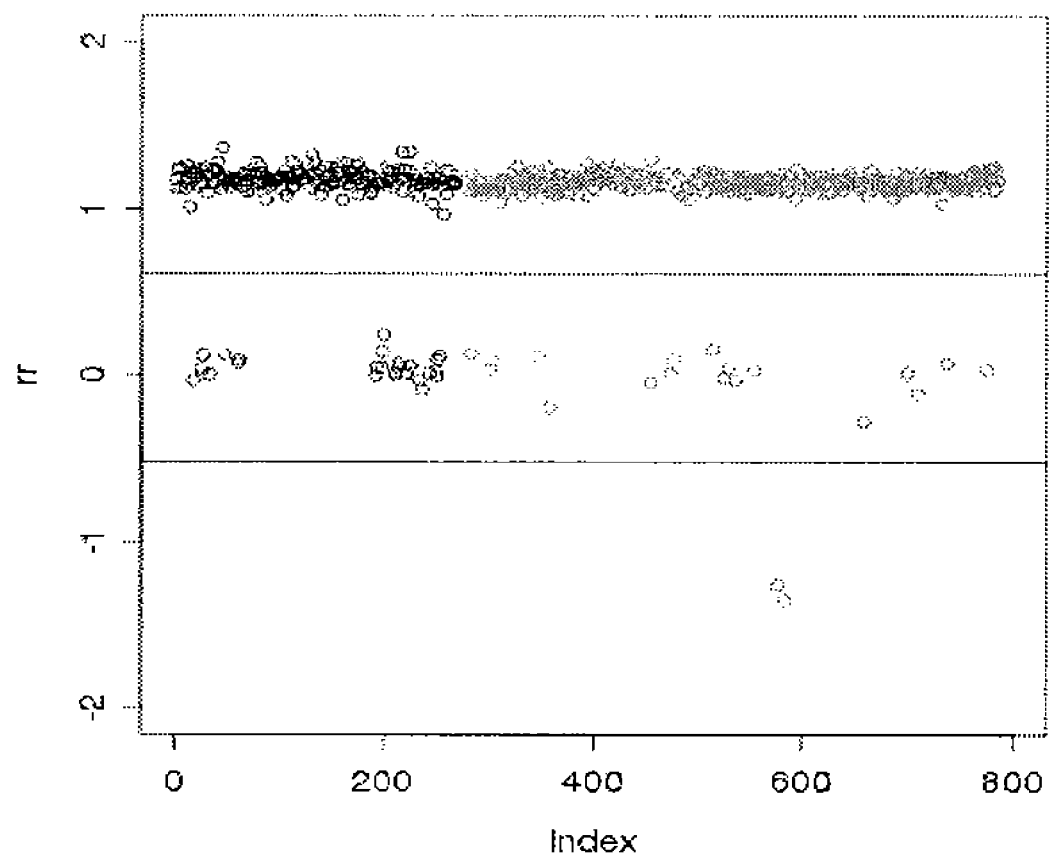
Figure 14B:
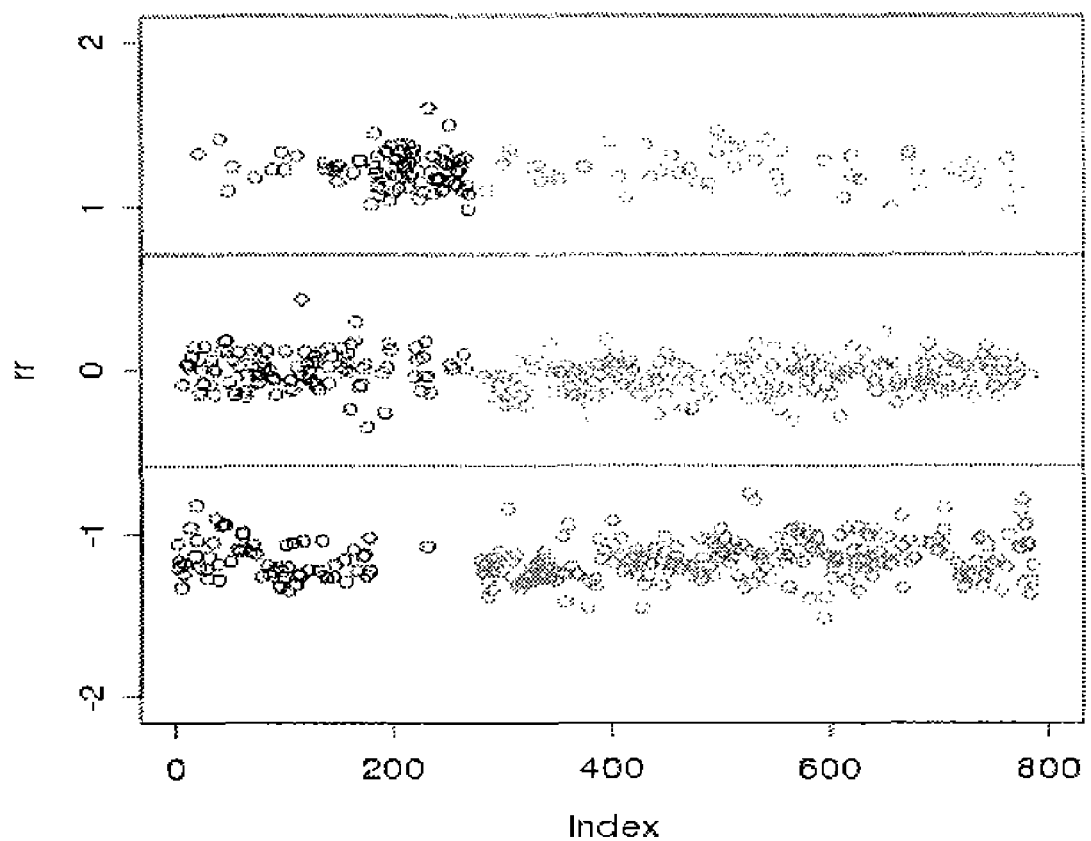

FIG. 14 presents exemplary plot data of SNPs with no HapMap annotation with the number of SNPs: 3,038 in the NSP array and 2,721 in the STY array. FIGS. 14A and 14B illustrate unsupervised learning with k-mean method after removing outliers. "AA" SNPs in Blue; "AB" SNPs in Green; and "BB" SNPs in Red; "No call" SNPs in Black for HapMap. "Control samples" in Pink (500 control samples from Wellcome Trust data).

DETAILED DESCRIPTION OF THE INVENTION

The present invention is related to methods for microarray data analysis to facilitate accurate and efficient identification of DNA copy numbers and its applications. For example, SNP genotyping can be determined based on DNA copy numbers, as well as detecting gene copy number alterations. Alternatively, gene expression analysis using RNA gene expression microarrays may also be performed by determination of gene copy numbers.

DNA abnormality, such as changes of chromosomal copy numbers, has been shown to contribute to cancer pathogenesis and other phenotypic traits. Zhao et al., "An integrated view of copy number and allelic alterations in the cancer genome using single nucleotide polymorphism arrays" *Cancer Res* 64:3060-3071 (2004); Slater et al., "High-resolution identification of chromosomal abnormalities using oligonucleotide arrays containing 116,204 SNPs" *Am J Hum Genet.* 77:709-726 (2005); and Rauch et al., "Molecular karyotyping using an SNP array for genome wide genotyping" *J. Med. Genet.* 41:916-922 (2004). Particularly, detection of DNA copy number alterations has been reported to play an important role in cancer studies. Pollack et al., "Microarray analysis reveals a major direct role of DNA copy number alteration in the transcriptional program of human breast tumors" *Proc. Nat. Acad. Sci.* 99:12963-12968 (2002); Bigness et al., "High-resolution analysis of DNA copy number using oligonucleotide microarrays" Genome Research 14:287-295 (2004); Tibshirani et al., "Spatial smoothing and hot spot detection for CGH data using the fused lasso" *Biostatistics* 2007 (in press); and Furge et al., "Detection of DNA copy number changes and oncogenic signaling abnormalities from gene expression data reveals MYC activation in high-grade palillary renal cell carcinoma" *Cancer Res.* 67:3171-3176 (2007). While DNA copy number alterations may be studied with different high throughput technologies, such as Comparative Genomic Hybridization (CGH) array, SNP arrays have received increasing attention, including applications directed towards genotyping and copy number estimation.

Determination of gene copy number is a basic concept in molecular genetics, and may help to lay a solid foundation in microarray based genomics studies. Microarray based genomics studies utilizing only proportional probe label intensities without an accurate estimation of gene copy numbers might miss the right target and lose opportunities for major discoveries. The present invention contemplates estimating gene copy numbers based on principles in physics and chemistry governing the binding of nucleotide sequences (i.e., for example, binding affinities). In one embodiment, a mathematical model utilizes probe label intensity data from both perfect match probe sequence hybridization and mismatch probe sequence hybridization. In another embodiment, the model utilizes probe sequence structure data (i.e., for example, probe binding free energy) that results in an accurate estimation and efficient computation of gene copy numbers. The model is not limited to any specific prototype or design of microarrays, and thus is applicable to large variety of microarrays (i.e., including, but not limited to SNP arrays or gene expression arrays). In one embodiment, the present invention contemplates microarrays displaying a design of labeled probes. In one embodiment, the present invention contemplates microarrays displaying a design of target oligonucleotides comprising at least a portion of a gene allele.

Although it is not necessary to understand the mechanism of an invention, it is believed that the present modeling method creates advantages in relation to other current methods. Xiao et al., "A multi-array multi-SNP genotyping algorithm for Affymetrix SNP microarrays" *Bioinformatics*, 23:1459-1467 (2007); and Laframboise et al., "Allele-specific amplification in cancer revealed by SNP array analysis" *PLoS Computational Biology*, 1:e65 (2005). It is further believed that any methods solely based on statistical methodologies without including probe sequence structure information will not result in an accurate determination of gene copy number. Further, it is believed that any methods solely based on the study of probe sequence structure information without a proper implementation through mathematical and statistical models will also not result in an accurate determination of gene copy number.

In one embodiment, the present invention contemplates comprehensive statistical analyses including, but not limited to, linear regression coupled with an improved calculation of a fixed effect or mean of random effects. Rauch et al., "Molecular karyotyping using an SNP array for genome wide genotyping" *J. Med. Genet.* 41:916-922 (2004); and Pollack et al., "Microarray analysis reveals a major direct role of DNA copy number alteration in the transcriptional program of human breast tumors" *Proc. Nat. Acad. Sci.* 99:12963-12968 (2002), respectively. Alternatively, other statistical methods can also solve linear regression models, including, but not limited to, linear mixed effects model, analysis of variance (ANOVA) model, Bayesian methods, or Lasso shrinkage methods.

I. Gene Copy Number Estimation

In one embodiment, the present invention contemplates a statistical model that provides an efficient computational method to implement an estimation of copy numbers selected from a total of approximately $4^{25} > 1.125 \times 10^{12}$ possible permutations (combinations with different ordering of linear nucleotide sequences) using individual labeled probes consisting of 25-mers (i.e., for example, twenty-five nucleotides of A, C, G and T in different linear orders).

A. Label Intensity Microarray Techniques

Estimation of gene copy numbers has not been successful in the past due to several technical limitations. Such limitations include, but are not limited to: i) dependence upon a positive logarithmic scale correlation between perfect match probe intensities and gene copy number; and ii) the use of data driven ad hoc approaches that lack theoretical support in biology, chemistry, and physics. These approaches fail to address how mismatch probe sequence data affect the relationship between probe label intensity data and gene copy number. Not using mismatch sequence data makes it difficult, if not impossible, to obtain an unbiased estimation (i.e., for example an accurate determination) of gene copy numbers. Although it is not necessary to understand the mechanism of an invention, it is believed that mismatch probe sequences contain information relevant to SNP genotyping and differentiation of gene expression, which is not available when analyzing only perfect match sequence data. Xiao et al., "A multi-array multi-SNP genotyping algorithm for Affymetrix SNP microarrays" *Bioinformatics*, 23:1459-1467 (2007). Until the present invention, mismatch probe sequence data was relatively ignored because there was a lack of mathematical models to reveal the full usefulness of mismatch probe sequence intensity data, to quantitatively characterize probe intensity utilizing both gene copy number and probe binding affinity capable of incorporating both perfect match sequence and mismatch sequence information. In some embodiments, the present invention solves these problems.

Other current methods used for SNP genotyping have limited applicability because they are sample-dependent as well as array prototype dependent. For example, when using these current methods, the determination of a SNP genotype of each individual subject depends on data from other individuals collected from the same DNA locus (i.e., the same position on the genome). Alternatively, the determination of SNP genotype must be collected under identical microarray configurations (i.e., for example, type of microarray and experimental conditions). Thus, when using current techniques, the resulting individual SNP genotype varies when determined from data of multiple subjects. This variability is observed even though each microarray contains the necessary and sufficient information to consistently determine the same SNP genotype from a given subject. Since different microarray prototypes (i.e., for example, 10K, 100K, and 500K SNP microarrays) are known to have different distributions of probe label intensity, adjustments must be made in the gene copy number determination method when data from two or more different microarrays are compared. Further, the recently introduced 1000K SNP microarrays (i.e., for example, Affymetrix, Inc.) will require further adjustments when using these currently used sample/array dependent methods. These adjustments are in addition to previous adjustments that allow comparison of data from 100K arrays to 500K arrays.

B. Copy Number Microarray Techniques

The present invention contemplates a method to determine gene copy number and its applications including, but not limited to, the determination of a SNP genotype. In one embodiment, the method comprises integrating both perfect match probe sequence data and mismatch probe sequence data with calculated probe binding affinity data.

In one embodiment, the present invention contemplates a method to estimate gene copy number using oligonucleotide arrays in such a manner that actual gene copy number is accurately determined. Although it is not necessary to understand the mechanism of an invention, it is believed that this method allows inference to be based on the copy numbers rather than on probe label intensities, thereby positioning further studies to evaluate the correct sequence target with improved accuracy. It is further believed that this improved accuracy is based on the fact that the gene copy numbers can be estimated by filtering out large scale errors inherent in current microarray techniques limited to measuring only probe label intensity.

In one embodiment, the present invention contemplates a method to characterize the label intensities of both perfect match probe sequences and mismatch probe sequences. In one embodiment, the method further comprises gene copy numbers, probe binding affinities, and the free energy of nucleotide sequences. It is further believed that this method improves upon methods that only consider probe label intensities using perfect match probe sequence data, and invalidates the current belief that gene copy numbers are proportional only to perfect match probe sequence intensity and ignores mismatch probe sequence intensity data by assuming such data does not provide any useful information except for background control data.

In one embodiment, the present invention contemplates a system of models to calculate gene copy numbers of target sequences (i.e., for example, an oligonucleotide sequence). In one embodiment, the models utilize fluorescence probe data. In one embodiment, the probe data is collected from perfect match probe sequences. In one embodiment, the probe data is collected from mismatch probe sequences. In one embodiment, the gene copy number is accurately determined by using a statistical linear regression model. In one embodiment, the regression model meets a desired confidence level. In one embodiment, the regression model provides estimation method with no bias.

In one embodiment, the present invention contemplates a statistical method that models all possible oligonucleotide probe sequence permutations (i.e., for example, approximately $4^{25}$, which is greater than $1.125 \times 10^{15}$). In one embodiment, the method comprises parameters based on data collected from perfect match probe sequences and mismatch probe sequences. In one embodiment, the method utilizes probe pairs directed to consecutive nucleotides to assess perfect match probe sequences. In one embodiment, the perfect match assessment comprises sixteen (16) nucleotide pair parameters. In one embodiment, the perfect match assessment comprises twenty four (24) nucleotide pair parameters. In one embodiment, the mismatch probe assessment comprises one hundred and ninety two (192) nucleotide triplets (three-tuples). Although it is not necessary to understand the mechanism of an invention, it is believed that the total number of parameters (i.e., for example, approximately two thousand or less; $\leq 2000$) is dramatically smaller than the originally projected $1.125 \times 10^{15}$ model parameters thereby making the computations efficient and fast.

In one embodiment, the model system comprises a statistical technique using a statistical model to determine free energy binding of short nucleotide sequences (i.e., for example, pair-wise (i.e., for example, perfect match probes) or triplet sequences (i.e., for example, three-tuple mismatch probes)). In one embodiment, the statistical technique is compatible with conditions evaluating k-tuples for both perfect matches and mismatches, wherein k>3. Although it is not necessary to understand the mechanism of an invention, it is believed that this model system is not only easy to implement by using a relatively small number of parameters that accurately estimate the binding free energy and affinity, but also efficiently carries out the computation to determine an accurate gene copy number estimation. It is further believed that the contemplated system avoids the current consequences that where the number of model parameters increases with k, the resulting large number of parameters will not be computationally efficient. In one embodiment, the present statistical technique utilizing pair-wise nucleotides for perfect matches and triplet (three-tuple) nucleotides for mismatches achieves accurate estimations of gene copy numbers and SNP genotype determinations.

The present invention estimates model parameters based on the probe sequence structure, rather than the distribution of probe intensities. Consequently, the present method of estimating gene copy numbers is accurate when using any microarray prototype including, but not limited to, a 100K, a 500K, or a 1000K SNP microarray. Further, the present method of estimating gene copy number is accurate when using microarrays having different designs, for example: i) probes having a different number of nucleotides; ii) arrays having unequal numbers of perfect matches and mismatches for each SNP probe; or iii) arrays having probes containing only perfect match or mismatch sequences. In one embodiment, the present invention contemplates that model parameters estimated from one SNP array can be also applied to other microarrays of the same, or different, prototype and achieve the same accuracy for copy number estimation. Data presented herein demonstrate that model parameters based on the pair-wise perfect match probes and triplet (i.e., for example, three-tuples) mismatch probes remain the same for different 25-mer arrays. However, it is expected that microarrays designed to: i) use a smaller number of probes for each SNPs; ii) use only perfect match probes; or iii) use only mismatch probes will not achieve the same accuracy for copy number estimation due to a foreseeable information loss.

In one embodiment, the present invention contemplates a method using SNP microarrays (i.e., for example, Affymetrix) to detect and determine gene copy numbers (i.e., for example, deoxyribonucleic acid gene copy numbers). In another embodiment, the present invention contemplates a method using RNA gene expression arrays to identify differentially expressed genes through accurately determining gene copy numbers. Although it is not necessary to understand the mechanism of an invention, it is believed that a RNA gene expression microarray displays oligonucleotides comprising genes capable of binding multiple oligonucleotide sequence probes (i.e., for example, perfect match probes and mismatch probes), thereby making the presently described method useful in accurately estimating the gene copy number on the RNA gene expression microarrays. It is further believed that the present method achieves higher consistency and higher reproducibility than traditional methods by estimating gene copy numbers rather than a simple reliance on probe label intensity proportionality.

II. Microarray Technology

Microarray technology generally utilizes contacting thousands of oligonucleotide probes (i.e., for example, perfect match probes) with arrayed oligonucleotides having target nucleotide sequence. Alternatively, microarray technology may also contact target oligonucleotides (i.e., for example, those provided from a biological sample) with an array designed with thousands of probes on each array.

In one embodiment, the present invention contemplates a probe nucleotide sequence affixed to a microarray comprising, for example, twenty-five (25) nucleotides (i.e., for example a 25-mer). Alternatively, microarray technology has developed microarrays displaying oligonucleotides comprising SNPs and or oligonucleotides comprising genes capable of RNA expression. Both types of microarrays are similar in design and work in a similar way, wherein each arrayed oligonucleotide comprises at least one gene capable of hybridizing with a plurality of probes. Each probe-gene interaction (i.e., for example, contacting) may comprise either perfect match sequence hybridizations (i.e., complete identity between probe and target nucleotide sequence) and/or mismatch pair hybridizations (i.e., for example, partial identity between probe and target nucleotide sequence). Usually, each probe is designed for identifying one SNP at a specific genomic locus (genomic position) with a predetermined SNP type comprising two alleles (i.e., for example, a GC SNP or an AT SNP).

For notational convenience, a hypothetical "AB SNP" denotes two alleles A and B (i.e., for example, individuals having either a locus genotype AA, AB, or BB). To annotate this hypothetical SNP for each individual subject, two probe pairs (four probes) are designed to interrogate the target sequence through DNA/DNA hybridization. Among these four probes, a first probe pair interrogates allele A and a second probe pair interrogates for allele B. Within each probe pair, a first probe sequence is designed for a perfect match (i.e., for example, a perfect match probe), while a second probe sequence is designed for a mismatch (i.e., for example, a mismatch probe), wherein the mismatch nucleotide hybridization occurs at the target sequence. Hence, these four probe sequences are labeled as perfect match A (PA), mismatch A (MA), perfect match B (PB), and mismatch B (MB). Matsuzaki et al., "Genotyping over 100,000 SNPs on a pair of oligonucleotide arrays" Nature Methods 1:109-111 (2004). See, FIG. 1A.

Furthermore, the perfect match probe sequences and mismatch probe sequences are designed to interrogate the target sequence at the locus with a different shift of nucleotide position relative to the central nucleotide of the probe (i.e., for example, position 13 within a 25-mer probe). Generally, each nucleotide position shift interrogation comprises a sense-strand and/or antisense strand-set of PA, MA, PB and MB (i.e., for example, a probe quartet). This interrogation procedure is usually repeated at numerous positions (l) for each probe sequence to ensure quality control and accuracy (i.e., for example, l=10 for 50K and 100K SNP arrays; l=6 for 500K SNP arrays). Thus, a microarray analysis utilizes l quartets for each probe, with a total of 4l probe sequences. The total 4l probe label intensities (i.e., for example, 2l perfect match probe intensities and 2l mismatch probe intensities) may be used to determine SNP genotype and/or DNA copy numbers for one individual at a specific genomic locus.

Although some believe that current genotype calling methods have a calling rate around 99.5% with a 0.3% type I error rate; the availability of more complex microarrays, such as the most recent 500K and 1000K SNP microarrays, pose challenges to maintain this calling rate because of the following reasons: i) new microarray designs (i.e., for example, Affymetrix arrays) preferentially select first those SNPs relatively easy to genotype by using low density arrays (i.e., for example, 10K to 100K arrays), thereby leaving SNPs difficult to genotype to be determined using high density arrays (i.e., for example, 500K and 1000K arrays) (Rabbee et al., "A genotype calling algorithm for Affymetrix SNP arrays" Bioinformaties 22:7-12 (2006); ii) for the high density SNP arrays currently used, genotype calling methods may have 5,000 SNPs that cannot be called on each 1000K SNP array, thereby resulting in about 7,000 additional SNPs to be incorrectly genotyped. This is certainly at a highly unsatisfactory level for genome-wide study with millions of SNPs involved and thus improvement is urgently needed.

Microarrays may be custom constructed for specific purposes or they may be purchased (pre-made) from commercial vendors. One such vendor is Affymetrix. Affymetrix Inc. has several prototypes of SNP arrays, e.g., 10K, 100K, 500K and 1000K arrays. The 100K array design consists of a paired 50K Xba array and a 50K Hind array. The 100K array is designed to use ten (10) probe quartets to interrogate a single dimorphic SNP site (i.e., for example, alleles A and B). Each probe quartet consists of 2 pairs (perfect match and mismatch pair) of probes, one for allele A and the other for allele B. Each probe has one 25-mer nucleotide sequence designed to either perfectly match or mismatch the nucleotide at the SNP position to the target sequence. These 10 quartets are designed to take different shifts (k) of nucleotide on the probe sequence (i.e., for example, k may take a value of −7, −6, −5, −4, −3, −2, −1, 0, 1, 2, 3, 4, 5, 6, 7; wherein k=0 corresponds to the center nucleotide at position 13 of the 25-mer) surrounding the center of the probe sequence and may also take sense or anti-sense strand. Matsuzaki et al., "Parallel genotyping of over 100,000 SNPs using a one-primer assay on a high-density oligonucleotide array" Genome Research 14:414-425 (2004). Mismatch probes may have two mismatches, one sure mismatch at a center nucleotide (k=0) to the target sequence, and one potential mismatch at a shift position (k≠0) depending on the SNP genotype of the target sequence.

Several current methods for estimating gene copy number have been developed for SNP arrays. Generally, these methods are dependent upon a positive correlation between probe intensity on a logarithmic scale. For example, the CNAG method assumes that the gene copy number may be modeled through a log ratio of two observed sample signals adjusted with two additive quadratic polynomials, one of the length of the target sequence and the other of the GC content. Nannya et al., "A robust algorithm for copy number detection using high-density oligonucleotide single nucleotide polymorphism genotyping array" Cancer Res 65:6071-6079 (2005). Similarly, the CARAT method assumes that the logarithm of the copy number is proportional to the logarithm of the probe intensity, which leads to an model to determine the copy number through the SNP genotypes and intensity. Huang et al., "CARAT: a novel method for allelic detection of DNA copy number changes using high density oligonucleotide arrays" BMC Bioinformatics, 7:83 (2006). Also, the PLASQ method is based on a generalized linear model that interrogated probe intensities accounting for probe sequence structure with up to one mismatch in nucleotide hybridization. Laframboise et al., "PLASQ: a generalized linear model-based procedure to determine allelic dosage in cancer cells from SNP array data" Biostatistics 8:323-336 (2007).

Following the availability of SNP array technology, genotyping methods using whole genome sampling assay and dynamic modeling (DM) algorithms were developed. Kennedy et al., "Large-scale genotyping of complex DNA" Nature Biotechnology 21:1233-1237 (2003); Liu et al., "Algorithms for large-scale genotyping microarrays" Bioinformatics 19:2397-2403 (2003); and Di et al., "Dynamic model based algorithms for screening and genotyping over 100 K SNPs on oligonucleotide microarrays" Bioinformatics 21:1958-1963 (2005). These algorithms use single array information, but later improvements allowed the use of multiple array methods. For example, the RLMM method takes a multiple array supervised learning approach and simultaneously annotates thousands of SNPs based on large training data. Rabbee et al., "A genotype calling algorithm for Affymetrix SNP arrays" Bioinformatics 22:7-12 (2006). The BRLMM method relies on DM calls and Bayesian computation for supervised learning, and requires a moderate number of arrays for model training. Affymetrix Inc., "BRLMM: an improved genotype calling method for the GeneChip human mapping 500K array set" (2006). The CRLMM method first preprocesses data with target sequence information, including sequence length and GC content, through a regression model before adopting the supervised learning. Carvalho et al., "Exploration, normalization, and genotype calls of high-density oligonucleotide SNP array data" *Biostatistics* 8:485-499 (2007). In contrast, a GEL single array method, taking an empirical Bayes approach and weighting on the probes for each SNP annotation, achieved comparable accuracy in genotyping in terms of call rate and error rate. Nicolae et al., "GEL: a novel genotype calling algorithm using empirical likelihood" *Bioinformatics* 22:1942-1947 (2006). Although several methods were claimed to yield a high accuracy with low no call rate (1%) and low error rate (0.3%), they may still make more than 3,000 to 10,000 incorrect genotype calls on each array of the most recently launched 1000K SNP arrays at such accuracy. The fast advancement of technologies and genome-wide association studies involving millions of SNPs demand robust models and methods with improved accuracy.

III. Generalized Positional-Dependent Nearest Neighbor (GPDNN) Statistical Modeling The present invention contemplates methods for estimating gene copy number that does not depend on fluorescence probe intensity proportionality as a starting point. In one embodiment, an accurate estimation of gene copy numbers utilizes modeling of probe label intensity because probe intensity is one parameter can be directly measured through fluorescence scan. To provide an accurate statistical model to evaluate the probe intensity a GPDNN model was developed. Although it is not necessary to understand the mechanism of an invention, it is believed that a GPDNN statistical model utilizes principles in physics and chemistry that governs nucleotide binding affinities through binding free energy of nucleotide sequences.

Based on an understanding of probe binding mechanisms, the present invention contemplates modifying currently used PDNN models (utilized for processing only perfect match probe data), into a Generalized PDNN model (GPDNN) capable of incorporating data from both perfect match probes and mismatch probes. In one embodiment, the GPDNN model provides formulae for probe binding free energies. In one embodiment, the binding free energy formula contemplates no mismatch probe binding. In one embodiment, the binding free energy formula contemplates one mismatch probe binding. In one embodiment, the binding free energy formula contemplates two mismatch probe binding. In another embodiment, the GPDNN model further provides models for probe intensities with allelic copy numbers and binding affinity of probe sequences based on Langmuir adsorption to accommodate both perfect match data and mismatch data. In one embodiment, the model provides unbiased estimation of allelic copy numbers.

In one embodiment, the present invention contemplates a method for SNP genotype calling, wherein the method is based upon a gene copy number estimation. Although it is not necessary to understand the mechanism of an invention, it is believed that when compared with currently available methods, this method yields an accurate call rate and a zero no call. It is also believed that the contemplated method possesses the following advantages: i) it extends the PDNN model and characterizes the intensities at both perfect match and mismatch probes through modeling probe sequence structure; ii) it provides a model for probe intensities with allelic copy numbers and sequence binding affinity; iii) it allows unbiased estimation of copy numbers through a statistical regression model and makes it feasible to estimate the copy numbers with assessment of accuracy; iv) it utilizes probe-specific sequence structure, thus provides richer information and more accurate results than utilizing only summary sequence information, such as target sequence length and GC content; v) it is based on a single array approach, does not rely on either large training data of multiple arrays, array prototype (100K or 500K), or distribution of array intensities, and provides robust modeling and estimation.

In one embodiment, the presently contemplated statistical model to determine gene copy number alteration includes parameters comprising perfect match probe label intensity data, mismatch probe fluorescence data, probe binding affinity, gene copy number estimations, and probe sequence structure of both perfect match probes and/or mismatch probes.

The following describes an exemplary step-by-step procedure to illustrate how the probe intensity is modeled to calculate gene copy numbers. Although an Affymetrix 100K SNP array of 25-mer probe sequence is used for this illustration, this example should not be considered as limiting the present invention to only 100K SNP arrays, nor is the present invention limited to 25-mer probe sequences.

Let $(PA^k, MA^k, PB^k, MB^k)$ denote a quartet of perfect match probe A, mismatch probe A, perfect match probe B and mismatch probe B, with a nucleotide shift k; i.e., the SNP site is at the position 13+k of the 25-mer probe sequence. Note that 13 is the center position of a 25-mer probe sequence.

A. Binding Free Energies of Perfect Match Hybridizations

The positional-dependent nearest neighbor (PDNN) model expresses the binding free energy of a perfect match hybridization to the probe $PA^k$. Zhang et al., "A model of molecular interactions on short oligonucleotide microarrays" *Nature Biotechnology* 21:818-821 (2003); and Zhang et al., "Free energy of DNA duplex formation on short oligonucleotide microarrays" Nucleic Acids Res, 2007, 35, e18. For example:

$$E_A^{S^{PA^k}}(S^{TA^k}) = \sum_{p=1}^{24} \omega_p \lambda(b_p^{SPA}, b_{p+1}^{SPA}) \quad (1)$$

where $$S^{PA^k} = (b_1^{S^{PA^k}}, b_2^{S^{PA^k}}, \ldots b_{25}^{S^{PA^k}})$$

is the 25-mer probe sequences of $PA^k$, and $S^{TA^k}$ is the target sequence, and $\omega_p$ is a position weight that depends on the position of consecutive bases along the 25-mer oligonucleotide sequence, and $\lambda$ represents a stacking energy of the nearest neighbor nucleotide pair along the nucleotide probe sequence. There are a total of sixteen (16) nucleotide pairs at twenty-four (24) different positions.

B. Binding Free Energies of Mismatch Hybridizations

To model binding free energies of mismatch probes to target sequences, the PDNN model can be generalized by adding at least one mismatch free energy term to develop a modified GPDNN model, for example:

1. One unique mismatch between probe and corresponding target sequence with a shift of interrogating nucleotide at the (13+k)-th position of probe sequence, the binding free energy may be represented by:

$$E_1^{S_p^k}(S_t^k) = \sum_{\substack{l=1 \\ l \neq 12+k', 13+k'}}^{24} \theta_l^k \lambda(b_l^{S_p^k}, b_{l+1}^{S_p^k}) + \delta^k \left( \begin{array}{c} \{b_{12+k'}^{S_p^k}, b_{13+k'}^{S_p^k}, b_{14+k'}^{S_p^k}\}, \\ \{b_{12+k'}^{S_t^k}, b_{13+k'}^{S_t^k}, b_{14+k'}^{S_t^k}\} \end{array} \right) \quad (2)$$

where $S_p^k$ and $S_t^k$ are the probe sequence and binding target sequence with shift k, respectively. $b_l^{S_p^k}$ and $b_l^{S_t^k}$ are the l-th nucleotide on them, respectively. $\theta_l^k$ is a positional weight for perfect match similar to $\omega_p$ in model (1). Index k'=0 or k for mismatch either at position 13 or at (13+k), respectively. $\delta^k$ represents the binding free energy of the tri-nucleotides at position {12+k', 13+k', 14+k'}; centering at the mismatch position (13+k'). $\kappa^{k'}$ is a positional weight for mismatch nucleotide triplet with the mismatch nucleotide at position 13+k'. Index k'=0 or k for mismatch nucleotide either at position 13 or 13+k, depending on the shift, probe type and target SNP genotype. There are a number of cases where k'=0 or k. A few examples to illustrate typical cases are as follows.

Example 1. k=0. MA probe of interrogating quartet at center position 13 has one mismatch at position 13, thus k'=0.

Example 2. k≠0. MA probe of interrogating quartet at position 13+k has one mismatch at center position to target sequence of allele A, thus k'=0.

Example 3. k≠0. PA probe of interrogating quartet at position 13+k has one mismatch at position (13+k) to target sequence of allele B, thus k'=k.

2. Two mismatches at positions 13 and (13+k) with k≠0 (e.g. MA probes at position 13+k have two mismatches to target sequence of allele B).

$$E_2^{S_p^k}(S_t^k) = \sum_{\substack{l=1 \\ l \neq 12,13,12+k,13+k}}^{24} \theta_l^k \lambda(b_l^{S_p^k}, b_{l+1}^{S_p^k}) + \quad (3)$$

$$\delta^0 \left( \begin{array}{c} \{b_{12}^{s_0}, b_{13}^{s_0}, b_{14}^{s_0}\}, \\ \{b_{12}^{s_t^0}, b_{13}^{s_t^0}, b_{14}^{s_t^0}\} \end{array} \right) + \delta^k \left( \begin{array}{c} \{b_{12+k}^{s_p^k}, b_{13+k}^{s_p^k}, b_{14+k}^{s_p^k}\}, \\ \{b_{12+k}^{s_t^k}, b_{13+k}^{s_t^k}, b_{14+k}^{s_t^k}\} \end{array} \right)$$

where $\delta^0$ is binding free energy of the first nucleotide triplet with a mismatch to the center nucleotide at position 13 (k=0) on mismatch probes, $\delta^k$ is binding free energy of the second nucleotide triplet with a mismatch at position (13+k) with k≠0.

The above formulae can be applied to probe PB with a shift k in a similar manner. Thus, the parameters $\theta_l^k$, $\delta^k$, and $\lambda$ can be estimated based on the intensities at perfect match probes of homozygous SNP sites.

C. Probe Intensity Modeling of Binding Affinity

The Langmuir adsorption model was applied to the nucleotide binding by extending it from perfect match hybridization only to the binding at both perfect match and mismatch probes. The original Langmuir adsorption isotherm described single layer adsorption and provides a curve that describes the fraction of the surface area of an adsorbent covered with solute, as a function of the concentration of the solute in the contacting liquid phase. The Langmuir isotherm is a curve, convex to the solute concentration axis, and flattens out when the total surface is covered with solute. The isotherm for double layer adsorption is similar to single layer adsorption but the initial convex part of the curve is sharper. The adsorption isotherm only tends to linearity at very low concentrations of solute (at very low surface coverage) and so symmetrical peaks will only be achieved with very small samples. The application of the Langmuir adsorption theory to microarray technology is described below.

Probe intensities at a given quartet of either one mismatch having a shift k' or two mismatches having shifts 0 and k are:

$$I_{PA^k} = N_{PA}^A \varphi(E_A^{S^{PA^k}}(S^{TA^k})) + N_{PA}^B \varphi(E_1^{S^{PA^k}}(S^{TB^k})) + b_{PA^k} + \varepsilon_{PA^k} \quad (4)$$

$$I_{PB^k} = N_{PB}^A \varphi(E_1^{S^{PB^k}}(S^{TA^k})) + N_{PB}^B \varphi(E_B^{S^{PB^k}}(S^{TB^k})) + b_{PB^k} + \varepsilon_{PB^k}$$

$$I_{MA^k} = N_{MA}^A \varphi(E_1^{S^{MA^k}}(S^{TA^k})) + N_{MA}^B \varphi(E_{t_k}^{S^{MA^k}}(S^{TB^k})) + b_{MA^k} + \varepsilon_{MA^k}$$

$$I_{MB^k} = N_{MB}^A \varphi(E_{t_k}^{S^{MB^k}}(S^{TA^k})) + N_{MB}^B \varphi(E_1^{S^{MB^k}}(S^{TB^k})) + b_{MB^k} + \varepsilon_{MB^k}$$

where $t_k=2$ if k≠0, and $t_k=1$ if k=0.

$$\varphi(x) = \frac{1}{1+e^x}$$

is the binding affinity function of free energy by Langmuir adsorption. Vainrub et al., "Coulomb blockage of hybridization in two-dimensional DNA arrays" *Phys Rev E* 66:041905 (2002). The quartets ($N_{PA}^A$, $N_{MA}^A$, $N_{PB}^A$, $N_{MB}^A$) and ($N_{PA}^B$, $N_{MA}^B$, $N_{PB}^B$, $N_{MB}^B$) are copy numbers of target sequences of alleles A and B binding to probes PA, MA, PB, and MB, respectively, and may take different values. The baseline intensities ($b_{PA}$, $b_{PB}$, $b_{MA}$, $b_{MB}$) are model intercepts at probes and may take different values for sense and anti-sense strands. The errors ($\varepsilon_{PA}$, $\varepsilon_{PB}$, $\varepsilon_{MA}$, $\varepsilon_{MB}$) of intensities follow a normal distribution with mean 0 and variance $\sigma^2$.

D. Estimation of Allelic Copy Number

Allele-specific (i.e., for example, allele A and allele B) copy number may be determined at a given SNP, wherein the total copy numbers of the target sequence are the sum of all copy numbers in model (4) when using ten (10) probe quartets; $N_A=\Sigma(N_{PA}^A+N_{MA}^A+N_{PB}^A+N_{MB}^A)$ and $N_B=\Sigma(N_{PA}^B+N_{MA}^B+N_{PB}^B+N_{MB}^B)$ of allele A and allele B, respectively. For homozygous genotype 'AA' at a given SNP, it is expected that PA probes mainly bind through perfect match to target sequences, while the other probes MA, PB and MB bind through mismatch to target sequences. Thus, in theory, $N_B=0$, Similarly, $N_A=0$ is expected at homozygous genotype 'BB'. However, binding at heterozygous genotype 'AB' is complex wherein PA probes bind to target sequences of allele A and allele B through perfect match and mismatch, respectively. Similarly, PB probes bind to target sequences of allele B and allele A through perfect match and mismatch, respectively. Probes MA and MB bind to target sequences through mismatch. In theory, the copy numbers $N_A$ and $N_B$ for genotype 'AB' are expected to be equal ($N_A=N_B$) or close to each other ($N_A \approx N_B$) for normal subjects. The total copy number of a SNP with genotype 'AB' is the sum $N_{AB}=N_A+N_B$. Therefore, $N_{AB}=N_A+N_B$ is true for a SNP of any genotype.

E. Estimation of Gene Copy Number

For a given SNP, probe intensities at each quartet of probes are modeled with model (4), where the binding free energies can be approximated by GPDNN model. Thus, the allele-specific copy number quartets ($N_{PA}^A$, $N_{MA}^A$, $N_{PB}^A$, $N_{MB}^A$) and ($N_{PA}^B$, $N_{MA}^B$, $N_{PB}^B$, $N_{MB}^B$) can be estimated as model parameters with a statistical linear regression model based on model (4). To estimate the above copy numbers, the following approaches can be taken with necessary assumptions:

Approach 1: Assume for a given SNP, the copy numbers of one specific allele A at all probes (i.e., for example, forty) interrogating the given SNP, by array design, are all identical and equal to $N^A$. This approach assumes the allelic copy numbers of allele A are all identical and equal to $N^A$ at different probes and different shifts for the given SNP, and the same for allele B with $N^B$. A linear regression model with fixed effects is then fitted to the intensities of the 40 probes for each given SNP. Thus, the allelic copy numbers at each probe $N^A$ and $N^B$ can thus be estimated with no bias.

Approach 2: The second approach relaxes the above condition on the fixed identical copy numbers and assumes instead that the 40 probes interrogating the given SNP, by array design, have an equal chance to bind to the target sequences of each specific allele, and further allele A copy numbers $(N_{PA}^A, N_{MA}^A, N_{PB}^A, N_{MB}^A)$ of different quartets are independently and identically distributed (iid) random numbers with a normal distribution $N(N^A, \sigma_A^2)$. Similarly, the allele B copy numbers $(N_{PA}^B, N_{MA}^B, N_{PB}^B, N_{MB}^B)$ are iid random numbers with a distribution $N(N^B, \sigma_B^2)$. With these assumptions, model (4) becomes a linear mixed effects model with random allelic copy numbers and fixed intercepts ($b_{PA}^k$, $b_{PB}^k$, $b_{MA}^k$, $b_{MB}^k$). The intercepts may take different values for sense and anti-sense strands, but the same values for different shifts. Thus the total mean allelic copy numbers for alleles A and B are thus $N_A = 40N^A$ and $N_B = 40N^B$, respectively.

Since copy numbers have been estimated so far with single probe intensities in the literature, $N^A$ and $N^B$ are used herein as allelic copy numbers. Notice that estimation by regression model can be subject to a scaling constant with unspecified unit for covariates, and this scaling makes no difference for detecting copy number alterations and genotyping since they are determined by comparing copy numbers in a relative scale. The allelic copy numbers $N^A$ and $N^B$ can be estimated without bias by either linear fixed effect model or linear mixed effects model, the two approaches of model (4). The unbiased estimation in linear mixed effects model has been studied in the literature. Kackar, et al., "Approximations for standard errors of estimators of fixed and random effects in mixed linear models" *J. Amer. Statist. Assoc.* 79, 853-862 (1984).

1. DNA Fragments with Multiple SNPs

In SNP genotyping, chromosomes usually are first digested by certain restriction enzyme and break into DNA fragments (i.e., for example, usually ranging from 500 pb to 2000 bp). Fragments containing given SNPs for interrogation are hybridized after PCR amplification to probe sequences. Most DNA fragments contain one single SNP. However, many DNA fragments also contain multiple (m) SNPs. See, Table 1.

For a given DNA fragment containing m SNPs, the total copy number of each allele is the sum of all allele-specific copy numbers estimated for these m SNPs. Under the same assumption that all probes of the m SNPs for interrogation bind the identical number of target sequences or have an equal chance to bind the target sequences, the mixed effects model (4) fits the intensities of all probes of m SNPs together rather than one SNP at a time. The total copy numbers for a given SNP will be multiplied by the SNP number m, i.e. $mN^A$ and $mN^B$.

2. Alternative Statistical Methods for Model (4)

Model (4) provides a linear model for the estimation of copy numbers $N_A$ and $N_B$. Model (4) incorporates random effects for copy numbers at different probes, and is highly accurate and unbiased. Particularly, it is robust in the sense that the independent variables represent the binding affinities of the probe sequences, which are determined by the probe sequence structure with the statistical conditional model using perfect match probe data and mismatch probe data remain unchanged across different microarrays and array prototypes.

3. Monotonic Transformation/Fitting Generalized Linear Model

Model (4) was based upon Longmuir adsorption model leads to a linear regression model to estimate the copy numbers. If the probe label intensity data demonstrate strongly asymmetric features (i.e., for example, potentially due to saturation of probe intensities in array scanning), transformation of the intensities, such as logarithmic transformation, or Box-Cox transformation, may be employed to transform the intensities to achieve normality and stabilize the variance of the intensities. Then, a linear regression model can be fitted to the transformed intensities. Similarly, a generalized linear model, such as log-linear model, may be fitted to the intensity data for gene copy number estimation.

F. SNP Genotype Calling

Estimated allelic copy numbers to genotype calling on 100K (Xba) and 500K (Nsp) arrays were calculated using the present method based on estimated copy numbers rather than probe intensities. Homozygous SNPs, 'AA' type, yield a large copy number of allele A, and only a relatively small copy number of allele B (non zero due to nonspecific binding or measurement error) while heterozygous SNPs yield large copy numbers for both alleles. This gene copy number based genotype calling method yielded accurate results with low error rate, and also led to robust estimation.

When the estimated allele-specific copy numbers to genotype calling were evaluated on 100K (Xba) and 500K (Nsp) arrays, the method contemplated herein not only yielded more accurate results with zero no call and low error rate, but also led to robust estimation. Model parameters estimated with one array (Xba 0) yielded accurate genotyping results on other 100K arrays as well as 500K arrays with zero no call and low error rate. See, Table 2.

TABLE 1

Number of fragments of DNA target sequence with multiple SNPs (m) by array prototype

| | m | | | | | | | |
|---|---|---|---|---|---|---|---|---|
| Array | 1 | 2 | 3 | 4 | 5 | 6 | 7 | 8 |
| Xba | 36488 | 7784 | 1647 | 305 | 57 | 14 | 2 | 2 |
| Hind | 34654 | 7704 | 1685 | 328 | 75 | 18 | 3 | 0 |
| Nsp | 179469 | 31026 | 5375 | 893 | 155 | 29 | 6 | 1 |
| Sty | 163484 | 28296 | 4696 | 797 | 134 | 26 | 5 | 2 |

TABLE 2

Genotyping error percentage using multiple high density arrays[a].

| | Array | | | | | | | |
|---|---|---|---|---|---|---|---|---|
| | Xba 0 | Xba 1 | Xba 2 | Xba 3 | Nsp 1 | Nsp 2 | Nsp 3 | Nsp 4 |
| Error, % | 0.601 | 0.361 | 0.361 | 0.321 | 1.612 | 1.510 | 1.228 | 1.525 |

Because the Nsp 500K arrays only have twenty-four (24) probes instead of forty (40) for each SNP a larger error rate due to small sample size for the linear regression analysis. Fu et al. "On design and oligonucleotide SNP arrays and methods for genotype calling" *Proceedings of the International Conference of Biomedical Engineering and Informatics:* 453-458 (2008); and Pollack et al., "Microarray analysis reveals a major direct role of DNA copy number alteration in the transcriptional program of human breast tumors" *Proc. Nat. Acad. Sci.* 99:12963-12968 (2002).

HapMap data further illustrates the importance of using data from both perfect match probes and mismatch probes. Homozygous SNPs are expected to be close to the horizontal axis for $N_B=0$ or the vertical axis for $N_A=0$, while heterozygous SNPs are close to the diagonal for $N_A=N_B$. These data clearly demonstrate that mismatch probes provide advantageous and superior modeling and shows that ignoring mismatch data leads to information loss and inaccurate determination of gene copy number.

As shown in Table 2, the fixed effects model (4) utilizing parameters of the GPDNN model trained with one single array (Xba 0) of HapMap data yielded accurate genotype calling on other 100K arrays as well as 500K arrays with zero no call and low error rate compared with HapMap SNP genotyping result. The clusters for this genotype calling were defined by three inequalities:
'AA' type if $N_B<c_1 N_A$; 'BB' type if $N_A<c_2 N_B$; and 'AB' type if $c_1 \leq N_B/N_A \leq 1/c_2$
with boundary lines $N_B=aN_A$ of slopes $1/c_2>c_1>0$ through the origin (top-left panel of FIG. 2).

SNP genotype calling can be conducted based on the estimation of the allele-specific copy numbers $N_A$ and $N_B$. In one embodiment, the present invention contemplates a method for calling genotypes by determining gene copy numbers rather than comparing probe label intensity proportionality. Copy numbers estimated by using linear regression model (4) demonstrated that SNPs were clearly clustered into three groups; i) SNPs having a large ratio of $N_A/N_B$ for genotype 'AA' including negative copy number $N_B$; ii) SNPs having a small ratio of $N_A/N_B$ for genotype 'BB' including negative copy number $N_A$; and iii) SNPs having a moderate ratio of $N_A/N_B$ for genotype 'AB'. See, FIG. 2.

These plots were generated by a method using model (4) from International HapMap data using Affymetrix sequence data downloaded from the Affymetrix Inc website. SNP types are labeled with different colors: AA SNPs green; BB SNPs red; AB SNPs blue. Genotyping with both perfect match probes and mismatch probes yielded the best results to determine unbiased genotyping for homozygous SNPs AA ($N_B=0$ in green), BB ($N_A=0$ in red) and heterozygous SNPs AB ($N_A/N_B$ in blue) (FIG. 2—top left panel). Genotyping with only perfect match probes identified a positive correlation of the copy numbers for alleles A and B of homozygous SNPs AA and BB in conjunction with a large variability for each gene copy numbers indicating an inaccurate estimation. Consequently, the observed positive correlation is misleading (FIG. 2—Top right panel). Genotyping with only mismatch probes showed no correlation of the gene copy numbers of alleles A and B for homozygous SNPs (AA and BB) but did show a positive correlation for heterozygous SNPs (AB), although significant variability was observed (FIG. 2—Panel bottom left). Genotyping without mismatch probe information is different from the top right panel in that the first two formula in model (4) representing perfect match probe intensities were modeled with no binding of allele B to PMA (2nd term of first formula of model (4)) and no binding of allele A to PMB (1st term of second formula of model (4)) considered, while in the Panel top right these two terms are also in the model. (FIG. 2—Panel bottom right). Thus, a criterion with two cutoff values of the ratio $N_A/N_B$ provides a genotype calling method. For the SNP genotype calling, statistical hypothesis testing on the copy numbers $N_A$ and $N_B$ can also be conducted with $N_A \leq 0$ for 'BB' genotype, and $N_B \leq 0$ for 'AA' genotype, and $N_A>0$ and $N_B>0$ for 'AB' genotype.

Other statistical methods for genotype calling include, but are not limited to, shrinkage models (i.e., for example, Lasso or adaptive Lasso), the elastic net (ENet) method which potentially shrinks the copy numbers to 0, or Bayesian variable selection methods utilizing Laplacian priors or stochastic search variable selection (SSVS) methods via Gibbs sampling and/or the Metropolis-Hasting algorithm.

1. Statistical Lasso Shrinkage

Model (4) provides a linear fixed effect or mixed effects model for probe intensities at each quartet for a given SNP. To determine the SNP genotype, the allelic copy numbers $N_A$ and $N_B$ can be estimated as either fixed effect parameters or a mean of random effects. The SNP genotype can be determined with expected allelic copy numbers $EN_A$ and $EN_B$ as follows: 'AA' SNP if $EN_B \leq 0$; 'BB' SNP if $EN_A \leq 0$; and 'AB' SNP if both $EN_A>0$ and $EN_B>0$.

While statistical hypothesis testing may help to make inference on the copy numbers, it may incur bias from noisy data of probe label intensities having a moderate sample size: 40 probes for each given SNP on 100K arrays, and 24 probes on 500K arrays. The hypothesis testing may not yield enough power to detect significance if measurement error is large (common in microarray data). Notice that a no call will be produced if neither copy number $N_A$ nor $N_B$ is significantly greater than 0.

An alternative is statistical variable selection methods, among which a Lasso shrinkage model can shrink copy numbers to 0. The tuning parameter of the Lasso model can be particularly tuned so that at most one allelic copy number is set to 0. Tibshirani, R., "Regression shrinkage and selection via the lasso" *J. Roy. Statist. Soc. B* 58:267-288 (1996): Tibshirani et al., "Diagnosis of multiple cancer types by shrunken centroids of gene expression" "Proc. Nat. Acad. Sci. 99:6567-6572 (2002): Fu W J.", "Penalized regressions: the Bridge versus the Lasso" *J. Comp. Grap. Statist.* 7:397-416 (1998); and Knight et al., "Asymptotics of Lasso-type estimators" *Annals of Statistics* 28:1356-1378 (2000). With a Lasso shrinkage model, genotype calling through linear regression model (4) is either of a fixed effect (i.e., for example, a low variance random intercept) or a mixed effects model (i.e., for example, a high variance random intercept) will be improved to yield accurate results.

G. Comparison of GPDNN to Current Gene Copy Number Determination Methods

A comparison of SNP genotyping was conducted between our method and a previously reported method. Xiao et al (2007)(supra). Xiao et al. used mismatch probe hybridization by simply subtracting the mismatch probe label intensity from perfect match probe label intensity (i.e., equivalently treating mismatch probe data as background noise). Xiao et al. did not use the mismatch probe data efficiently through mathematical modeling and did not use copy number estimation for genotyping calling. A close comparison of FIG. 2 (GPDNN data) to FIG. 3 (Xiao et al.) illustrates the difference. Both methods demonstrate that when using only perfect match probe data genotyping results are inaccurate because the analysis is limited to a positive correlation between gene copy numbers of allele A and allele B and probe intensity. By utilizing mismatch information only, the results may be improved by removing the positive correlation bias. Only, the GPDNN method (FIG. 2) estimates gene copy numbers of alleles A and B using both perfect match probe and mismatch probe data by separating the different SNPs AA, AB and BB with clear boundaries, thereby reducing the no call rate and type I error rate.

As discussed above, current methods for DNA copy number estimation and genotype calling were based on an assumption that the copy number of target sequences were, on the average, proportional to the intensity of perfect match probes. Traditionally, mismatch probe data only served as background control, and was thus of limited use (or no use) and was even recommended to be removed from array design. Carvalho et al., "Exploration, normalization, and genotype calls of high-density oligonucleotide SNP array data" *Biostatistics* 8:485-499 (2007). Nevertheless, the present invention utilizes mismatch sequence data because probe intensities strongly depend on binding affinities of the probe sequences to the target sequence. Further, these binding affinities vary largely from probe to probe, thereby suggesting that consideration of probe primary sequence information may improve accuracy of statistical inference. Zhang et al., "A model of molecular interactions on short oligonucleotide microarrays" *Nature Biotechnology* 21:818-821 (2003); and Zhang et al., "Free energy of DNA duplex formation on short oligonucleotide microarrays" *Nucleic Acids Res* 35:e18 (2007); and Carvalho et al., "Exploration, normalization, and genotype calls of high-density oligonucleotide SNP array data" *Biostatistics* 8:485-499 (2007).

Although it is not necessary to understand the mechanism of an invention, it is believed that mismatch data contains relevant information and ignorance of mismatch information leads to loss of information. Laframboise et al., "PLASQ: a generalized linear model-based procedure to determine allelic dosage in cancer cells from SNP array data" *Biostatistics* 8:323-336 (2007); and Xiao et al., "A multi-array multi-SNP genotyping algorithm for Affymetrix SNP microarrays" *Bioinformatics* 23:1459-1467 (2007). Indeed, mismatch information has been believed to be of no use at all and was excluded in several studies. Rabbee et al., "A genotype calling algorithm for Affymetrix SNP arrays" *Bioinformatics* 22:7-12 (2006); and Carvalho et al., "Exploration, normalization, and genotype calls of high-density oligonucleotide SNP array data" *Biostatistics* 8:485-499 (2007). Others conclude that cross-hybridization makes a non-negligible contribution to probe intensities when interrogating heterozygous SNPs. Zhang et al., "Free energy of DNA duplex formation on short oligonucleotide microarrays" *Nucleic Acids Res* 35:e18 (2007).

The observation of positive correlations in the above ad hoc models for copy number estimation only implies a linear relationship between probe label intensity and copy number on a logarithmic scale. Clearly, these models lack a theoretical basis, which is needed for studying nucleotide sequence structure and probe intensities. Models efficiently using both perfect match probe and mismatch probe data have a theoretical basis in biology, chemistry, and physics and should thereby be expected to yield more meaningful result and improved copy number estimation and SNP genotype calling.

So far, features of perfect match probe sequences and mismatch probe sequences have been characterized quantitatively through PDNN modeling, which characterize perfect match probe sequences by position-specific weighting and pair-wise nucleotide stacking energy. The probe signal intensities were decomposed into two modes of binding, gene-specific binding (GSB), and non-specific binding (NSB), plus an array-specific background. GSB refers to perfect match binding. The PDNN model yielded a strikingly good fit to the sequence signals and showed different weighting at the position of the mismatch nucleotide compared to perfect match. PDNN perfect matching was applied to both DNA/RNA and DNA/DNA hybridization for both gene expression arrays and SNP arrays. Zhang et al. (2003); and Zhang et al. (2007), respectively (supra). Although perfect match probes have been studied with either no mismatch or 1 mismatch, mismatch probes have not been studied yet with the PDNN. The present invention contemplates improvement in determining gene copy number by studying both perfect match and mismatch probes.

The traditional PDNN model is compatible with perfect match probes data, but it is not compatible with mismatch probe data, which may have one mismatch or two. To model mismatch probes, the PDNN model must be generalized to model more mismatches. Without the PDNN model, or its generalization, the total number of permutations of a 25-mer probe sequence is huge ($4^{25} > 1.125 \times 10^{15}$) and the calculation of its binding free energy is impossible.

In one embodiment, the present invention contemplates a Generalized PDNN model (GPDNN) incorporating data from both perfect match and mismatch probes. In one embodiment, the modeled probe intensities with allelic copy numbers and binding affinity are based on Longmuir adsorption. Although it is not necessary to understand the mechanism of an invention, it is believed that this GPDNN model was built upon rules governing probe intensities, binding free energies of nucleotide sequence, and binding affinity. It is further believed that since GPDNN characterizes probe intensities utilizing nucleotide sequence structure model complexity is reduced from $4^{25}$ parameters to approximately two thousand (2000) or fewer. In one embodiment, GPDNN estimates allelic copy numbers through a linear regression model.

H. Modeling for Nucleotide Binding Free Energy with Probe Structure

As described above in models (1-4) gene copy number may be accurately determined. In one embodiment, the present invention contemplates models (1-4) having a further improvement comprising calculating the binding free energy of a probe oligonucleotide and a target sequence. The above generalized PDNN models accommodate DNA nucleotide bindings with 0 mismatch, 1 mismatch and 2 mismatches using positional nucleotide-pair stacking energy for perfect match and positional nucleotide-triplet stacking energy for mismatch.

A model for binding free energy further improves the accuracy of these models utilizing a perfect match probe comprising positional nucleotide triplets (instead of paired positional nucleotides utilized above) to evaluate neighboring effect on stacking energy by positional weight and nucleotide triplet at position (p, p+1, p+2).

$$E_A^{S^{PA^k}}(S^{TA^k}) = \sum_{p=1}^{23} \omega_p \lambda(b_p^{SPA}, b_{p+1}^{SPA}, b_{p+2}^{SPA}) \quad (5)$$

where $\lambda$ represents the stacking energy of the nucleotide triplet. $\omega_p$ is a positional weight. Furthermore, mismatches can be modeled with nucleotide quintuplets instead of triplets to take into account the neighboring effect of mismatch nucleotide of one mismatch and two mismatches as follows.

$$E_1^{S_p^k}(S_t^k) = \sum_{\substack{l=1 \\ l \neq 11+k', 12+k', 13+k'}}^{23} \theta_l^k \lambda(b_l^{S_p^k}, b_{l+1}^{S_p^k}, b_{l+2}^{S_p^k}) + \qquad (6)$$

$$\xi^k\left(\{b_{11+k'}^{s_p^k}, b_{12+k}^{s_p^k}, b_{13+k'}^{s_p^k}, b_{14+k'}^{s_p^k}, b_{15+k'}^{s_p^k}\}, \right.$$
$$\left. \{b_{11+k'}^{s_t^k}, b_{12k'}^{s_t^k}, b_{13+k'}^{s_t^k}, b_{14+k'}^{s_t^k}, b_{15+k'}^{s_t^k}\}\right),$$

and $$E_2^{S_p^k}(S_t^k) = \sum_{\substack{l=1 \\ l \neq 11, 12, 13, 11+k, 12+k, 13+k}}^{23} \theta_l^k \lambda(b_l^{S_p^k}, b_{l+1}^{S_p^k}, b_{l+2}^{S_p^k}) + \qquad (7)$$

$$\xi^0\left(\{b_{11}^{s_p^0}, b_{12}^{s_p^0}, b_{13}^{s_p^0}, b_{14}^{s_p^0}, b_{15}^{s_p^0}\}, \{b_{11}^{s_t^0}, b_{12}^{s_t^0}, b_{13}^{s_t^0}, b_{14}^{s_t^0}, b_{15}^{s_t^0}\}\right) +$$
$$\xi^k\left(\{b_{11+k}^{s_p^k}, b_{12+k}^{s_p^k}, b_{13+k}^{s_p^k}, b_{14+k}^{s_p^k}, b_{15+k}^{s_p^k}\}, \{b_{11+k}^{s_t^k}, b_{12+k}^{s_t^k}, b_{13+k}^{s_t^k}, b_{14+k}^{s_t^k}, b_{15+k}^{s_t^k}\}\right)$$

where $\lambda$ is the same as in (6), $\theta_l^k$ is a positional weight for perfect binding free energy. $\xi^k$ is the stacking energy of mismatch nucleotide quintuplet with shift k, similarly $\xi^0$ is the stacking energy of mismatch nucleotide quintuplet at the center position of mismatch probes with no shift (k=0). The accuracy of the GPDNN model of the free energy of probe nucleotide sequences is expected to improve with the above fine-tuning of the nearest-neighbor effect on stacking energy.

I. Non-Linear Probe Intensities Modeling

A linear regression model (4) has been developed for probe intensities based on Langmuir adsorption theory. This model assumes that probe intensities depend linearly on the binding affinity and allelic copy numbers. However, in microarray experiments, probe intensities frequently reach saturation. Thus a non-linear model reflecting this intensity saturation may be more appropriate, with which the probe intensity may increase linearly for low and moderate expression level but may increase slowly for expression beyond certain high level. Therefore, it can be assumed that a monotone transformed probe intensity, such as log(1+x)-transformed probe intensity, depends linearly on the binding affinity and allelic copy numbers. Therefore, a further generalization of model (4) through a non-linear monotone transformation is proposed below.

$$f(I_{PA^k}) = N_{PA}^A \varphi(E_A^{S^{PA^k}}(S^{TA^k})) + N_{PA}^B \varphi(E_1^{S^{PA^k}}(S^{TB^k})) + b_{PA^k} + \varepsilon_{PA^k} \qquad (8)$$

$$f(I_{PB^k}) = N_{PB}^A \varphi(E_1^{S^{PB^k}}(S^{TA^k})) + N_{PB}^B \varphi(E_B^{S^{PB^k}}(S^{TB^k})) + b_{PB^k} + \varepsilon_{PB^k}$$

$$f(I_{MA^k}) =$$
$$N_{MA}^A \varphi(E_1^{S^{MA^k}}(S^{TA^k})) + N_{MA}^B \varphi(E_{t_k}^{S^{MA^k}}(S^{TB^k})) + b_{MA^k} + \varepsilon_{MA^k}$$

$$f(I_{MB^k}) = N_{MB}^A \varphi(E_{t_k}^{S^{MB^k}}(S^{TA^k})) + N_{MB}^B \varphi(E_1^{S^{MB^k}}(S^{TB^k})) + b_{MB^k} + \varepsilon_{MB^k}$$

where f is a monotone transformation, such as log(1+x) transformation, all other terms on the right-hand-side of the equations remain the same as in (4). Model (8) allows a monotone non-linear transformation to model probe intensities with potential saturation in fluorescence scan. A number of transformations for probe intensities, including log(1+x), square-root, cubic-root transformations may be evaluated using this model. The choice of log(1+x) versus log(x) is to ensure transformed intensities being positive because all terms on the right-hand-side of model (8) are positive except for measurement errors. The transformation is expected to stabilize the variance of error term, to bring extreme values back to normal range for better model fitting, especially to noisy data.

J. Efficient Methods for SNP Genotype Calling

1. Statistical Hypothesis Testing Approach

The unbiased estimation of allelic copy numbers ($N_A$, $N_B$) can be applied with their expected values ($EN_A$, $EN_B$) to SNP genotype calling: 'AA' SNPs if $EN_B \leq 0$; 'BB' SNPs if $EN_A \leq 0$; or 'AB' SNPs if both $EN_A > 0$ and $EN_B > 0$. Hence, a novel method based on statistical inference on the allelic copy numbers can be pursued with null hypothesis $H_0$ and alternative hypothesis $H_1$:

$H_0$: either $EN_A \leq 0$ or $EN_B \leq 0$ vs $H_1$: both $EN_A > 0$ and $EN_B > 0$. (10)

This hypothesis testing approach can be pursued under either a linear fixed effect model or a linear mixed effects model following the inference on the allelic copy numbers. This hypothesis testing approach facilitates SNP genotype calling with standard statistic procedure and may lead to improved accuracy in genotyping.

2. Statistical Variable Selection Approach

Alternatively, variable selection methods can also be applied for SNP genotype calling since variable selection methods select significant variables ($EN_A$ or $EN_B > 0$) in the model and remove nonsignificant ones. George, E. "The variable selection problem" *J. Amer. Statist. Assoc.* 95:1304-1308 (2000). These methods include, but are not limited to, forward or backward selection, Bayesian stochastic search variable selection (SSVS), or Lasso shrinkage models. While the forward and backward selection methods are standard statistical procedures and have been adopted by common statistical software, two specific methods are illustrated below only for exemplary purposes.

a. Bayesian SSVS Approach

Bayesian SSVS method assumes that each model parameter $\beta_i$ (model intercept, and allelic copy numbers) follows a prior distribution of a mixture of normal distributions of spike and slab. George et al., "Variable selection via Gibbs sampling" *J. Amer. Statist. Assoc.* 88:881-889 (1993). By introducing a latent variable $\gamma_i = 0$ or 1 with probability $P(\gamma_i = 1) = p$, the conditional normal mixture distribution is:

$\beta_i | \gamma_i \sim (1-\gamma_i) N(0, \tau_i^2) + \gamma_i N(0, c_i^2 \tau_i^2)$, where i is the parameter index. The normal distribution $N(0, \tau_i^2)$, a spike, has a very small variance $\tau_i^2$ to generate a value 0 safely for the parameter $\beta_i$ if $\gamma_i$ is chosen to be 0, while the constant $c_i^2$ is large enough to be able to generate a nonzero value for the parameter $\beta_i$ from the normal distribution $N(0, c_i^2 \tau_i^2)$, a slab, with a moderate to large variance $c_i^2 \tau_i^2$ if $\gamma_i$ is chosen to be 1. The Gibbs sampling method can be employed by iteratively updating one parameter at a time for all model parameters ($\beta_1, \ldots, \beta_q$), say, following a conditional distribution $\pi$ conditioning on other parameters with the most updated values:

Generate $\beta_1' \sim \pi(\beta_1 | \beta_2, \ldots, \beta_q)$, then $\beta_2' \sim \pi(\beta_2 | \beta_1',$
$\beta_3, \ldots, \beta_q), \ldots, \beta_q' \sim \pi(\beta_q | \beta_1', \ldots, \beta_{q-1}')$.

This Bayesian SSVS method computes the posterior distribution of parameters and selects variables with a large posterior probability and sets other variables to 0 for variable selection. Since linear regression models (4) and (8) have a moderate number of parameters, the moderate dimension of parameter space will lead to fast Bayesian stochastic search for variable selection in each SNP interrogation.

This Bayesian SSVS approach can also be applied to the mixed effects model through a Bayesian hierarchical model by assuming that the mean copy numbers follow a prior distribution of a mixture of normal distributions with spike and slab. The Bayesian SSVS method may also be applied to the mixed effect model through a Bayesian hierarchical model for variable selection on allelic copy numbers and SNP genotype calling.

b. Lasso Shrinkage Model Approach

The Lasso shrinkage model takes a different approach by shrinking model parameters towards the origin and thus removes some variables by setting their parameters to 0 and effectively selects other variables. For linear fixed effect model (4), the Lasso minimizes the residual sum of squares as in the least-squares model but with an extra constraint on the model parameters of interest in variable selection:

$$\min \Sigma(I_{pk} - \alpha_p - x_{pkA} N_A - x_{pkB} N_B)^2 \text{ subject to } |N_A| + |N_B| \leq t, (\alpha_p, N_A, N_B) \quad (10)$$

where $I_{pk}$ is the probe intensity at shift k, $\alpha_p$ is the intercept of one probe type (PA, MA, PB, MB), $x_{pkA}$ and $x_{pkB}$ are binding affinities of probes at shift k for alleles A and B, respectively. The summation ($\Sigma$) is over all 40 probes for interrogating a given SNP. t is a Lasso tuning parameter and the absolute values ($L_1$ norm) in the constraint $|N_A| + |N_B| \leq t$ warrants variable selection by small value $t > 0$, i.e. the estimates $N_A = 0$ or $N_B = 0$ to achieve variable selection. The tuning parameter t of the Lasso shrinkage model can be selected with Bayesian Information Criterion (BIC) by minimizing the BIC:

$$BIC = [I_{pk} - I_{pk}(t)]^2/(n\sigma^2) + \log(n) p(t)/n, \quad (11)$$

where $I_{pk}(t)$ is the fitted value of probe intensity with tuning parameter t. $\sigma^2$ is the estimated variance of error. n=40 is the sample size for given SNP with Affymetrix 100K SNP arrays. BIC has been reported to lead to a consistent estimation of the copy numbers. Knight et al., "Asymptotics of Lasso-type estimators" *Annals of Statistics* 2000, 28:1356-1378 (2000); Zou, H., "Adaptive Lasso and its oracle properties" *J. Amer. Statist. Assoc.* 101:1418-1429 (2006); and Zou et al., "On the "degrees of freedom" of the Lasso" *Ann. Statist.* 35: 2173-2192 (2007). p(t) is the effective number of model parameters, which can be calculated from the Lasso model or by the definition: p(t)=ps with p being the number of parameters in the Lasso model, and the standard shrinkage rate:

$$s = (|N_A^l| + |N_B^l|)/(|n_A| + |n_B|)$$

for the Lasso with the least-squares estimator ($n_A$, $n_B$) and Lasso estimator ($N_A^l$, $N_B^l$). Fu W J., "Nonlinear GCV and quasi-GCV for shrinkage models" *J. Statistical Planning and Inference* 131:333-347 (2005). If BIC does not perform well in selecting the tuning parameter t for the Lasso shrinkage models, the nonlinear generalized cross-validation (GCV) method can also be applied as an alternative:

$$GCV = RSS/[n(1 - ps/n)^2],$$

where RSS is the residual sum of squares of the shrinkage model (9) with fitted values $I_{pk}(t)$, $$RSS = \Sigma_{pk}[I_{pk} - I_{pk}(t)]^2,$$

p is the number of parameters for regression model (4) or (8), and s is the standard shrinkage rate defined as above, n=40 is the sample size for given SNP with Affymetrix 100K SNP arrays.

c. Oracle Property for Lasso/Adaptive Lasso Shrinkage Models

It is believed that although Lasso shrinks model parameters to 0 to achieve variable selection, it does not possess the oracle property—a property that ensures the selected nonzero variables being in the true underlying model. Although the Lasso model has been shown not to possess such oracle property, the adaptive Lasso does: for example, the adaptive Lasso correctly selects variables for large enough sample size as if the true underlying model is known. Zou, H., "Adaptive Lasso and its oracle properties" *J. Amer. Statist. Assoc.* 101:1418-1429 (2006). The adaptive Lasso is defined slightly different in the constraint with weights by the least-squares estimator:

$$\min \Sigma(I_{pk} - \alpha_p - x_{pkA} N_A - x_{pkB} N_B)^2 \text{ subject to } (|N_A|/|n_A|) + (|N_B|/|n_B|) \leq t, (\alpha_p, N_A, N_B) \quad (12)$$

where $n_A$ and $n_B$ are the least-squares estimates for $N_A$ and $N_B$, and all other terms remain the same as in model (10). Similar to the Lasso, the tuning parameter t can be selected with BIC method that leads to consistent estimation with oracle property of the adaptive Lasso estimator. The adaptive Lasso model (12) is expected to yield accurate SNP genotype calling with its oracle property and consistency.

For fixed effects model (8) with nonlinear-transformed intensities, the Lasso and adaptive Lasso shrinkage models can be applied similarly for variable selection and SNP genotype calling. For the mixed effect models (4) and (8) with random allelic copy numbers, however, the adaptive shrinkage Lasso model can be developed to include random effects involved in copy number estimation and SNP genotype calling.

K. MA-Ratio with Application to Genotype Calling

Previous genotype calling algorithms have achieved certain accuracy, but have a few intrinsic problems. Most of them are based on multi-array (multi-subject) approach, which technically (computationally) makes the (DNA) SNP genotype depend on data of unrelated individuals, which is not supported by biological principles. The PICR method developed by Wan et al 2009 NAR used a different approach to resolve this issue by generating the allelic copy numbers from oligonucleotide SNP arrays so that SNP genotypes are called with an individual array (single subject). However, the previous genotype calling method based on the ratio of the allelic copy numbers still needs improvement although it has been shown to achieve better results than other promising methods, including CRLMM (Wan et al. 2009 NAR). This current version uses a novel approach by incorporating the HapMap clustering structure into the algorithm which improves accuracy. Although it is not necessary to understand the mechanism of an invention, it is believed that the present calling algorithm, that incorporates the HapMap cluster structure, improves accuracy in relation to other current methods.

This improved calling criteria uses single array based allelic copy number method to call the SNP genotype, and improves the calling accuracy of the previous method based on the ratio of allelic copy numbers. The high accuracy increases the statistical power for association detection in genome-wide association studies and lowers false positive and negative rates. Although it is not necessary to understand the mechanism of an invention, it is believed that the present MA ratio, as applied to the genotype calling method, creates advantages in relation to other current methods. Thus, advantages include, but are not limited to, generation of genotype calls on individual arrays (e.g. Affy 500 K arrays), which can be an on-line feature that does not have to pool multiple arrays together; generation of SNP genotype calls extremely fast by taking advantage of storing all array information in the algorithm as constants for optimal output; and the R-package is easy to use since it is a software package for statistical analysis which has been adopted by most people in bioinformatics research.

Thus, for each given SNP, the allelic concentrations (copy numbers) for alleles A and B can be estimated with the linear regression (Wan et al 2009). The standardized allelic copy numbers (copy number estimates standardized with its variance covariance matrix) are expected to be normally distributed and independent with each other. An MA ratio is defined for the given SNP as:

$$r=(N_A-N_B)/|N_A+N_B|$$

The genotype calling criteria are provided based on this MA ratio that can properly separate the potential 3 genotype groups, AA, AB, and BB. The SNP-wise criteria are determined either by training of HapMap annotation or by unsupervised learning, depending on the availability of HapMap annotation for each SNP. In one embodiment, the present invention contemplates comprehensive statistical analyses including, but not limited to, improved calculation of copy numbers based on the MA ratio disclosed above. In one embodiment, the present invention contemplates improved genotype calling. In one embodiment, the present invention contemplates lower false positive and/or false negative rates. Below is a summary of the criteria according to various scenarios of the HapMap annotations as follows:

1. HapMap SNPs having 3 groups of annotated genotypes
    Number of SNPs: 228,008 in NSP array, 174,269 in STY array
    In general, for each given SNP, the median of MA ratio was first calculated for each annotated group as mA, mH, and mB for AA, AB and BB genotypes, respectively. Then, the cut-off values between homozygous and heterozygous are defined as:

$$c1=(mA+mH)/2$$

$$c2=(mB+mH)/2$$

Although it is not necessary to understand the mechanism of an invention, it was found that this calling criteria yielded good clustering for most of the SNPs and remained robust in the Wellcome Trust dataset (first 500 Controls). See FIG. 9 as an illustrated example. For FIGS. 9-14, the following color designations apply: "AA" SNPs in Blue; "AB" SNPs in Green; and "BB" SNPs in Red; "No call" SNPs in Black for HapMap. "Control samples" in Pink (500 control samples from Wellcome Trust data). Moreover, the issue of extreme values was fixed by going over the SNPs with extreme cut-offs up to 1% from the top of the data range and 1% from the bottom of the data range (about 8.5K SNPs). Thus, although it is not necessary to understand the mechanism of an invention, it is believed some annotation errors or mis-labelings of some SNPs in the HapMap samples may lead to poor genotype calls if not fixed, see FIG. 10.

2. SNPs with only 1 homozygous and 1 heterozygous annotations
    Number of SNPs: 21,069 in NSP array, 18,402 in STY array
    Step 1: In this scenario, one of the homozygous groups was not observed in the HapMap samples due to the small minor allele frequency. It was noticed that the Wellcome Trust controls were selected from British population and were thus close to the HapMap CEU group genetically. Therefore, we first identified the SNPs with observed heterozygous in CEU population and combined roughly 500 Wellcome Trust controls with HapMap samples in searching for the minor homozygous group. Although it is not necessary to understand the mechanism of an invention, it was found that in general the third genotype group was able to be found and was helpful to setting up the calling criteria (about 7.5K in NSP array and 7K in STY). See FIG. 11A.
    Step 2: For the remaining SNPs, some of them may still have 3 groups due to the incomplete or inaccurate HapMap annotation. In this situation, the first two observed groups were used to determine one cut-off value between AA and AB (or BB and AB), and further used the k-mean method to search for the third cluster beyond the 2 standard deviation of the MA ratios of the heterozygous group. See FIG. 11B. Three groups will be claimed if another cluster beyond heterozygous is found. Otherwise, the other cut-off is selected to be the mirror image of the first cutoff value about the median of the heterozygous group. See FIGS. 11C and 11D
    Step 3: The second cut-off may not be as accurate as the first one, since there is no information for the minor homozygous group. Potential problems were further examined by going over the SNPs with extreme cut-offs using the same threshold as in Scenario 1.

3. SNPs with Only 2 homozygous annotations but no heterozygous annotation
    Number of SNPs: 13 in NSP arrays and 7 in STY arrays
    In this scenario, the number of SNPs is extremely small and the number of observations is usually dominating in one of the homozygous groups. Therefore, these SNPs were simply gone over and the criteria were selected visually. See FIGS. 12A and 12B. Although it is not necessary to understand the mechanism of an invention, some potential problems in the HapMap annotation were found.

4. SNPs with only 1 annotated homozygous
    Number of SNPs: 232 in NSP array and 168 in STY array
    Similar to the scenario 3, the number of SNPs is small thus it is more likely to have potential annotation problems. Therefore, the SNPs here were gone over to select calling criteria and to identify the annotation problems. See FIGS. 13A and 13B.

5. SNPs with heterozygous annotation only
    No SNPs found in either NSP or STY array.

6. SNPs with no HapMap annotation
    Number of SNPs: 3,038 in NSP array and 2,721 in STY array
    In this scenario, unsupervised learning was conducted with k-mean method after removing outliers.
    Step 1: Outliers of MA ratios need to be removed before the k-mean procedure. We first sort the MA ratios and tried to remove those outliers from either the top or bottom. The removal process was stopped until the ratio was within 0.1 of the ratio next to it.
    Step 2: The initial k-mean procedure was performed in searching for 3 clusters. After the clustering, the between-cluster distances were calculated as the minimum distance between cluster members. If the between clusters distances were less than 0.1, the k-mean procedure was rerun in searching for 2 clusters. The calling criteria could be made accordingly based on the k-mean result.
    Step 3: We also went through the SNPs in this scenario for quality check and problem correction. See FIGS. 14A and 14B.

In one embodiment, the present invention contemplates a method for genotype calling using individual arrays (e.g. Affy 500 K arrays), which can be an on-line feature that does not require pooling multiple arrays together. In one embodiment, the method is used to generate SNP genotype calls extremely fast by storing all array information in the algorithm as constants for optimal output. In one embodiment, the method incorporates the HapMap clustering structure into the algorithm, which improves accuracy. In another embodiment, the SNP-wise criteria are implemented by training the HapMap annotation or by unsupervised learning.

IV. Determination of Copy Number Estimations

In one embodiment, the present invention contemplates a method for estimating DNA copy number. In one embodiment, the method is used in conjunction with human genetic variation studies (i.e., for example, copy number variation (CNV) studies). In one embodiment, the present invention contemplates a novel probe intensity model comprising an analysis of sample independent probe sequences, their binding free energy and binding affinity. In one embodiment, the model calculates a consistent and accurate estimation of gene copy number. In another embodiment, the copy number estimation model comprises a copy number-based SNP genotype calling method. These embodiments are validated through experimentally confirmed copy numbers of cell-line data and genotypes of HapMap data, and further demonstrated to be robust and highly accurate across samples, laboratories and array prototypes (infra).

Recently, CNV studies have become challenging and complicated because of an increased availability of microarray platforms because CNV detection depend upon accurate copy number estimation and genotype calling. Scherer et al., "Challenges and standards in integrating surveys of structural variation" *Nat Genet.* 39:S7-15 (2007); and Carter N. P., "Methods and strategies for analyzing copy number variation using DNA microarrays" *Nat Genet.* 39:S16-S21 (2007). While most CNV studies depend on genotype information and require pre-determination of SNP genotype, many rely on large sample multi-array training, and therefore may not be suitable for cross-laboratory and small sample studies. This is a particular disadvantage if a given SNP is strongly associated with the phenotype of interest. Since large scale genome-wide studies often involve collaboration among laboratories, the development of robust methods of copy number estimation that are sample independent should avoid erroneous conclusions.

MM1 intensity was compared to PM1 intensity in accordance with Example I. See, FIG. 4A. Similarly, PM2 intensity was compared to PM1 intensity and MM2 intensity compared to PM1 intensity. See, FIGS. 4B and 4C, respectively. The data indicates that MM1 intensity and PM2 intensity are comparable to PM1 intensity, as seen by the slopes greater than 0.2 and highly significant positive correlations. However, MM2 intensity was not comparable to PM1, with slopes less than 0.07—except that the slope was around 0.68 at the center position (k=0), in which case there was only one mismatch nucleotide to the target sequence. This disparity results from lower intensities of MM2 probes because of one more mismatch nucleotide than with MM1 and PM2. This further indicates that mismatch probe intensities are mainly a result of specific-binding rather than background nonspecific-binding. Although it is not necessary to understand the mechanism of an invention, it is believed that had the background non-specific-binding been dominant, the difference between the slopes of MM2 and MM1 or PM2 would not have been so large.

Human genetic variation studies offer great promise in deciphering the genetics of complex diseases through genome-wide association and copy number variation studies, and for the latter accurate estimation of copy number is necessary. Quantitative methods have been developed for estimating copy number, but several limitations need to be addressed. Among them, many methods rely on sample-dependent training methods and may not be suitable for cross-laboratory studies. Importantly, none sufficiently utilizes the information available in microarray data. A more complete understanding of the mechanisms and technology could result in an improvement of computational methods. To this end, the present study aims to develop a probe intensity composite representation (PICR) model for DNA copy numbers and probe sequence binding affinity using sample-independent information. This approach yields robust estimates of DNA copy numbers and SNP genotypes across samples, laboratories, and even array prototypes, and is here validated with the results of experimentally confirmed data performed in accordance with Example II.

Estimated allelic copy numbers of SNPs was determined by PICR in a randomly selected non-training sample (NA07056_$Xba_A11$_4000090). A total of 41,099 SNPs with HapMap annotation were plotted with genotypes in different colors. See, FIG. 6A. 'AA' SNPs had a small copy number $N_B$ relative to $N_A$ with a mean $N_B$ around 0. A similar observation was true for 'BB' SNPs. Heterozygous SNPs had large positive values (close to each other) for both $N_A$ and $N_B$. These observations indicate nearly unbiased estimation of allelic copy numbers. Mismatch probes were found to contain information useful for copy number estimation via PICR. See, FIGS. 6A, 6B and 6C. For example, the copy numbers of 'AA' and 'BB' SNPs, when estimated by only using perfect match probes (PA and PB, FIG. 6B), were systematically biased with mean $N_B>0$ for the 'AA' type and $N_A>0$ for the 'BB' type. This bias disappears when all probes are used. Compare, FIG. 6A. Conversely, when using only mismatch probes (MA and MB, FIG. 6C) a nearly unbiased estimation results, with a larger variance resulting from loss of the information from considering only perfect match probes. Although it is not necessary to understand the mechanism of an invention, it is believed that by excluding mismatch probes a biased copy number estimation with large errors results. See, FIG. 6D. This is consistent with previously reported data reporting that when using a mean intensity of perfect match probes as a surrogate for allelic copy numbers a biased estimation of copy numbers for homozygous SNPs results. Slater et al., "High-resolution identification of chromosomal abnormalities using oligonucleotide arrays containing 116,204 SNPs" *Am J Hum Genet.* 77:709-726 (2005).

In one embodiment, the present invention contemplates a PICR genotype calling method comprising an accurate estimation of allelic copy numbers $N_A$ and $N_B$. In one embodiment, the method uses all probe intensities of a given SNP. Although it is not necessary to understand the mechanism of an invention, it is believed that it is based on a statistical decision of whether one allelic copy number $N_A$ or $N_B$ is zero: i) a SNP is of 'AA' type if $N_B=0$; ii) a SNP is of 'BB' type if $N_A=0$; or iii) a SNP is of 'AB' type if both $N_A>0$ and $N_B>0$. For each sample, allelic copy numbers of a given SNP were estimated with PICR using all probes and were plotted. See, FIG. 6A. These SNPs were further grouped into 3 clusters using two lines through the origin (0, 0). The slopes of the two lines were trained with one training sample to minimize the genotyping error rate for that sample. The performance of the copy number-based genotype calling method with these same slopes was assessed using the gold standard HapMap annotation of all 90 samples of the Mapping 50K Xba 240 Array from the 100K HapMap Trio Dataset and 15 samples (5 HapMap CEPH trios) of the Mapping 250K Nsp Array from the 500K dataset available on the Affymetrix website.

Summary statistics of the predicted accuracy were computed separately for all 90 Xba 2 arrays and all 15 Nsp arrays. Allelic copy numbers were computed with PICR for each given SNP, and were plotted together 4 with all SNPs in a scatter plot similar to FIG. 6A. For genotype calling of any given SNP, three clusters were formed with two lines through the origin: y=kx and y=1/k(x) with k>1. The choice of k and 1/k is to ensure symmetry. The genotype of each SNP was then determined: i) a SNP is of 'AA' type if $N_B<(1/k) N_A$; ii) a SNP is of 'BB' type if $N_A<k N_B$; or iii) a SNP is of 'AB' type if $(1/k)N_A \leq N_B \leq k N_A$. The slopes k and 1/k were obtained by minimizing the genotyping error with the training sample NA06985_Xba_B5_4000090 based on HapMap SNP annotation and k=3.5 was selected. The same value of k=3.5 was applied to other samples for genotyping by clustering the SNPs. This genotype calling method yielded zero no-calls and consistently achieved high accuracy across arrays, laboratories, and array prototypes, as shown in Table 3 (below).

TABLE 3

Summary statistics of genotyping accuracy (proportion of correct genotypes) based on allelic copy numbers trained with a single sample of the Xba array

| Sample | Mean | SD[a] | Median | 5%[b] | 95%[c] |
|---|---|---|---|---|---|
| 90 Xba arrays | 0.9966 | 0.0034 | 0.9975 | 0.9920 | 0.9987 |
| 15 Nsp arrays | 0.9916 | 0.0014 | 0.9921 | 0.9894 | 0.9930 |

[a]standard deviation.
[b]5-th percentile.
[c]95-th percentile

Training with one single Xba array, the high accuracy with mean 99.66% (SD 5=0.0034) correct genotyping over 90 Xba arrays and mean 99.16% (SD=0.0014) over 15 Nsp arrays indicates the robustness of this method.

A nearly equal distributions of total copy numbers was observed among SNPs of different genotypes, which further indicates high accuracy of copy number estimation. See FIG. 7. Although it is not necessary to understand the mechanism of an invention, it is believed that the estimated copy numbers are the copy numbers of DNA fragments in samples after PCR amplification, rather than before PCR amplification, and are thus large in scale and may vary largely from SNP to SNP owing to many factors present in the PCR amplification procedure, including sample preparation and amplification efficiency, etc. Nannya et al., "A robust algorithm for copy number detection using high-density oligonucleotide single nucleotide polymorphism genotyping arrays" *Cancer Res* 65:6071-6079 (2005); and Zhang et al., "Free energy of DNA duplex formation on short oligonucleotide microarrays" *Nucleic Acids Research* 35:e18 (2007).

In some embodiments, the PICR model described herein not only provides a robust method for genotype calling, but also provides potentially high resolution of copy number estimation at single SNP sites. Although it is not necessary to understand the mechanism of an invention, it is believed that with this higher resolution, further studies of copy number-based variation and detection can be performed with high sensitivity and improved accuracy. The methods disclosed herein provide significant advantages over recent CNV studies that have been identified as being subject to several challenges. Scherer et al., "Challenges and standards in integrating surveys of structural variation" *Nat Genet.* 39:S7-15 (2007); and Carter N. P. "Methods and strategies for analyzing copy number variation using DNA microarrays" *Nat Genet.* 39:S16-S21 (2007). Most CNV studies calculate copy numbers directly based on probe intensities, which vary largely with binding affinity from probe to probe and are subject to the large noise inherent in the array technology. Weir et al. "Characterizing the cancer genome in lung adenocarcinoma" *Nature* 450:893-898 (2007); Slater et al., "High-resolution identification of chromosomal abnormalities using oligonucleotide arrays containing 116,204 SNPs" *Am J Hum Genet.* 77:709-726 (2005); and Huang et al., "CARAT: a novel method for allelic detection of DNA copy number changes using high density oligonucleotide arrays" *BMC Bioinformatics* 7:83 (2006). In one embodiment, the present invention contemplates a PICR copy number estimation method yielding a more accurate result with higher resolution than a probe intensity-based CARAT method, (see, cell line data presented herein).

It is worthwhile noting that currently available genotype calling methods consider only 3 genotypes ('AA', 'BB', and 'AB'), and are suitable only for normal samples evaluations (i.e., no insertions or deletions), and may not be suitable at all for studying abnormal variations (i.e., for example, homozygous or heterozygous deletions, balanced and unbalanced amplifications, etc.) In one embodiment, the contemplated allelic copy number-based genotype calling approach detects subtle copy number variations at single SNP sites, such as homozygous or heterozygous deletions (data not shown). It is believed that these DNA abnormalities have not yet been extensively studied because of the limitations of current genotype calling methods.

Another disadvantage of current genotype calling methods is because mismatch probes were classified as background noise thereby leading to inaccuracy. Abdueva et al., "Non-linear analysis of GeneChip arrays" *Nucleic Acids Research* 34:e 105 (2006); Carvalho et al., "Exploration, normalization, and genotype calls of high-density oligonucleotide SNP array data" *Biostatistics* 8:485-499 (2007); Held et al. "Relationship between gene expression and observed intensities in DNA microarrays—a modeling study" *Nucleic Acids Research* 34:e70 (2006); Held et al., "Modeling of DNA microarray data by using physical properties of hybridization" *Proc Natl Acad Sci USA* 100:7575-7580 (2003); Irizarry et al., "Summaries of Affymetrix GeneChip probe level data" *Nucleic Acids Research* 31:e15 (2003); and Irizarry et al., "Exploration, normalization, and summaries of high density oligonucleotide array probe level data" *Biostatistics* 4:249-264 (2003). These inaccuracies were largely due to observations that about 30% of mismatch probes had higher intensity than the corresponding perfect match probes, which was difficult to explain with the belief that mismatch probes represent only background noise and non-specific binding. In some embodiments, the present invention contemplates that mismatch probes mainly consist of specific-binding to target sequences with up to 2 mismatch nucleotides that may present strong intensity comparable to perfect match binding. Although it is not necessary to understand the mechanism of an invention, it is believed that previous use of mismatch probes for only background control has led to tremendous information loss. In a preliminary study that excluded mismatch probes from the PICR model lead to a 50-fold increase in genotyping error, while their inclusion not only doubled the sample size but also yielded nearly unbiased estimation of copy numbers with high accuracy. Fu et al., "On design of oligonucleotide SNP arrays and methods for genotype calling" *Proceeding of The International Conference on Bio-Medical Engineering and Informatics:*453-458 (2008).

Among-array normalization is a method widely used in microarray studies to remove variability resulting from artifacts in array processes that confound biological differences. However, among-array normalization introduces undesired variability into SNP genotyping, in that an individual's genotype then depends on the data of other individuals, irrespective of the fact that full individual information is contained in one single array. Although it is not necessary to understand the mechanism of an invention, it is believed that the presently contemplated copy number-based genotype calling method through the PICR model does not require among-array normalization because this variability is modeled by the model intercept and consequently does not affect the estimation of the relative values of the allelic copy numbers $N_A$ and $N_B$ for any given SNP within the same array. Therefore, a SNP genotype may be fully determined by an individual's data.

The art currently generally believes that perfect match probe intensities are proportional to the copy numbers, and has led to their use as a surrogate in many studies. However, this practice has been questioned on the basis of inaccuracy, and correction has been suggested by using the copy number in conjunction with probe binding affinity. LaFramboise et al., "Allele-specific amplification in cancer revealed by SNP array analysis" *PLoS Comput Biol* 1:e65 (2005); Zhang et al., "Free energy of DNA duplex formation on short oligonucleotide microarrays" *Nucleic Acids Research* 35:e1 8 (2007); Zhang et al., "A model of molecular interactions on short oligonucleotide microarrays" *Nature Biotechnology* 21:818-821 (2003); and Li et al., "Model-based analysis of oligonucleotide arrays: expression index computation and outlier detection" *Proc Natl Acad Sci USA* 98:31-36 (2001). Although it is not necessary to understand the mechanism of an invention, it is believed that the PICR model contemplated herein is the very first model that rigorously formulates the relationship of intensities among perfect match and mismatch probes with copy numbers, sequence binding affinity and background nonspecific-binding. It is further believed that the PICR model contemplated herein potentially provides a general framework to uncover the hidden and biological meaningful copy numbers by transforming noisy probe intensity data into cleaned copy number data. The data presented herein demonstrate that consistent and highly accurate results are obtained with embodiments of the PICR model contemplated by the present invention that would suggest that this transformation is highly advantageous to future genetic variation studies.

Finally, it should be recognized that although the presently contemplated models and methods were developed based on Affymetrix SNP arrays, the same approach is also applicable to other platforms of arrays with similar designs.

EXPERIMENTAL

Example I

Determination of Copy Number in SNP Array Samples

The SNP array samples of a HapMap trio dataset were downloaded from the Mapping 100K dataset (affymetrix.com/support/technical/sample_data/hapmap_trio_data.affx) and the Mapping 500K dataset (affymetrix.com/support/technical/sample_data/500k_data.affx). All the annotation files of the corresponding Affymetrix SNP array were downloaded from the Affymetrix website. Genotype annotation of the HapMap Project version 2005-03_16a_phaseI was used. The numbers of annotated SNPs on Mapping 50K Xba 240 Array and Mapping 250K Nsp array by 21 HapMap 2005-03_16a_phaseI were 41,099 and 67,394, respectively. Data from the Affymetrix 100K SNP arrays hybridized with samples of 1 to 5 copies of the X-chromosome (1X to 5X) were obtained from the Affymetrix Sample Data Sets for Copy Number Analysis Mismatch probes were found to contain non-negligible specific-binding information. For homozygous SNPs of genotype 'AA', all PA probes are perfect matches to target sequences, while other probes are mismatches through cross-hybridization: MA probes have one mismatch nucleotide at position 13, PB probes have one mismatch nucleotide at 6 position 13+k, and MB probes have two mismatch nucleotides at positions 13 and 13+k, k≠0. Probes interrogating 'BB' SNPs work similarly.

Figure 2A:
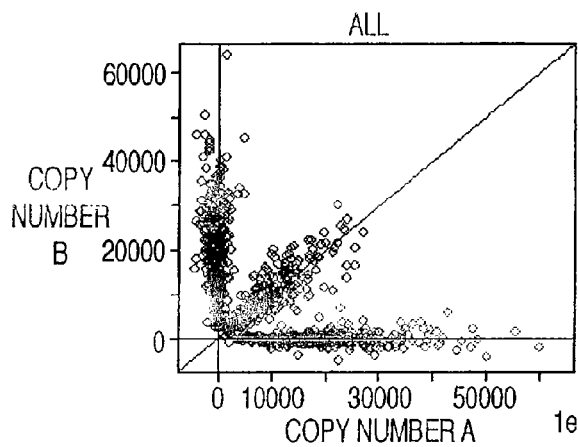
FIG. 2A: both perfect match and mismatch probes were used for model training and testing.
Figure 2B:
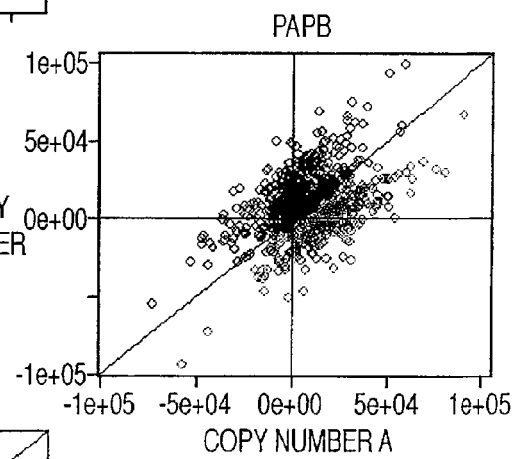
FIG. 2B: both perfect match and mismatch probes were used for model training but perfect match only for testing.
Figure 2C:
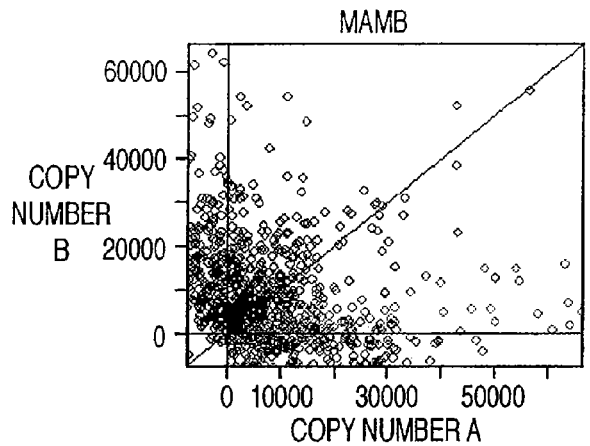
FIG. 2C: both perfect match and mismatch probes were used for model training but mismatch only for testing.
Figure 2D:
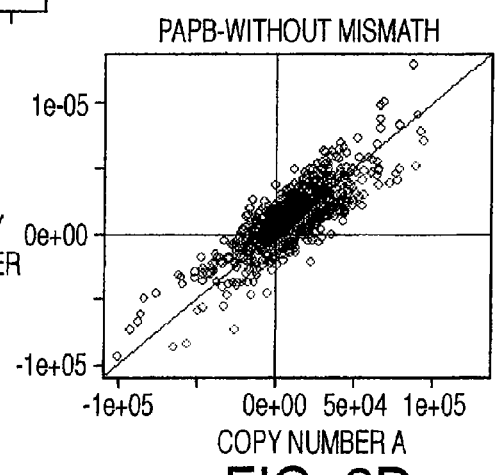
FIG. 2D: perfect match probes were used only for model training and testing.
Figure 4A:
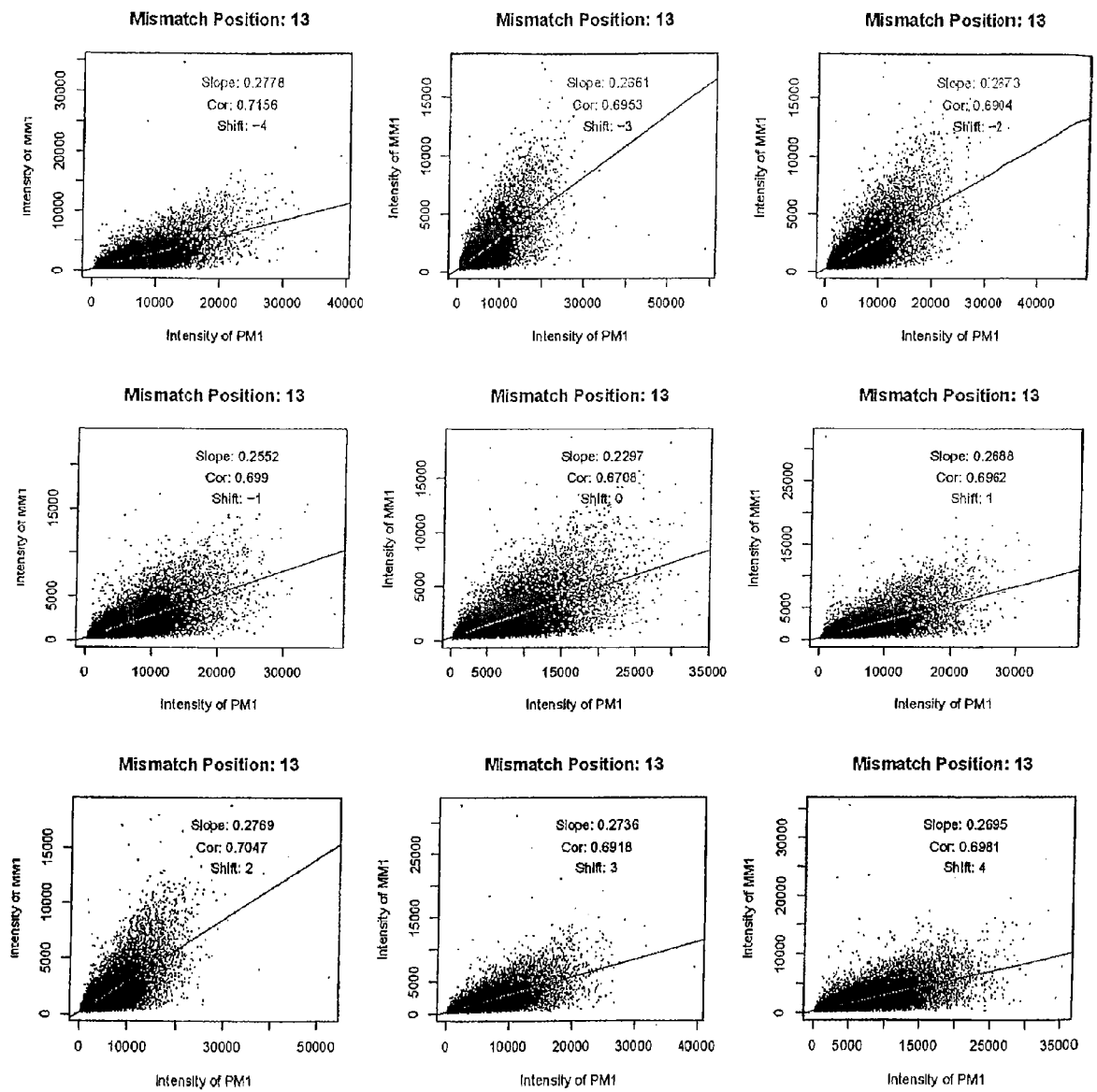
FIG. 4A presents exemplary data showing a plot of MM1 probe versus PM1 probe with one mismatch nucleotide at position 13.
Figure 4B:
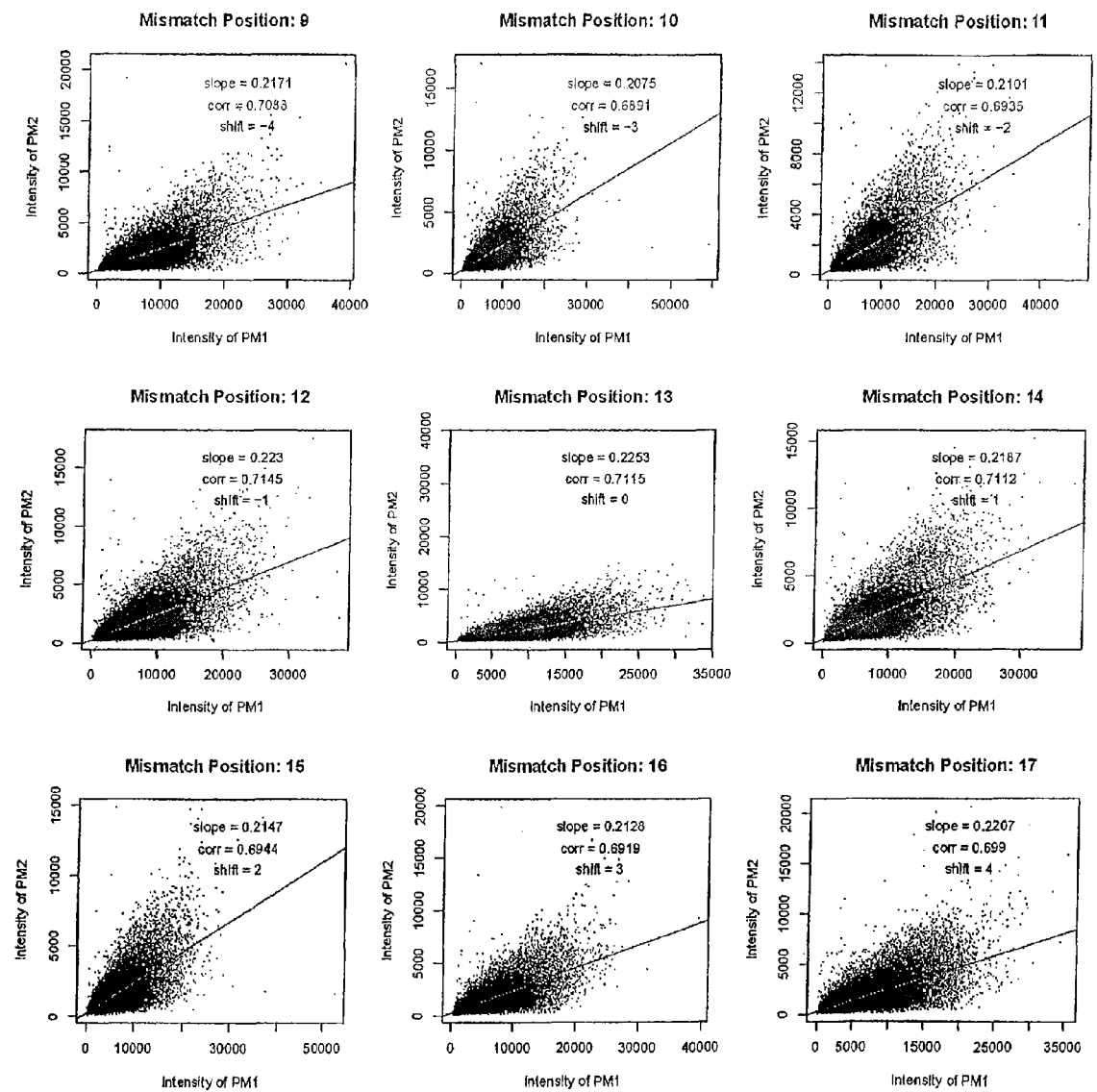
FIG. 4B presents exemplary data showing a plot of PM2 probe versus PM1 probe with one mismatch nucleotide at position 13+k.
Figure 4C:
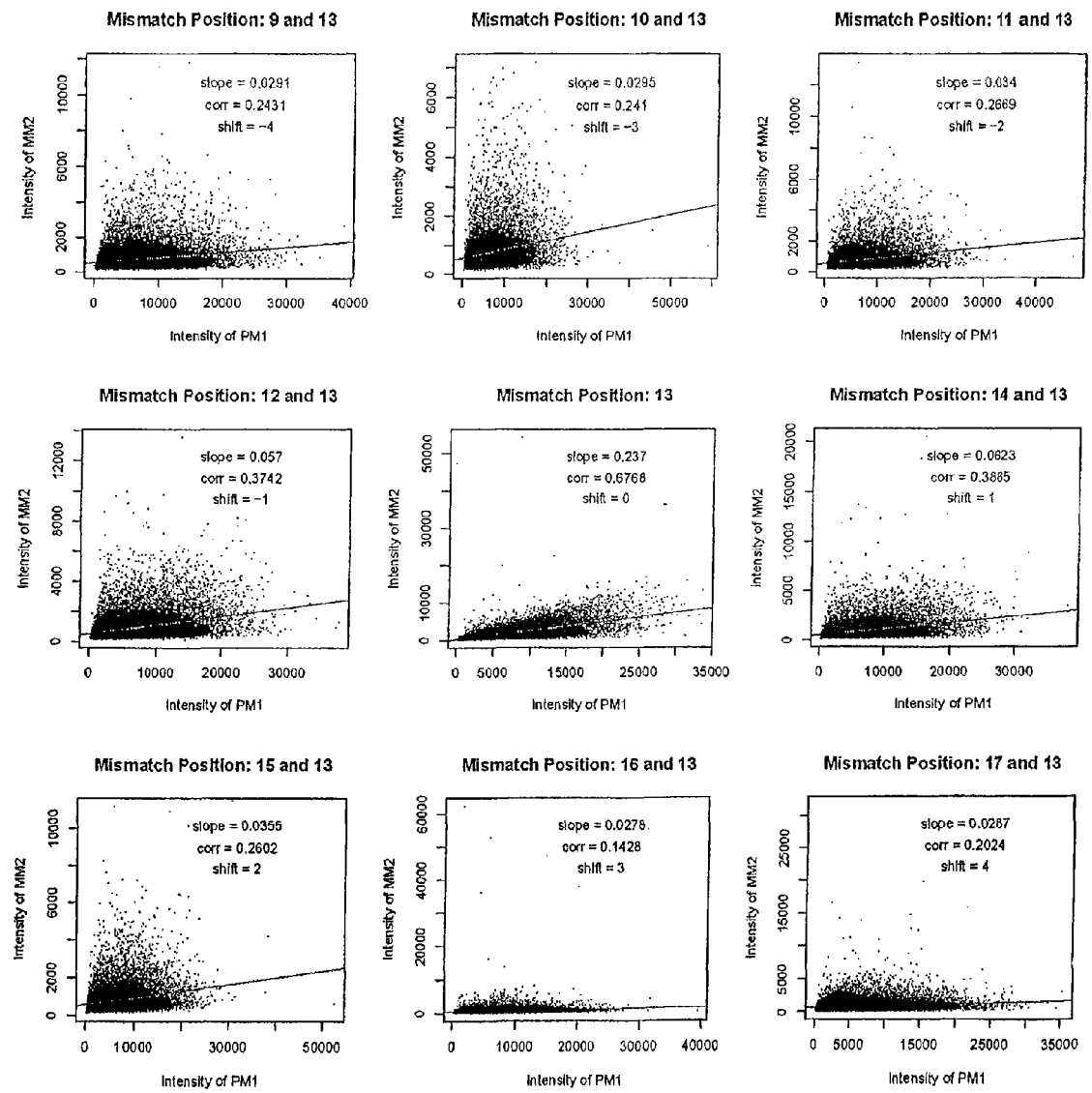
FIG. 4C presents exemplary data showing a plot of MM2 probe versus PM1 probe with two mismatch nucleotides at positions 13 and (13+k).

Scatter plots and correlations from one sample of the Mapping 50K Xba 240 Array show that there is critical information in mismatch probes; other samples were observed to behave similarly. FIGS. 4A, 4B and 4C.

Example II

Accurate Estimation of Probe Intensity with the PICR Model

Figure 5:
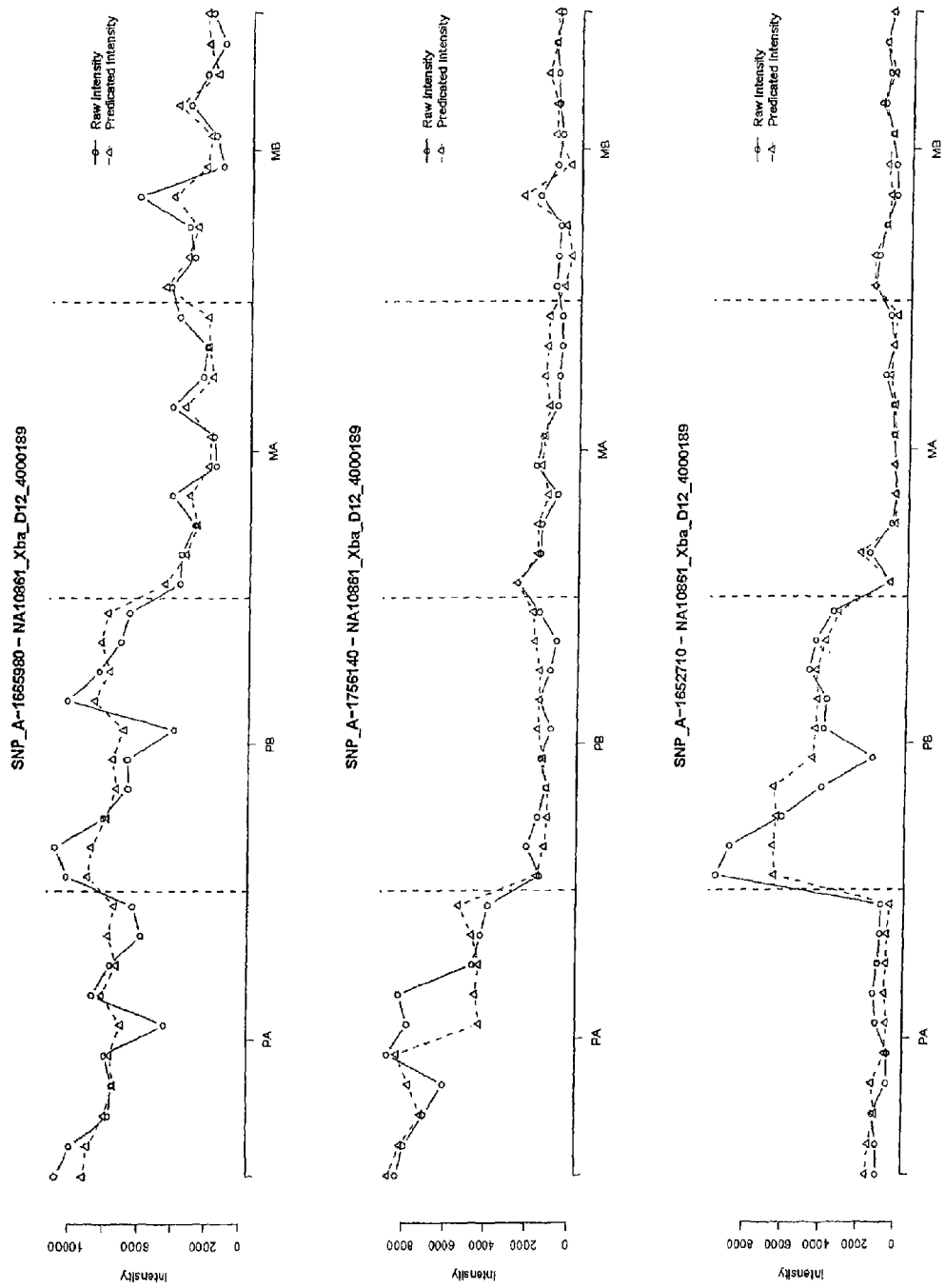
FIG. 5 presents a representative comparison of raw intensities with predicted intensities of the 40 probes (10 for each of PA, PB, MA and MB) by PICR for 3 randomly selected SNPs of different genotypes on one randomly selected non-training sample (NA10861_Xba_D12_4000189). Left panel—SNP_A-1665980 of 'AB' type; Center panel—

The PICR model not only provides a decomposition of probe intensity, but also estimates the intensity accurately. For example, a highly accurate estimation of probe intensities of randomly selected SNPs from a non-training sample for genotypes 'AB', 'AA' and 'BB' can be obtained with estimated parameters of the GPDNN and PICR. See, FIG. 5.

Example III

PICR Copy Number Estimation of the X Chromosome

This example, validates one embodiment of a copy number estimation method described herein. For example, a PICR model was applied to the cell-line data of experimentally confirmed 1 to 5 copies of the X-chromosome on Affymetrix SNP arrays that were used as a benchmark in the CARAT method for copy number variation study. Huang et al., "CARAT: a novel method for allelic detection of DNA copy number changes using high density oligonucleotide arrays" *BMC Bioinformatics* 7:83 (2006)

After a simple among-array normalization based on the estimated total copy numbers (A B 2 N N) of SNPs rather than on probe intensities, agreements between the estimated copy numbers and the true numbers of copies of the X-chromosome were examined. A 2X-chromosome sample was chosen as the reference sample to which the estimated copy numbers of other samples was compared. Among the total of 2,361 SNPs on the X-chromosome, 2,039 (86.4%) had a copy number correlation (Pearson correlation) 7 1 (>0.9999), and 2,290 (97.0%) had a copy number correlation greater than or equal to 0.9, where for each SNP the correlation is calculated from five pairs of numbers (estimated copy number and true copy number), corresponding to the 5 copies of the X-chromosome. This demonstrates a strong agreement between the estimated copy numbers and true copy numbers.

Scatter plots of the estimated total copy numbers of multiple-chromosome samples versus the reference sample were created for all 2,361 SNPs. See, FIG. 5. It can be seen that the estimated copy numbers are close to the true multiple of 2X-chromosomes (dashed lines). In contrast, the probe intensity-based CARAT method did not yield copy numbers as close to the true numbers of X chromosomes, even after the exclusion of about 20% of the SNPs that did not fit the CARAT model well.

Example IV

Estimating Parameters of the GPDNN

All 1974 parameters of the GPDNN model were estimated with one single sample of the Mapping 50K Xba 240 array (NA06985_Xba_B5_4000090), and the same sample used in the example for the illustration of specific-bindings of mismatch probes in FIG. 1. Only those homozygous SNPs with known genotype annotation by HapMap were used, which comprise more than 10,000 SNPs. The large amount of data for this large number of SNPs, together with 40 probes for each SNP, allows accurate estimation of the 1974 model parameters with an iterative algorithm, fitting the GPDNN model for probe sequences and fitting the PICR model with the Langmuir adsorption equation to estimate copy number, minimizing the loss function $l=\Sigma(\hat{I}_i-I_i)^2$ over all probes and selected SNPs, where $\hat{I}_i$ is the predicted value of probe intensity $I_i$ obtained from the PICR. The following algorithm was used for estimating the parameters for allele A with homozygous 'AA' SNPs. An analogous algorithm applies to 'BB' SNPs to estimate the parameters for allele B. The separate parameter training procedures for alleles A and B ensures the one copy number is 0 (zero).

The algorithm for training the parameters for allele A with 'AA' SNPs have the following steps:

1. Set initial binding free energy $\omega^{(0)}$ and $\lambda^{(0)}$ parameters as reported in Zhang et al. (2007) and to 0 (zero) for all other binding free energy parameters (e), $\theta^{(0)}$, $\kappa^{(0)}$, $\delta^{(0)}$, $\xi^{(0)}$) to 0 (zero).
2. In the mth iteration, assume the binding free energy parameters ($\omega^{(m)}\lambda^{(m)}$ ($\theta^{(m)}$, $\kappa^{(m)}$, $\delta^{(m)}$, $\xi^{(m)}$ are given. For one probe quartet of a given SNP, calculate the binding free energies $E^{(m)}=(\ldots, E_1^{(SPA,ks,STA)}, E_1^{(SPB,ks,STA)}, E_1^{(SMA,ks,STA)}, E_1^{(SMB,ks,STA)}, \ldots)^m$ and the binding affinity via the Langmuir adsorption function $\phi(E^{(m)})$.
3. Estimate the parameters $N_A^{(m)}$ and $b_i^{(m)}$ via a regression model and re-estimate the binding affinity $\phi$ and free energy $E^{(m+1)}$ assuming infinitesimal error.
4. Based on the estimates $E^{(m+1)}$ of all the SNPs, estimate the binding free energy parameters $\omega^{(m+1)}$ and $\lambda^{(m+1)}$ using the PA probes only by iteratively updating $\omega$ and $\lambda$ until convergence. Apply a similar procedure to $\theta^{(m+1)}$, $\kappa^{(m+1)}$, $\delta^{(m+1)}$ using the PB and MB probes only, with a fixed $\omega^{(m+1)}$ and $\lambda^{(m+1)}$. Finally, estimate $\xi^{(m+1)}$ by fixing $\omega^{(m+1)}$, $\lambda^{(m+1)}$, $\theta^{(m+1)}$, $\kappa^{(m+1)}$, $\delta^{(m+1)}$ using the MB probes and taking the mean difference of $E_2-E_1$ for each second mismatch nucleotide other than the mismatch nucleotide at position 13.
5. Repeat steps 2-4 until a convergence of all the free energy parameter estimates occur.

Although the GPDNN model provides accurate estimation of binding free energy by studying perfect match and mismatch probe sequences, the nonlinearity of binding affinity function $\phi(x)=1/1+e^x$ may make the estimation of model parameters subject to bias. To minimize bias in the copy number estimation, a Taylor expansion of unbiased functions of $\phi(x)$ was utilized (i.e., for example, $\phi(x+\Delta x)$. The expansion may be solved to identify a bias adjustment term $(-\frac{1}{2}\phi''(x)(\sigma^2)$. Ramsay et al. In: Functional data analysis. Springer, New York; Berlin (2005). This term may be used in the estimation of the model parameters and probe intensities.

Example, V

MA-Ratio with Application to Genotype Calling

For each given SNP, the allelic concentrations (copy numbers) for alleles A and B can be estimated with the linear regression (Wan et al 2009). The standardized allelic copy numbers (copy number estimates standardized with its variance covariance matrix) are expected to be normally distributed and independent with each other. An MA ratio is defined for the given SNP as:

$r=(N_A-N_B)/|N_A+N_B|$

The genotype calling criteria are provided based on this MA ratio that can properly separate the potential 3 genotype groups, AA, AB, and BB. The SNP-wise criteria are determined either by training of HapMap annotation or by unsupervised learning, depending on the availability of HapMap annotation for each SNP. Below is a summary of the criteria according to various scenarios of the HapMap annotations as follows:

1. HapMap SNPs having 3 groups of annotated genotypes
Number of SNPs: 228,008 in NSP array, 174,269 in STY array In general, for each given SNP, the median of MA ratio was first calculated for each annotated group as mA, mH, and mB for AA, AB and BB genotypes, respectively. Then, the cut-off values between homozygous and heterozygous are defined as:

$c1=(mA+mH)/2$ $c2=(mB+mH)/2$

Although it is not necessary to understand the mechanism of an invention, it was found that this calling criteria yielded good clustering for most of the SNPs and remained robust in the Wellcome Trust dataset (first 500 Controls). See FIG. 9 as an illustrated example. For FIGS. 9-14, the following color designations apply: "AA" SNPs in Blue; "AB" SNPs in Green; and "BB" SNPs in Red; "No call" SNPs in Black for HapMap. "Control samples" in Pink (500 control samples from Wellcome Trust data). Moreover, the issue of extreme values was fixed by going over the SNPs with extreme cut-offs up to 1% from the top of the data range and 1% from the bottom of the data range (about 8.5K SNPs). Thus, although it is not necessary to understand the mechanism of an invention, it is believed some annotation errors or mis-labelings of some SNPs in the HapMap samples may lead to poor genotype calls if not fixed, see FIG. 10.

2. SNPs with only 1 homozygous and 1 heterozygous annotations
Number of SNPs: 21,069 in NSP array, 18,402 in STY array Step 1: In this scenario, one of the homozygous groups was not observed in the HapMap samples due to the small minor allele frequency. It was noticed that the Wellcome Trust controls were selected from British population and were thus close to the HapMap CEU group genetically. Therefore, we first identified the SNPs with observed heterozygous in CEU population and combined roughly 500 Wellcome Trust controls with HapMap samples in searching for the minor homozygous group. Although it is not necessary to understand the mechanism of an invention, it was found that in general the third genotype group was able to be found and was helpful to setting up the calling criteria (about 7.5K in NSP array and 7K in STY). See FIG. 11A.

Step 2: For the remaining SNPs, some of them may still have 3 groups due to the incomplete or inaccurate HapMap annotation. In this situation, the first two observed groups were used to determine one cut-off value between AA and AB (or BB and AB), and further used the k-mean method to search for the third cluster beyond the 2 standard deviation of the MA ratios of the heterozygous group. See FIG. 11B. Three groups will be claimed if another cluster beyond heterozygous is found. Otherwise, the other cut-off is selected to be the mirror image of the first cutoff value about the median of the heterozygous group. See FIGS. 11C and 11D Step 3: The second cut-off may not be as accurate as the first one, since there is no information for the minor homozygous group. Potential problems were further examined by going over the SNPs with extreme cut-offs using the same threshold as in Scenario 1.

3. SNPs with only 2 homozygous annotations but no heterozygous annotation

Number of SNPs: 13 in NSP arrays and 7 in STY arrays

In this scenario, the number of SNPs is extremely small and the number of observations is usually dominating in one of the homozygous groups. Therefore, these SNPs were simply gone over and the criteria was selected visually. See FIGS. 12A and 12B. Although it is not necessary to understand the mechanism of an invention, some potential problems in the HapMap annotation were found.

4. SNPs with only 1 annotated homozygous

Number of SNPs: 232 in NSP array and 168 in STY array

Similar to the scenario 3, the number of SNPs is small and thus it is more likely to have potential annotation problems. Therefore, the SNPs here were gone over to select calling criteria and to identify the annotation problems. See FIGS. 13A and 13B.

5. SNPs with heterozygous annotation only

No SNPs found in either NSP or STY array.

6. SNPs with no HapMap annotation

Number of SNPs: 3,038 in NSP array and 2,721 in STY array

In this scenario, unsupervised learning was conducted with k-mean method after removing outliers.

Step 1: Outliers of MA ratios need to be removed before the k-mean procedure. We first sort the MA ratios and tried to remove those outliers from either the top or bottom. The removal process was stopped until the ratio was within 0.1 of the ratio next to it.

Step 2: The initial k-mean procedure was performed in searching for 3 clusters. After the clustering, the between-cluster distances were calculated as the minimum distance between cluster members. If the between clusters distances were less than 0.1, the k-mean procedure was rerun in searching for 2 clusters. The calling criteria could be made accordingly based on the k-mean result.

Step 3: We also went through the SNPs in this scenario for quality check and problem correction. See FIGS. 14A and 14B.

We claim:

1. A method, comprising:
    a) providing:
        i) a microarray comprising a first oligonucleotide and second oligonucleotide, said first oligonucleotide comprising a portion of a first allele, said second oligonucleotide comprising a portion of a second allele;
        ii) a labeled first probe having partial complementarity to a region of said first oligonucleotide;
        iii) a labeled second probe having complete complementarity to a region of said first oligonucleotide;
        iv) a labeled third probe having partial complementarity to a region of said second oligonucleotide; and
        v) a labeled fourth probe having complete complementarity of a region of said second oligonucleotide;
    b) exposing said first, second, third and fourth probes to said microarray under hybridization conditions to create bound probes;
    c) determining intensity measurements from said bound probes; and,
    d) determining a copy number for said first allele and said second allele using said intensity measurements of step c) and an algorithm, said algorithm utilizing an MA ratio.

2. The method of claim 1, wherein said microarray is an individual array.

3. The method of claim 1, wherein said method further comprises storing all microarray information in an algorithm as constants for optimal output.

4. The method of claim 1, wherein said method further comprises using a first and a second extreme cut-off wherein said first extreme cutoff is up to 1% from the top of the data range and said second extreme cut-off is up to 1% from the bottom of the data range.

5. The method of claim 1, wherein said microarray contains a plurality of SNPs with three annotated genotype groups.

6. The method of claim 1, wherein said microarray contains SNPs with only one annotated homozygous genotype and one annotated heterozygous genotype.

7. The method of claim 6, further comprising determining a first and a second cut-off for each of the homozygous genotype and the heterozygous genotype.

8. The method of claim 1, wherein said microarray contains a plurality of SNPs wherein said plurality contains only two annotated homozygous genotypes.

9. The method of claim 1, wherein said microarray contains a plurality of SNPs wherein said plurality contains only one annotated homozygous genotype.

10. The method of claim 1, wherein said microarray contains a plurality of SNPs wherein said plurality contains only SNPs with heterozygous annotation.

11. The method of claim 1, wherein said microarray contains a plurality of SNPs wherein said plurality contains no annotation.

* * * * *